United States Patent [19]

Murata et al.

[11] Patent Number: 5,420,122
[45] Date of Patent: * May 30, 1995

[54] 3-PYRROLIDINYLTHIO-1-AZABICYCLO-[3.2.0]HEPT-2-ENE-2-CARBOXYLIC ACID COMPOUNDS

[75] Inventors: Masayoshi Murata, Osaka; Hideo Tsutsumi, Toyonaka; Keiji Matsuda, Takatsuki; Kohji Hattori, Sakai; Takashi Nakajima, Toyonaka, all of Japan

[73] Assignee: Fujisawa Pharmaceutical Co., Ltd., Osaka, Japan

[*] Notice: The portion of the term of this patent subsequent to May 1, 2007 has been disclaimed.

[21] Appl. No.: 868,196

[22] Filed: Apr. 14, 1992

Related U.S. Application Data

[62] Division of Ser. No. 475,975, Feb. 6, 1990, Pat. No. 5,138,064, which is a division of Ser. No. 124,603, Nov. 24, 1987, Pat. No. 4,921,852.

[30] Foreign Application Priority Data

Nov. 24, 1986 [GB] United Kingdom ............... 8628060
Jul. 6, 1987 [GB] United Kingdom ............... 8715825

[51] Int. Cl.$^6$ .................. C07D 487/04; A61K 31/40
[52] U.S. Cl. .................... 514/210; 540/350; 548/127
[58] Field of Search ............ 540/350; 514/210; 548/127

[56] References Cited

U.S. PATENT DOCUMENTS 5,122,609  6/1992  Sunagawa ............ 540/350

FOREIGN PATENT DOCUMENTS 2236488  2/1973  Germany .

*Primary Examiner*—Robert Gerstl
*Attorney, Agent, or Firm*—Oblon, Spivak, McClelland, Maier & Neustadt

[57] ABSTRACT

Novel 3-pyrrolidinylthio-1-azabicyclo[3.2.0]hept-2-ene-2-carboxylic acid compounds and processes for their preparation are disclosed. These novel compounds have antimicrobial activity, and are useful as a medicament in the treatment of infectious diseases in human beings and animals.

17 Claims, No Drawings

3-PYRROLIDINYLTHIO-1-AZABICYCLO-[3.2.0]HEPT-2-ENE-2-CARBOXYLIC ACID COMPOUNDS

This is a division of application Ser. No. 07/475,975, filed on Feb. 6, 1990, U.S. Pat. No. 5,138,064, which is a division of application Ser. No. 07/124,603, filed Nov. 24, 1987, U.S. Pat. No. 4,921,852.

The present invention relates to novel 3-pyrrolidinylthio-1-azabicyclo[3.2.0]hept-2-ene-2-carboxylic acid compounds and pharmaceutically acceptable salts thereof.

More particularly, it relates to novel 3-pyrrolidinylthio-1-azabicyclo[3.2.0]hept-2-ene-2-carboxylic acid compounds and pharmaceutically acceptable salts thereof, which have antimicrobial activity, to processes for the preparation thereof, to a pharmaceutical composition comprising the same, and to a use of the same as a medicament and in the treatment of infectious diseases caused by pathogenic microorganisms in human being or animals.

Accordingly, one object of the present invention is to provide novel 3-pyrrolidinylthio-1-azabicyclo[3.2.0]hept-2-ene-2-carboxylic acid compounds and pharmaceutically acceptable salts thereof, which are highly active against a number of pathogenic microorganisms and are useful as antimicrobial agents.

Another object of the present invention is to provide processes for the preparation of novel 3-pyrrolidinylthio-1-azabicyclo[3.2.0]hept-2-ene-2-carboxylic acid compounds and salts thereof.

A further object of the present invention is to provide a pharmaceutical composition comprising, as an active ingredient, said 3-pyrrolidinylthio-1-azabicyclo-[3.2.0]hept-2-ene-2-carboxylic acid compounds and pharmaceutically acceptable salts thereof.

Still further object of the present invention is to provide a use of said 3-pyrrolidinylthio-1-azabicyclo[3.2.0]hept-2-ene-2-carboxylic acid compounds and pharmaceutically acceptable salts thereof as a medicament and in the treatment of infectious diseases caused by pathogenic microorganisms in human being or animals.

The object 3-pyrrolidinylthio-1-azabicyclo[3.2.0]-hept-2-ene-2-carboxylic acid compounds are novel and can be represented by the following general formula:

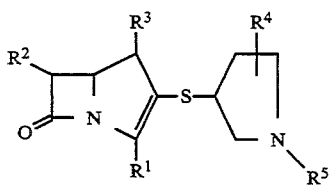

(I)

wherein $R^1$ is carboxy or protected carboxy,
$R^2$ is hydroxy (lower) alkyl or protected hydroxy(lower)alkyl,
$R^3$ is hydrogen or lower alkyl,
$R^4$ is heterocyclic group, which may have suitable substituent(s), and
$R^5$ is hydrogen or imino-protective group, and pharmaceutically acceptable salts thereof.

In the object compounds (I) and the intermediary compounds mentioned below, it is to be understood that there may be one or more stereo-isomeric pair(s) such as optical isomers due to asymmetric carbon atom(s), and such isomers are also included within the scope of the present invention.

Suitable pharmaceutically acceptable salts of the object compounds (I) are conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, dibenzylamine salt, etc.); a salt with anacid such as an inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, toluenesulfonate, etc.); a salt with a basic or acidic amino acid (e.g. arginine, aspartic acid, glutamic acid, etc.); an intermolecular quaternary salt; and the like.

According to the present invention, the object compounds (I) and pharmaceutically acceptable salts thereof can be prepared by the processes as illustrated by the following reaction schemes.

Process 1:

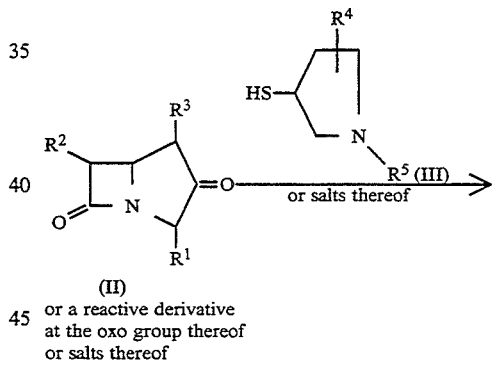

(II)
or a reactive derivative
at the oxo group thereof
or salts thereof

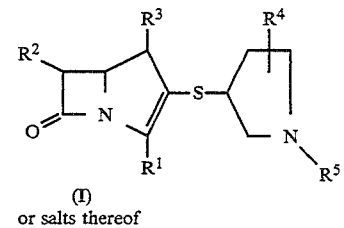

(I)
or salts thereof

Process 2:

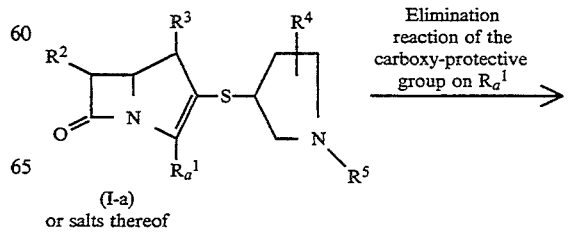

(I-a)
or salts thereof

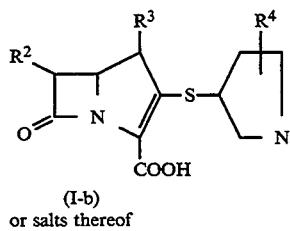

(I-b)
or salts thereof

Process 3:

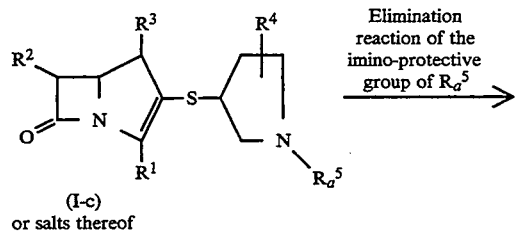

(I-c)
or salts thereof

Elimination reaction of the imino-protective group of $R_a^5$

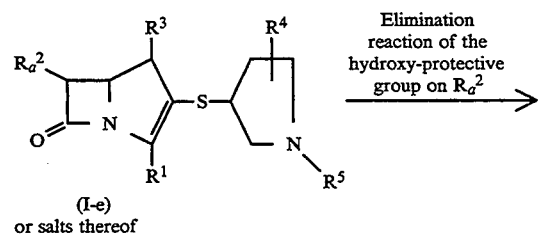

(I-d)
or salts thereof

Process 4:

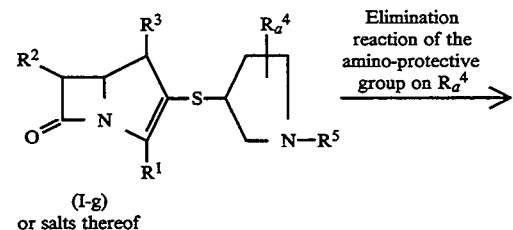

(I-e)
or salts thereof

Elimination reaction of the hydroxy-protective group on $R_a^2$ (I-f)
or salts thereof Process 5:

Elimination reaction of the amino-protective group on $R_a^4$ (I-g)
or salts thereof

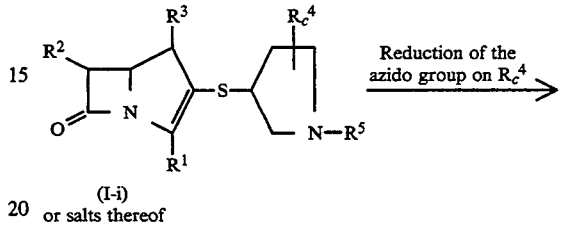

(I-h)
or salts thereof

Process 6:

Reduction of the azido group on $R_c^4$ (I-i)
or salts thereof (I-j)
or salts thereof Process 7:

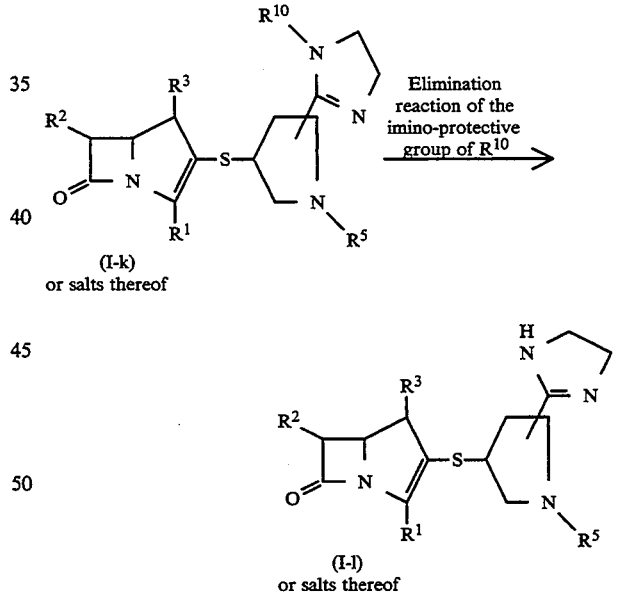

Elimination reaction of the imino-protective group of $R^{10}$ (I-k)
or salts thereof (I-l)
or salts thereof in which $R^1$, $R^2$, $R^3$, $R^4$ and $R^5$ are each as defined above,
$R_a^1$ is protected carboxy,
$R_a^2$ is protected hydroxy(lower)alkyl,
$R_b^2$ is hydroxy(lower)alkyl,
$R_a^4$ is heterocyclic group having protected amino or protected amino(lower)alkyl,
$R_b^4$ is heterocyclic group having amino or amino(lower) alkyl,
$R_c^4$ is heterocyclic group having azido(lower)alkyl,
$R_d^4$ is heterocyclic group having amino(lower)alkyl,
$R_a^5$ is imino-protective group, and
$R^{10}$ is imino-protective group.

The compound (III) used in the Process 1 is new and can be prepared, for example, by the following methods or a conventional manner.

Method A:

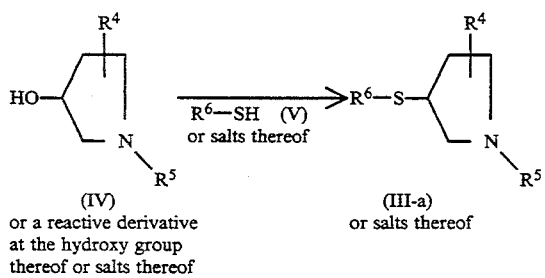

(IV)
or a reactive derivative at the hydroxy group thereof or salts thereof (III-a)
or salts thereof Method B:

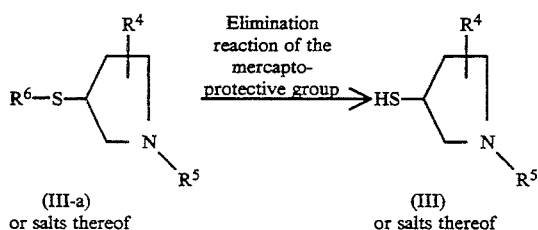

(III-a)
or salts thereof (III)
or salts thereof

Method C:

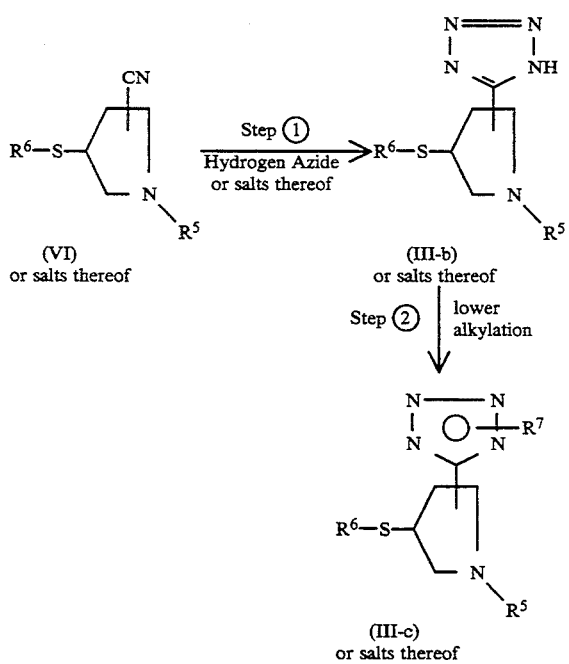

(VI)
or salts thereof (III-b)
or salts thereof (III-c)
or salts thereof

Method D:

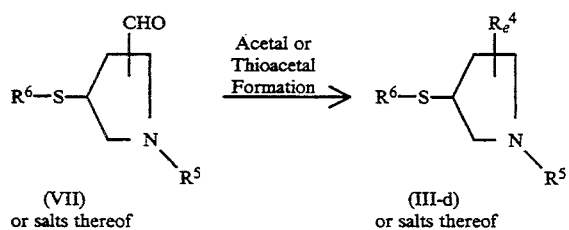

(VII)
or salts thereof (III-d)
or salts thereof

Method E:

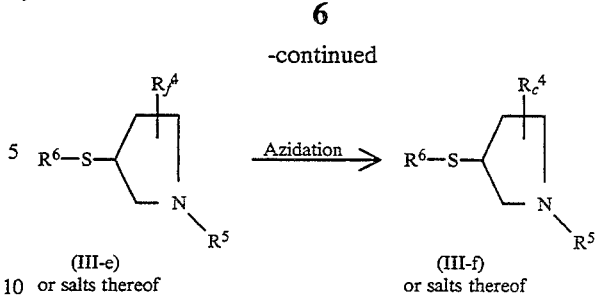

(III-e)
or salts thereof (III-f)
or salts thereof in which $R^4$, $R_c^4$ and $R^5$ are each as defined above, $R_e^4$ is optionally substituted 1,3-dioxolan-2-yl or 1,3-dioxan-2-yl, or optionally substituted 1,3-dithiolan-2-yl or 1,3-dithian-2-yl, $R_f^4$ is heterocyclic group having halo(lower)alkyl, $R^6$ is mercapto-protective group, and $R^7$ is lower alkyl.

In the above and subsequent descriptions of the present specification, suitable examples and illustrations of the various definitions which the present invention includes within the scope thereof are explained in detail as follows.

The term "lower" is intended to mean 1 to 6 carbon atoms, unless otherwise indicated.

Suitable "protected carboxy" may include esterified carboxy wherein esterified carboxy can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent (s), for example, lower alkanoyloxy (lower) alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-) acetoxybutyl ester, 1- (or 2-) propionyloxyethyl ester, 1-(or 2- or 3-)propionyloxypropyl ester, 1-(or 2-)butyryloxyethyl ester, 1- (or 2-) isobutyryloxyethyl ester, 1-(or 2-)pivaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-) pentanoyloxyethyl ester, etc.], lower alkanesulfonyl(lower) alkyl ester (e.g. 2-mesylethyl ester, etc.), mono (or di or tri) halo (lower) alkyl ester (e.g. 2-iodoethyl ester, 2,2,2-trichloroethyl ester, etc.), lower alkoxycarbonyloxy(lower) alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.], phthalidylidene(lower) alkyl ester, or (5-lower alkyl-2-oxo-1,3-dioxol-4-yl) (lower)alkyl ester [e.g. (5-methyl-2-oxo-1,3-dioxol-4-yl)methyl ester, (5-ethyl-2-oxo-1,3-dioxol-4-yl) methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower) alkyl ester which may have at least one suitable substituent(s) (e.g. benzyl ester, 4-methoxybenzyl ester, 4-nitrobenzyl ester, phenethyl ester, trityl ester, benzhydryl ester, bis (methoxyphenyl) methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

More preferable example of the protected carboxy thus defined may be phenyl($C_1$–$C_4$)alkoxycarbonyl which may have a nitro group and ($C_2$–$C_4$) alkenyloxycarbonyl, and the most preferable one may be 4-nitrobenzyloxycarbonyl.

Suitable "hydroxy (lower) alkyl" may include straight or branched lower alkyl having hydroxy-group such as hydroxymethyl, hydroxyethyl, hydroxypropyl, 1-(hydroxymethyl) ethyl, 1-hydroxy-1-methylethyl, hydroxybutyl, hydroxypentyl, hydroxyhexyl, and the like, in which more preferable example may be hydroxy($C_1$–$C_4$)alkyl and the most preferable one may be 1-hydroxyethyl.

Suitable "protected hydroxy(lower)alkyl" means aforementioned hydroxy(lower)alkyl, in which the hydroxy group is protected by a conventional hydroxy-protective group such as those mentioned in the explanation of imino-protective group as mentioned below; and further ar(lower)alkyl such as mono- or di- or triphenyl (lower) alkyl (e.g. benzyl, benzhydryl, trityl, etc.), etc.; trisubstituted silyl such as tri (lower)alkylsilyl (e.g. trimethylsilyl, triethylsilyl, isopropyldimethylsilyl, t-butyldimethylsilyl, diisopropylmethylsilyl, etc.), triarylsilyl (e.g. triphenylsilyl, etc.), triar(lower) alkylsilyl (e.g. tribenzylsilyl, etc.), etc.; and the like.

More preferable example of "protected hydroxy(lower) alkyl" thus defined may be phenyl($C_1$–$C_4$)-alkoxycarbonyloxy ($C_1$–$C_4$) alkyl which may have a nitro group, triphenyl ($C_1$–$C_4$)alkoxy($C_1$–$C_4$)alkyl and tri($C_1$–$C_4$)alkylsilyloxy($C_1$–$C_4$)alkyl.

Suitable "lower alkyl" may include straight or branched one such as methyl, ethyl, propyl, isopropyl, butyl, t-butyl, pentyl, hexyl, and the like, in which more preferable example may be $C_1$–$C_4$ alkyl and the most preferable one may be methyl.

Suitable "heterocyclic group" may include saturated or unsaturated, monocyclic or polycyclic heterocyclic group containing at least one hetero-atom such as oxygen, sulfur and nitrogen atom.

Preferable heterocyclic group may be unsaturated, 3 to 8-membered, more preferably 5 or 6-membered, heteromonocyclic group containing 1 to 4 nitrogen atom(s), for example, pyrrolyl, pyrrolinyl, imidazolyl, imidazolinyl (e.g. 2-imidazolinyl, etc.), pyrazolyl, pyrazolinyl, pyridyl, pyridyl N-oxide, pyridinio, dihydropyridyl, tetrahydropyridyl [e.g. 1,2,3,6-tetrahydropyridyl, etc.], pyrimidinyl, pyrimidinio, pyrazinyl, pyrazinio, pyridazinyl, pyridazinio, triazinyl [e.g. 1,3,5-triazinyl, 1,2,4-triazinyl and 1,2,3-triazinyl], tetrahydrotriazinyl [e.g. 1,2,5,6-tetrahydro-1,2,4-triazinyl, 1,4,5,6-tetrahydro-1,2,4-triazinyl, etc.], triazinio, triazolyl [e.g. 1H-1,2,4-triazolyl, 1H-1,2,3-triazolyl, 2H-1,2,3-triazolyl, etc.], triazolio, tetrazinyl, tetrazinio, tetrazolyl [e.g. 1H-tetrazolyl and 2H-tetrazolyl], tetrazolio, etc.;

unsaturated, 3 to 8-membered, more preferably 5 or 6-membered, heteromonocyclic group containing 1 to 2 sulfur atom(s) and 1 to 3 nitrogen atom(s), for example, thiazolyl, thiazolio, isothiazolyl, thiadiazolyl [e.g. 1,2,3-thiadiazolyl, 1,2,4-thiadiazolyl, 1,3,4-thiadiazolyl, 1,2,5-thiadiazolyl], thiadiazolio, thiazolinyl (e.g. 2-thiazolinyl, etc.), dihydrothiazinyl, etc.;

unsaturated, 3- to 8-membered, more preferably 5 or 6-membered, heteromonocyclic group containing 1 to 2 oxygen atom(s) and 1 to 3 nitrogen atom(s), for example, oxadiazolyl (e.g. 1,2,4-oxadiazolyl, 1,3,4-oxadiazolyl, 1,2,5-oxadiazolyl, etc.), etc.;

saturated, 3 to 8-membered, more preferably 5 or 6-membered, heteromonocyclic group containing 1 to 4 oxygen atom(s), for example, dioxolanyl (e.g. 1,3-dioxolanyl, etc.), dioxanyl (e.g. 1,3-dioxanyl, 1,4-dioxanyl, etc.), etc.;

saturated, 3 to 8-membered, more preferably 5 or 6-membered, heteromonocyclic group containing 1 to 4 sulfur atom(s), for example, dithiolanyl (e.g. 1,3-dithiolanyl, etc.), dithianyl (e.g. 1,3-dithianyl, 1,4-dithianyl, etc.), etc.; or the like, wherein said heterocyclic group may have one or more, preferably one to three suitable substituent(s) such as amino; protected amino in which the aminoprotective group may be the same as those for the imino-protective group as mentioned below; lower alkylamino (e.g. methylamino, ethylamino, propylamino, isopropylamino, butylamino, hexylamino, etc.); ureido(-lower)alkyl (e.g. ureidomethyl, ureidoethyl, ureidopropyl, ureidohexyl, etc.); carbamoyl; lower alkyl as mentioned above; amino(lower)alkyl (e.g. aminomethyl, aminoethyl, aminopropyl, aminobutyl, aminohexyl, etc.); protected amino (lower)alkyl, which is the amino (lower) alkyl group as mentioned above, in which the amino group is protected by a conventional amino-protective group such as those for the imino-protective group as mentioned below; hydroxy(lower)alkyl and protected hydroxy(lower)alkyl as mentioned above; azido (lower)alkyl (e.g. azidomethyl, azidoethyl, azidopropyl, azidohexyl, etc.); halo(lower)alkyl (e.g. chloromethyl, bromomethyl, iodoethyl, bromopropyl, bromohexyl, etc.); and the like. And further in case that said heterocyclic group is imidazolinyl, the imino-moiety of imidazoline ring may be protected by a conventional imino-protective group as mentioned below.

Preferable example of "heterocyclic group, which may have suitable substituent(s)" may be:

imidazolinyl (e.g. 2-imidazolin-2-yl, etc.);
N-protected imidazolinyl such as N-acylimidazolinyl, more preferably N-phenyl (or nitrophenyl) ($C_1$–$C_4$)-alkoxycarbonylimidazolinyl [e.g. 1-(4-nitrobenzyloxycarbonyl)-2-imidazolin-2-yl, etc.];
triazolyl (e.g. 1H-1,2,4-triazol-3-yl, etc.);
amino(lower)alkyltriazolyl, more preferably amino ($C_1$–$C_4$)alkyltriazolyl (e.g. 3-aminomethyl-1H-1,2,4-triazol-5-yl, etc.);
protected amino(lower)alkyltriazolyl such as acylamino(lower)alkyltriazolyl, more preferably phenyl(or nitrophenyl) ($C_1$–$C_4$)alkoxycarbonylamino-($C_1$–$C_4$) alkyltriazolyl [e.g. 3-(4-nitrobenzyloxycarbonylaminomethyl)-1H-1,2,4-triazol-5-yl, etc.];
tetrazolyl (e.g. 1H-tetrazol-5-yl, etc.);
lower alkyltetrazolyl, more preferably $C_1$–$C_4$ alkyltetrazolyl (e.g. 1-methyl-1H-tetrazol-5-yl, 2-methyl-2H-tetrazol-5-yl, etc.);
thiazolyl (e.g. thiazol-4-yl, etc.);
aminothiazolyl (e.g. 2-aminothiazol-4-yl, etc.);
lower alkylthiazolyl, more preferably $C_1$–$C_4$ alkylthiazolyl (e.g. 2-methylthiazol-4-yl, etc.);
carbamoylthiazolyl (e.g. 4-carbamoylthiazol-2-yl, etc.);
lower alkylaminothiazolyl, more preferably $C_1$–$C_4$ alkylaminothiazolyl (e.g. 2-methylaminothiazol-4-yl, etc.);

amino(lower)alkylthiazolyl, more preferably amino($C_1$–$C_4$) alkylthiazolyl [e.g. 2-aminomethylthiazol-4-yl, 2-(2-aminoethyl)thiazol-4-yl, etc.];

protected amino(lower)alkylthiazolyl such as acylamino(lower)alkylthiazolyl, more preferably phenyl(or nitrophenyl) ($C_1$–$C_4$)alkoxycarbonylamino($C_1$–$C_4$) alkylthiazolyl [e.g. 2-(4-nitrobenzyloxycarbonylaminomethyl) thiazol-4-yl, 2-[2-(4nitrobenzyloxycarbonylamino) ethyl]thiazol-4-yl, etc.];

protected hydroxy(lower)alkylthiazolyl such as acyloxy(lower)alkylthiazolyl, more preferably carbamoyloxy($C_1$–$C_4$)alkylthiazolyl (e.g. 2-carbamoyloxymethylthiazol-4-yl, etc.);

thiadiazolyl (e.g. 1,2,4-thiadiazol-5-yl, etc.);

lower alkylaminothiadiazolyl, more preferably $C_1$–$C_4$ alkylaminothiadiazolyl (e.g. 5-methylamino-1,3,4-thiadiazol-2-yl, etc.);

thiazolinyl (e.g. 2-thiazolin-2-yl, etc.);

aminooxadiazolyl (e.g. 3-amino-1,2,4-oxadiazol-5-yl, etc.);

amino(lower)alkyloxadiazolyl, more preferably amino($C_1$–$C_4$)alkyloxadiazolyl, (e.g. 3-aminomethyl-1,2,4-oxadiazol-5-yl, etc.);

oxadiazolyl (e.g. 1,2,4-oxadiazol-5-yl, etc.);

ureido (lower) alkylthiazolyl, more preferably ureido($C_1$–$C_4$)alkylthiazolyl (e.g. 2-ureidomethylthiazol-4-yl, etc.);

azido(lower)alkylthiazol, more preferably azido ($C_1$–$C_4$)alkylthiazolyl (e.g. 4-azidomethylthiazol-2-yl, etc.);

amino(lower)alkylthiazolyl, more preferably amino($C_1$–$C_4$)alkylthiazolyl (e.g. 4-aminomethylthiazol-2-yl, etc.);

imidazolyl (e.g. imidazol-2-yl, etc.);

protected amino(lower)alkyloxadiazolyl such as acylamino(lower)alkyloxadiazolyl, more preferably phenyl(or nitrophenyl)($C_1$–$C_4$)alkoxycarbonylamino($C_1$–$C_4$) alkyloxadiazolyl [e.g. 3-(4-nitrobenzyloxycarbonylaminomethyl)-1,2,4-oxadiazol-5-yl, etc.);

dioxolanyl (e.g. 1,3-dioxolan-2-yl, etc.];

amino(lower)alkyldioxolanyl, more preferably amino($C_1$–$C_4$)alkyldioxolanyl (e.g. 4-aminomethyl-1,3-dioxolan-2-yl, etc.);

azido(lower)alkyldioxolanyl, more preferably azido ($C_1$–$C_4$) alkyldioxolanyl (e.g. 4-azidomethyl-1,3-dioxolan-2-yl, etc.);

hydroxy(lower)alkyldioxolanyl, more preferably hydroxy($C_1$–$C_4$)alkyldioxolanyl (e.g. 4-hydroxymethyl-1,3-dioxolan-2-yl, etc.);

aminodioxanyl (e.g. 5-amino-1,3-dioxan-2-yl, etc.);

protected aminodioxanyl such as acylaminodioxanyl, more preferably phenyl(or nitrophenyl) ($C_1$–$C_4$) alkoxycarbonylaminodioxanyl [e.g. 5-(4-nitrobenzyloxycarbonylamino)-1,3-dioxan-2-yl, etc.];

dithiolanyl (e.g. 1,3-dithiolan-2-yl, etc.); and dithianyl (e.g. 1,3-dithian-2-yl, etc.);

Furthermore, when the heterocyclic group as stated above is, for example, thiazolyl having amino or protected amino group at 2-position, or 1,2,4-oxadiazolyl having amino or protected amino group at 3-position, there are tautomeric isomers as shown by the following equilibriums:

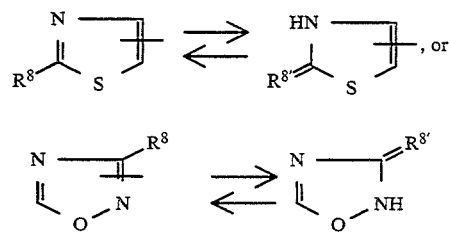

(wherein $R^8$ is amino or protected amino, and
$R^{8'}$ is imino or protected imino).

All of the above tautomeric isomers are included within the scope of the present invention, and in the present specification, however, the object and intermediary compounds including the group of such tautomeric isomers are represented by using one of the expressions therefor, i.e. 2-amino (or protected amino) thiazolyl and the formula:

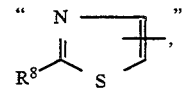

or 3-amino (or protected amino) -1,2,4-oxadiazolyl and the formula:

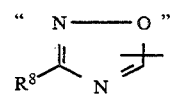

only for the convenient sake.

And further, when the heterocyclic group as stated above is, for example, 1,2,4-triazolyl or tetrazolyl group, there are tautomeric isomers as shown by the following equilibriums:

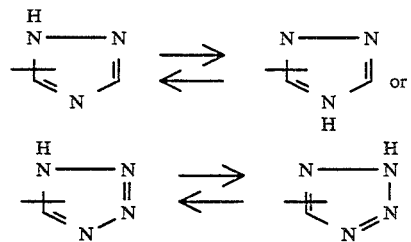

All of the above tautomeric isomers are included within the scope of the present invention and in the present specification, however, the object and intermediary compounds including the group of such tautomeric isomers are represented by using one of the expressions therefor , i.e. 1H-1,2,4-triazolyl and the formula:

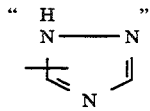

or 1H-tetrazolyl and the formula:

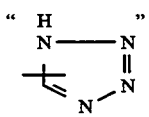

only for the convenient sake.

Suitable "imino-protective group" may include acyl such as carbamoyl, aliphatic acyl, aromatic acyl, heterocyclic acyl and aliphatic acyl substituted with aromatic or heterocyclic group (s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower) alkanecarbonyl (e.g. cyclopropanecarbonyl, cyclopentanecarbonyl, cyclohexanecarbonyl, etc.), and the like.

The aromatic acyl may include aroyl (e.g. benzoyl, toluoyl, xyloyl, etc.), N-arylcarbamoyl (e.g. N-phenylcarbamoyl, N-tolylcarbamoyl, N-naphthylcarbamoyl, etc.), arenesulfonyl (e.g. benzenesulfonyl, tosyl, etc.), and the like.

The heterocyclic acyl may include heterocycliccarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include aralkanoyl such as phenyl(lower)alkanoyl (e.g. phenylacetyl, phenylpropionyl, phenylhexanoyl, etc.), aralkoxycarbonyl such as phenyl(lower)alkoxycarbonyl (e.g. benzyloxycarbonyl, phenethyloxycarbonyl, etc.), aryloxyalkanoyl such as phenoxy(lower)alkanoyl (e.g. phenoxyacetyl, phenoxypropionyl, etc.), and the like.

The aliphatic acyl substituted with heterocyclic group(s) may include heterocyclic-alkanoyl such as heterocyclic (lower) alkanoyl (e.g. thienylacetyl, imidazolylacetyl, furylacetyl, tetrazolylacetyl, thiazolylacetyl, thiadiazolylacetyl, thienylpropionyl, thiadiazolylpropionyl, etc.), and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro, and the like, and preferable acyl having such substituent(s) may be mono(or di or tri)haloalkanoyl (e.g. chloroacetyl, bromoacetyl, dichloroacetyl, trifluoroacetyl, etc.), mono(or di or tri)haloalkoxycarbonyl (e.g. chloromethoxycarbonyl, dichloromethoxycarbonyl, 2,2,2-trichloroethoxycarbonyl, etc.) , nitro(or halo or lower alkoxy)aralkoxycarbonyl (e.g. nitrobenzyloxycarbonyl, chlorobenzyloxycarbonyl, methoxybenzyloxycarbonyl, etc.), mono(or di or tri)halo (lower)alkylsulfonyl (e.g. fluoromethylsulfonyl, difluoromethylsulfonyl, trifluoromethylsulfonyl, trichloromethylsulfonyl, etc.), and the like.

More preferable example of "imino-protective group" thus defined may be $(C_2-C_4)$alkenyloxycarbonyl and phenyl$(C_1-C_4)$alkoxycarbonyl which may have a nitro group, and the most preferable one may be 4-nitrobenzyloxycarbonyl.

Suitable "mercapto-protective group" may include acyl as mentioned above, ar(lower)alkyl such as mono- or di- or triphenyl (lower) alkyl (e.g. benzyl, phenethyl, benzhydryl, trityl, etc.), and the like, in which more preferable example may be $C_1-C_4$ alkanoyl, aroyl and triphenyl$(C_1-C_4)$alkyl, and the most preferable one may be benzoyl.

Suitable heterocyclic moieties of "heterocyclic group having amino or amino(lower)alkyl", "heterocyclic group having protected amino or protected amino(lower)alkyl", "heterocyclic group having azido (lower) alkyl", "heterocyclic group having amino (lower) alkyl" and "heterocyclic group having halo(lower)alkyl" are the same as those for the heterocyclic group as exemplified above.

Suitable "amino (lower) alkyl", "protected amino", "protected amino (lower) alkyl", "azido (lower) alkyl" and "halo(lower) alkyl as the substituents of the heterocyclic moiety mentioned above are the same as those exemplified as the substituent of the heterocyclic group mentioned above.

Suitable substituent of "optionally substituted 1,3-dioxolan -2-yl or 1,3-dioxan-2 -yl" and "optionally substituted 1,3-dithiolan-2-yl or 1,3-dithian-2-yl" are the same as those exemplified as the substituents of the heterocyclic group mentioned above.

The processes for the preparation of the object compound (I) of the present invention are explained in detail in the following.

(1) Process 1

The compounds (I) or salts thereof can be prepared by reacting the compound (II) or a reactive derivative at the oxo group thereof or salts thereof with the compound (III) or salts thereof.

Suitable salts of the compound (II) may be salts with bases such as those given for the compounds (I).

The reactive derivative at the oxo group of the compound (II) can be represented by the following formula (II'), which is preferably used in this reaction and can be prepared by reacting the compound (II) or salts thereof with an acylating agent.

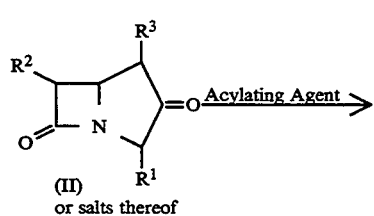

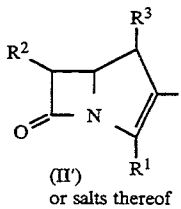

(II')
or salts thereof in which $R^1$, $R^2$ and $R^3$ are each as defined above, and $R^9$ is acyl as exemplified for the imino-protective group and further O,O-substituted phosphono derived from, for example, organic phosphoric acid mentioned hereinbelow.

Suitable acylating agents may include conventional ones which can introduce the acyl group as mentioned above into the compound (II), and preferable acylating agents may be organic sulfonic or phosphoric acid or its reactive derivative such as acid halide, acid anhydride, and the like, for example, arenesulfonyl halide (e.g. benzenesulfonyl chloride, p-toluenesulfonyl chloride, p-nitrobenzenesulfonyl chloride, p-bromobenzenesulfonyl chloride, etc.), arenesulfonic anhydride (e.g. benzenesulfonic anhydride, p-toluenesulfonic anhydride, p-nitrobenzenesulfonic anhydride, etc.), lower alkanesulfonyl halide which may have additional halogen (e.g. methanesulfonyl chloride, ethanesulfonyl chloride, trifluoromethanesulfonyl chloride, etc.), lower alkanesulfonic anhydride which may have halogen (e.g. methanesulfonic anhydride, ethanesulfonic anhydride, trifluoromethanesulfonic anhydride, etc.), di(lower) alkyl phosphorohaloridate (e.g. diethyl phosphorochloridate, etc.), diaryl phosphorohaloridate (e.g. diphenyl phosphorochloridate, etc.), and the like.

This acylation reaction is usually carried out in a conventional solvent which does not adversely influence the reaction such as acetone, dioxane, acetonitrile, chloroform, dichloromethane, hexamethylphosphoramide, dichloroethane, tetrahydrofuran, ethyl acetate, dimethylsulfoxide, N,N-dimethylformamide, pyridine, etc., or a mixture thereof.

When the acylating agent is used in a free acid form or its salt form in this reaction, the reaction is preferably carried out in the presence of a conventional condensing agent such as carbodiimide compounds (e.g. N,N'-diethylcarbodiimide, N,N'-diisopropylcarbodiimide, N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, etc.); N,N'-carbonyldiimidazole, N,N'-carbonylbis (2-methylimidazole); keteneimine compounds (e.g. pentamethyleneketene-N-cyclohexylimine, diphenylketene-N-cyclohexylimine); ethoxyacetylene; 1-alkoxy-1-chloroethylene; ethyl polyphosphate; isopropyl polyphosphate; phosphorus oxychloride; phosphorus trichloride; thionyl chloride; oxalyl chloride; a combination of triphenylphosphine with carbon tetrachloride or diazenedicarboxylate; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

This acylation reaction may be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compound [e.g. pyridine, picoline, lutidine, N, N-di(lower)alkylaminopyridine such as N,N-dimethylaminopyridine, etc.], quinoline, N-lower alkylmorphorine (e.g. N-methylmorphorine, etc.), N,N-di(lower)alkylbenzylamine (e.g. N,N-dimethylbenzylamine, etc.), alkali metal alkoxide (e.g. sodium methoxide, sodium ethoxide, potassium butoxide, etc.), and the like.

The reaction temperature of this acylation reaction is not critical and the reaction is usually carried out under from cooling to warming.

With regard to the compound (II), it is to be noted that the 3,7-dioxo-1-azabicyclo [3.2.0]heptane ring system of the following formula (IIA) is well known to lie to tautomeric relation with the 3-hydroxy-7-oxo-1-azabicyclo [3.2.0]hept-2-ene ring system of the following formula (IIB), and accordingly, it is to be understood that both of these ring systems are substantially the same.

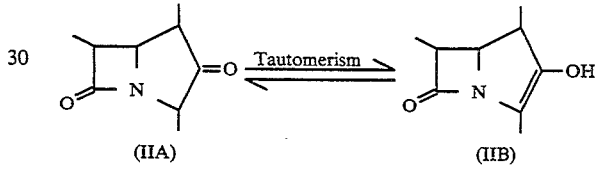

(IIA)     (IIB)

The compound (II') or salts thereof can be used with or without isolation for the subsequent reaction with the compound (III) or salts thereof.

Suitable salts of the compound (III) may be the same as those for the compound (I) and silver salt.

The reaction of the compound (II) or its reactive derivative or salts thereof with the compound (III) or salt thereof can be carried out in the presence of an organic or inorganic base such as those given in the explanation of the acylation reaction as stated above.

This reaction can be carried out in a conventional solvent which does not adversely influence the reaction such as those given in the explanation of the acylation reaction.

The reaction temperature is not critical and the reaction is usually carried out under from cooling to warming.

(2) Process 2

The compound (I-b) or salts thereof can be prepared by subjecting the compound (I-a) or salts thereof to elimination reaction of the carboxyprotective group on $R_a{}^1$.

Suitable salts of the compounds (I-a) and (i-b) may be the same as those for the compounds (I).

The present reaction is usually carried out by a conventional method such as hydrolysis, reduction, and the like.

(i) Hydrolysis

Hydrolysis is preferably carried out in the presence of a base or an acid. Suitable base may include an alkali metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), an alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

In case that the hydroxy-protective group is tri(-lower)alkylsilyl, the hydrolysis can be carried out in the presence of tri(lower) alkylammonium halide (e.g. tributylammonium fluoride, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction

The reduction method applicable for this elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinium plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

In case that the carboxy-protective group is allyl group, it can be deprotected by hydrogenolysis using a palladium compound.

Suitable palladium compound used in this reaction may be palladium on carbon, palladium hydroxide on carbon, palladium chloride, a palladium-ligand complex such as tetrakis(triphenylphosphine)palladium (0), bis(-dibenzylideneacetone)palladium(0), di[1,2-bis(diphenyphosphino)ethane]palladium(0), tetrakis(triphenylphosphite)palladium(0), tetrakis(triethyl phosphite)palladium(0), and the like.

This reaction can preferably be carried out in the presence of a scavenger of allyl group generated in situ, such as amine (e.g. morpholine, N-methylaniline, etc.), an activated methylene compound (e.g. dimedone, benzoylacetate, 2-methyl-3-oxovaleric acid, etc.), a cyanohydrin compound (e.g. α-tetrahydropyranyloxybenzyl cyanide, etc. ), lower alkanoic acid or a salt thereof (e.g. formic acid, acetic acid, ammonium formate, sodium acetate, etc.) , N-hydroxysuccinimide, and the like.

This reaction can be carried out in the presence of a base such as lower alkylamine (e.g. butylamine, triethylamine, etc.), pyridine, and the like.

When palladium-ligand complex is used in this reaction, the reaction can preferably be carried out in the presence of the corresponding ligand (e.g. triphenylphosphine, triphenyl phosphite,, triethyl phosphite,, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, etc., The elimination reaction can be selected according to the kind of carboxy-protective group to be eliminated.

The present process includes within the scope thereof a case that the hydroxy- and/or imino-protective group(s) for $R^2$ and $R^5$, and amino- and/or imino-protective group(s) on $R^4$ are removed or azido group on $R^4$ is reduced to amino group at the same time during the reaction.

(3) Process 3

The compound (I-d) or salts thereof can be prepared by subjecting the compound (I-c) or salts thereof to elimination reaction of the imino-protective group of $R_a^5$.

Suitable salts of the compounds (I-c) and (I-d) may be the same as those for the compounds (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for elimination reaction of the carboxy-protective group of the compound (I-a) in Process 2, and therefore are to be referred to said explanation.

The present process includes within the scope thereof a case that the carboxy- and/or hydroxy-protective group(s) for $R^1$ and $R^2$, and amino- and/or imino-protective group(s) on $R^4$ are eliminated or azido group on $R^4$ is reduced to amino group at the same time during the reaction.

(4) Process 4

The compound (I-f) or salts thereof can be prepared by subjecting the compound (I-e) or salts thereof to elimination reaction of the hydroxy-protective group on $R_a^2$.

Suitable salts of the compounds (I-e) and (I-f) may be the same as those for the compound (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for elimination reaction of the carboxy-protective group of the compound (I-a) in Process 2, and therefore are to be referred to said explanation.

The present process includes within the scope thereof a case that the carboxy- and/or imino-protective group(s) for $R^1$ and $R^5$, and amino- and/or imino-protective group(s) on $R^4$ are removed or azide group on $R^4$ is reduced to amino group at the same time during the reaction.

(5) Process 5

The compound (I-h) or salts thereof can be prepared by subjecting the compound (I-g) or salts thereof to elimination reaction of the amino-protective group on $R_a^4$.

Suitable salts of the compound (I-g) and (I-h) may be the same as those for the compound (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for elimination reaction of the carboxy-protective group of the compound (I-a) in Process 2, and therefore are to be referred to said explanation.

The present process includes within the scope thereof a case that the carboxy-protective group for $R^1$, the hydroxy-protective group for $R^2$ and/or the imino-protective group for $R^5$ are removed at the same time during the reaction.

This reaction can be carried out in the presence of an organic or inorganic base such as those given in the explanation of Process 1.

(6) Process 6

The compound (I-j) or salts thereof can be prepared by subjecting the compound (I-i) or salts thereof to reduction of the azido group on $R_c^4$.

Suitable salts of the compounds (I-i) and (I-j) may be the same as those for the compound (I).

This reduction is usually carried out by a conventional method such as catalytic reduction, and the like.

The method of reduction, and the reaction conditions (e.g. reaction temperature, solvent, etc.) are substantially the same as those illustrated for elimination reaction of the carboxy-protective group of the compound (I-a) in Process 2, and therefore are to be referred to said explanation.

The present process includes within the scope thereof a case that the carboxy-protective group for $R^1$, the hydroxy-protective group for $R^2$ and/or the imino-protective group for $R^5$ are removed at the same time during the reaction.

(7) Process 7

The compound (I-l) or salts thereof can be prepared by subjecting the compound (I-k) or salts thereof to elimination reaction of the imino-protective group of $R^{10}$.

Suitable salts of the compounds (I-k) and (I-l) may be the same as those for the compounds (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for elimination reaction of the carboxy-protective group of the compound (I-a) in Process 2, and therefore are to be referred to said explanation.

The present process includes within the scope thereof a case that the carboxy-protective group for $R^1$, the hydroxy-protective group for $R^2$ and/or the imino-protective group for $R^5$ are removed at the same time during the reaction.

Methods A to E for preparing the new starting compound (III) or salts thereof are explained in detail in the following.

(A) Method A

The compound (III-a) or salts thereof can be prepared by reacting the compound (IV) or a reactive derivative at the hydroxy group thereof or salts thereof with the compound (V) or salts thereof.

Suitable salts of the compounds (III-a), (IV) may be the same as those for the compounds (I)

Suitable salts of the compound (V) may be salts with bases such as those given for the compounds (I).

Suitable reactive derivative at the hydroxy group of the compound (IV) may include a conventional one such as halide (e.g. chloride, bromide, iodide, etc.), sulfonate (e.g. methanesulfonate, benzenesulfonate, toluenesulfonate, etc.), and the like, in which more preferable example may be sulfonate.

The starting compound (IV) of this method is new and can be prepared by the methods described in the Preparations mentioned below.

Preferable example of the compound (V) may be ar(lower)alkanethiol such as mono- or di- or triphenyl(lower)alkanethiol (e.g. phenylmethanethiol, diphenylmethanethiol, triphenylmethanethiol, etc.), thio(lower)alkanoic S-acid (e.g. thioacetic S-acid, etc.), thioarenoic S-acid (e.g. thiobenzoic S-acid, etc.), and the like, in which more preferable example may be triphenyl ($C_1$–$C_4$) alkanethiol, thio ($C_1$–$C_4$)alkanoic S-acid and thio($C_6$–$C_{10}$)arenoic S-acid, and the most preferable one may be triphenylmethanethiol, thioacetic S-acid and thiobenzoic S-acid.

In case that the compound (V) may be ar(lower)alkanethiol, the starting compound (IV) of the present reaction is preferably used in a form of its reactive derivative at the hydroxy group, and in such a case, this reaction is usually carried out in the presence of an organic or inorganic base such as those exemplified in the explanation of Process 1.

In case that suitable example of compound (V) may be thio (lower) alkanoic S-acid or thioarenoic S-acid, this reaction is preferably carried out in the presence of a conventional condensing agent such as combination of triarylphosphine (e.g. triphenylphosphine, etc.) and di(lower) alkyl azodicarboxylate (e.g. diethyl azodicarboxylate, etc.).

This reaction is usually carried out in a conventional solvent which does not adversely influence the reaction such as dichloromethane, methanol, ethanol, propanol, pyridine, N,N-dimethylformamide, tetrahydrofuran, etc., or a mixture thereof.

The reaction temperature is not critical and the reaction is usually carried out under from cooling to warming.

In this method, the configuration on the carbon atom substituted with the hydroxy group of the compound (IV) is inverted in the compound (III-a).

(B) Method B

The compound (III) or salts thereof can be prepared by subjecting the compound (III-a) or salts thereof to elimination reaction of the mercapto-protective group.

This elimination reaction can be carried out by a conventional method as described below, which can be selected according to the kind of mercapto-protective group to be eliminated.

In case that the protective groups may be ar(lower)alkyl group, it can generally be eliminated by treating, for example, with a silver compound (e.g. silver nitrate, silver carbonate, etc.).

The reaction with the silver compound as stated above is preferably carried out in the presence of an organic base (e.g. pyridine, etc.).

The resultant silver salt of compound (III) can be transformed into its alkali metal salt, if necessary, by reacting with alkali metal halide (e.g. sodium iodide, potassium iodide, etc.).

Further, in case that the protective groups may be acyl group, it can generally be eliminated by solvolysis such as hydrolysis using an acid or base, alcoholysis using a base, and the like.

Suitable acid or base used in these reactions may be the same such as those given in the explanation of hydrolysis of the Process 2.

The hydrolysis is usually carried out in a conventional solvent which does not adversely influence the reaction such as water, alcohol (e.g. methanol, ethanol, etc.), pyridine, N,N-dimethylformamide, etc., or a mixture thereof, and further in case that the base or acid to be used is in liquid, it can also be used as a solvent.

The alcoholysis is usually carried out in a conventional alcohol such as methanol, ethanol, and the like.

The reaction temperature is not critical and the reaction is usually carried out under from cooling to warming.

(C) Method C

[Step ①]

The compound (III-b) or salts thereof can be prepared by reacting the compound (VI) or salts thereof with hydrogen azide or salts thereof.

Suitable salts of the compounds (III-b) and (VI) may be the same as those for the compound (V).

Suitable salts of hydrogen azide may be alkali metal salt such as sodium salt and potassium salt.

This reaction is usually carried out in a conventional solvent which does not adversely influence the reaction such as N,N-dimethylformamide, and the like.

The reaction temperature is not critical and the reaction is usually carried out under from warming to heating.

[Step ②]

The compound (III-c) or salts thereof can be prepared by lower alkylating the compound (III-b) or salts thereof.

Suitable salts of the compound (III-c) may be the same as those for the compound (III-b).

The lower alkylating agent used in this reaction is a conventional one which is capable of lower alkylating a tetrazolyl group such as lower alkyl halide (e.g. methyl iodide, etc.), and the like.

This reaction can be carried out in the presence of a base as exemplified in Process 1.

The reaction temperature is not critical and the reaction is usually carried out under from cooling to warming.

(D) Method D

The compound (III-d) or salts thereof can be prepared by subjecting the compound (VII) or salts thereof to acetal or thioacetal formation reaction.

Suitable salts of the compound (III-d) may be the same as those for the compound (I).

Suitable salts of the compound (VII) may be the same as those for the compound (III-b).

The acetal or thioacetal forming agent used in this reaction may be optionally substituted 1,2-ethanediol or 1,3-propanediol, or optionally substituted 1,2-ethanedithiol or 1,3-propanedithiol.

This reaction can also be carried out in the presence of an acid such as toluenesulfonic acid and boron trifluoride etherate, and the like.

Further, this reaction is usually carried out in a conventional solvent which does not adversely influence the reaction such as benzene, toluene, dichloromethane, and the like.

The reaction temperature is not critical and the reaction is usually carried out at room temperature to under heating.

(E) Method E

The compound (III-f) can be prepared by subjecting the compound (III-e) to azidation.

Suitable salts of the compounds (III-e) and (III-f) may be the same as those for the compound (III-b).

The azidating agent used in this reaction is hydrogen azide or its alkali metal salts as explained in Method C.

This reaction is usually carried out in a conventional solvent which does not adversely influence the reaction such as N,N-dimethylformamide, and the like.

The reaction temperature is not critical and the reaction is usually carried out at room temperature to under heating.

The object compounds (I), (I-b), (I-d), (I-f), (I-h), (I-j) and (I-l), and the compounds (III) and (III-a) to (III-f) obtained according to the Processes 1 to 7, and Methods A to E as explained above can be isolated and purified in a conventional manner, for example, extraction, precipitation, fractional crystallization, recrystallization, chromatography, and the like.

The object compounds (I) and the pharmaceutically acceptable salts thereof of the present invention are novel and exhibit high antimicrobial activity, inhibiting the growth of a wide variety of pathogenic microorganisms, and further, are very stable against Dehydropeptidase and show high urinary excretion, therefore have high potential for the treatment of various infectious diseases.

In the present invention, the object compounds (I) possessing more potent antimicrobial activity can be represented by the following formula:

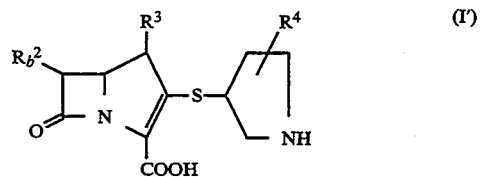

in which $R_b^2$, $R^3$ and $R^4$ are each as defined above, and pharmaceutically acceptable salts thereof.

Particularly, the compounds (I) possessing the most potent antimicrobial activity can be represented by the following formula:

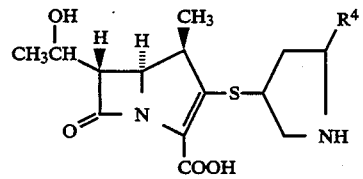

in which $R^4$ are each as defined above, and pharmaceutically acceptable salts thereof.

Now, in order to show the utility of the object compounds (I), the test data on antimicrobial activity of the representative compound of the object compounds (I) of this invention is shown in the following.

in vitro Antimicrobial Activity

Test Compound (4R,5S,6S )-6-[(1R) -1-Hydroxyethyl]-4-methyl-7-oxo-3-[(2S,4S)-2-(1H-1,2,4-triazol-3-yl) pyrrolidin-4-ylthio]-1-azabicyclo [3.2.0]hept-2-ene-2-carboxylic acid Test Method in vitro Antimicrobial Activity was determined by the two-fold agar-plate dilution method as described below.

One loopful of an overnight culture of each test strain in Trypticase-soy broth ($10^6$ viable cells per ml) was streaked on heart infusion agar (HI-agar) containing graded concentrations of the test compound, and the minimal inhibitory concentration (MIC) was expressed in terms of ug/ml after incubation at 37° C. for 20 hours.

| Test Result: | |
|---|---|
| Test Strains | MIC (μg/ml) |
| Proteus vulgaris 49 | 0.05 |

For therapeutic administration, the object compounds (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compounds (I) may vary from and also depend upon the age, conditions of the patient, a kind of diseases, a kind of the compounds (I) to be applied, etc. In general, amount between 1 mg and about 4,000 mg or even more per day may be administered to a patient. An average single dose of about 1 mg, 10 mg, 50 mg, 100 mg, 250 mg, 500 mg, 1000 mg, 2000 mg of the object compounds (I) of the present invention may be used in treating infectious diseases caused by pathogenic microorganisms.

The following Preparations and Examples are given for the purpose of illustrating this invention in more detail.

Preparation 1

To a solution of (2S, 4K) -2-acetyl-4-methanesulfonyl-oxy-1-(4-nitrobenzyloxycarbonyl) pyrrolidine (2.5 g) in tetrahydrofuran (80 ml) was added pyridinium bromide perbromide (2.59 g) at 5°–10° C. After stirring at room temperature for 3 hours, the mixture was poured into water (80 ml) and ethyl acetate (160 ml). The separated organic layer was washed with 1N hydrochloric acid, saturated aqueous sodium bicarbonate and brine successively, dried over magnesium sulfate, and evaporated in vacuo. The oily residue was subjected to a column chromatography on silica gel (60 g) eluting with a mixture of acetone and dichloromethane (1:20 V/V) to give (2S, 4R)-2-bromoacetyl-4-methanesulfonyloxy-1-(4-nitrobenzyloxycarbonyl) pyrrolidine (2.98 g).

mp: 52°–55 ° C.

IR (Nujol): 1730, 1705, 1610, 1520 cm$^{-1}$

NMR (CDCl$_3$, δ): 2.1–2.9 (2H, m), 3.08 (3H, s), 3.29–4.31 (4H, m), 4.87 (1H, t, J=7.5 Hz), 5.1–5.5 (3H, m), 7.33–7.61 (2H, m), 8.25 (2H, d, J=9 Hz)

Preparation 2

To a solution of ( 2S, 4R) -2-carbamoyl-4-methanesulfonyloxy-1- (4-nitrobenzyloxycarbonyl)pyrrolidine (7 g) in tetrahydrofuran (210 ml) was added 2,4-bis(4-methoxyphenyl) -1, 3-dithia-2,4-diphosphetane-2,4-disulfide (3.65 g) and the solution was stirred for 2 hours under refluxing. After the solvent was removed, the resulting oily residue was subjected to a column chromatography on silica gel (150 g) eluting with a mixture of n-hexane and ethyl acetate (2:3 V/V) to give ( 2S, 4R) -4-methanesulfonyloxy-1-(4-nitrobenzyloxycarbonyl) -2-thiocarbamoylpyrrolidine (5.55 g).

mp: 123°–124° C.

IR (Neat): 3200, 3400, 1690, 1740, 1600, 1535 cm$^{-1}$

NMR (CDCl$_3$, d): 2.5–3.0 (2H, m), 3.08 (3H, s), 4.7–5.1 (1H, m), 5.2–5.5 (3H, m), 7.51 (2H, d, J=9 Hz), 8.23 (2H, d, J=9 Hz)

Preparation 3-1)

To a solution of (2S, 4R) -2-bromoacetyl-4-methanesulfonyloxy-1- (4-nitrobenzyloxycarbonyl)pyrrolidine (660 mg) in a mixture of methanol (20 ml) and dichloromethane (20 ml) was added thiourea (165 mg) at room temperature. After stirring at the same temperature for 3 hours, the mixture was poured into ethyl acetate, washed in turn with saturated aqueous sodium bicarbonate and brine. The dried organic layer was evaporated, and the resulting oil was crystallized from a mixture of n-hexane and methanol (100:1 V/V) to give (2S, 4R)-2-(2-aminothiazol-4-yl)-4-methane-sulfonyloxy-1-(4-nitrobenzyloxycarbonyl)pyrrolidine (550 mg).

mp: 186°–189 ° C.

IR (Nujol): 3380, 3500, 1690, 1610, 1520 cm$^{-1}$

NMR (DMSO-d$_6$, δ) : 3.31 (3H, s), 3.5–4.1 (2H, m), 4.6–5.0 (1H, m), 5.0–5.6 (3H, m), 6.40 (1H, s) , 7.00 (2H, m) , 7.2–7.8 (2H, m), 8.1–8.4 (2H, m)

Preparation 3-2)

To a solution of (2S, 4R) -2-bromoacetyl-4-methanesulfonyloxy-1- (4-nitrobenzyloxycarbonyl)pyrrolidine (1.15 g) in a mixture of methanol (20 ml) and dichloromethane (15 ml) was added thioacetamide (308 mg) at room temperature. After stirring at the same temperature for 4 hours, the mixture was poured into ethyl acetate and washed in turn with saturated aqueous sodium bicarbonate and brine. The dried organic layer was evaporated and the resulting oil was subjected to a column chromatography on silica gel (50 g) eluting with a mixture of acetone and dichloromethane (1:20 V/V) to give (2S, 4R)-4-methanesulfonyloxy-2-(2-methylthiazol-4-yl)-1- (4-nitrobenzyloxycarbonyl)pyrrolidine (810 mg).

mp: 135°–139° C.

Mass: 441 (M+)

IR (Neat): 3400–3600, 1710, 1610, 1525 cm$^{-1}$

NMR (CDCl$_3$, δ): 2.62 (3H, s), 2.1–2.8 (2H, m), 3.03 (3H, s) , 3.9–4.1 (2H, m), 5.1–5.6 (4H, m), 6.7–7.7 (3H, m), 8.0–8.4 (2H, m)

Preparation 3-3)

To a mixture of (2S, 4R)-2-bromoacetyl-4-methanesulfonyloxy-1- (4-nitrobenzyloxycarbonyl)pyrrolidine(1.15 g) in a mixture of methanol (20 ml) and dichloromethane (15 ml) was added thioformamide (453 mg) at room temperature. After stirring at the same temperature for 4 hours, the mixture was poured into ethyl acetate and washed in turn with saturated aqueous sodium bicarbonate and brine. The dried organic layer was evaporated and the resulting oil was crystallized from a mixture of n-hexane and dichloromethane (100:1 V/V) to give (2S, 4R) -4-methanesulfonyloxy-2-(thiazol-4-yl)-1- (4-nitrobenzyloxycarbonyl)pyrrolidine (930 mg).

mp: 117°–119° C.

IR (Nujol): 1695, 1610, 1520 cm$^{-1}$

NMR (CDCl$_3$, δ): 2.4–2.7 (2H, m), 3.01 (3H, s), 3.8–4.2 (2H, m), 5.0–5.7 (4H, m), 7.0–7.7 (3H, m), 8.0–8.3 (2H, m), 6.79 (1H, d, J=2 Hz)

Preparation 3-4)

To a solution of (2S, 4R) -2-bromoacetyl-4-methanesulfonyloxy-1- (4-nitrobenzyloxycarbonyl)pyrrolidine (840 mg) in a mixture of methanol (30 ml) and dichloromethane (20 ml) was added 2-(4-nitrobenzyloxycarbonylamino)thioacetamide (700 mg) at room temperature. After stirring at 60° C. for 2 hours, the mixture was poured into ethyl acetate and washed with saturated aqueous sodium bicarbonate and brine successively. The dried organic layer was evaporated and the resulting oil was subjected to a column chromatography on silica gel (30 g) eluting with ethyl acetate to give (2S, 4R) -4-methanesulfonyloxy-1-(4-nitrobenzyloxycarbonyl) -2- [2-{N-(4-nitrobenzyloxycarbonyl)aminomethyl}-thiazol-4-yl]pyrrolidine (540 mg).

IR (Neat): 3350, 1690–1740, 1610, 1520 cm$^{-1}$

NMR (CDCl$_3$-DMSO-d$_6$, δ) : 3.01 (3H, s), 3.6–4.2 (2H, m), 4.61 (3H, d, J=6 Hz), 4.9–5.6 (5H, m), 5.7–6.1 (1H, m), 6.9–7.3 (1H, m), 7.3–7.7 (4H, m), 8.0–8.3 (4H, m)

Preparation 4

To (2S, 4R) -2-carbamoyl-4-methanesulfonyloxy-1-(4-nitrobenzyloxycarbonyl)pyrrolidine (3 g) was added N,N-dimethylformamide dimethylacetal (3 ml) and the mixture was stirred at 120° C. for 1 hour. The mixture was poured into a mixture of ethyl acetate and dichloromethane, washed with water and brine successively, and evaporated in vacuo to give (2S,4R)-4-methanesulfonyloxy-2- [N-(N,N-dimethylaminomethylene) carbamoyl]-1-(4-nitrobenzyloxycarbonyl) pyrrolidine. The compound obtained above was dissolved in acetic acid (30 ml) and to this solution was added hydrazine hydrate (0.36 ml) at room temperature. After stirring at the same temperature for 2 hours, the mixture was poured into water and ethyl acetate. The organic layer was washed with saturated aqueous sodium bicarbonate and brine successively, dried over magnesiumسsulfate, and evaporated in vacuo. The oily residue was subjected to a column chromatography on silica gel (90 g) eluting with a mixture of methanol and dichloromethane (1:20 V/V) to give (2S,4R) -4-methanesulfonyloxy-1-(4-nitrobenzyloxycarbonyl) -2-(1H-1,2,4-triazol-3-yl)pyrrolidine (1.5 g).

IR (CHCl$_3$): 1710, 1610, 1520 cm$^{-1}$

NMR (CDCl$_3$-DMSO-d$_6$, d): 3.09 (3H, s), 4.00 (2H, m), 5.0–5.6 (4H, m), 7.2–7.7 (2H, m), 8.0–8.4 (3H, m)

Preparation 5

To (2S, 4R) -4-methanesulfonyloxy-1-(4-nitrobenzyloxy-carbonyl)-2-thiocarbamoylpyrrolidine (1.5 g) was added N,N-dimethylformamide dimethylacetal (1.5 ml) and the mixture was stirred at room temperature for 1.5 hours. After the solvent was removed, the residue was dissolved in dichloromethane (30 ml). To the solution was added dropwise O-(mesitylenesulfonyl)hydroxylamine (1.5 g) in dichloromethane (20 ml) at 0° C. After stirring at room temperature for 2 hours, the mixture was washed with saturated aqueous sodium bicarbonate and brine successively. The dried organic layer was evaporated and the residue was subjected to a column chromatography on silica gel (30 g) eluting with a mixture of n-hexane and ethyl acetate (1:2 V/V) to give (2S, 4R) -4-methanesulfonyloxy-1-(4-nitrobenzyloxycarbonyl) -2- (1,2,4-thiadiazol-5-yl) pyrrolidine (850 mg).

IR (CHCl$_3$): 1705, 1605, 1510 cm$^{-1}$

NMR (CDCl$_3$, δ): 2.6–3.0 (2H, m), 3.09 (3H, s), 5.1–5.6 (3H, m), 5.68 (1H, t, J=6 Hz), 7.2–7.7 (2H, m), 8.0–8.3 (2H, d, J=6 Hz), 8.62 (1H, s)

Preparation 6-1)

To a suspension of sodium hydride (62.8% dispersion in mineral oil, 285 mg) in N,N-dimethylformamide (30 ml) was added thioacetic S-acid (0.54 ml) at 0°–5° C. under an atmosphere of nitrogen. After evolution of hydrogen ceased, the mixture was stirred at room temperature, and (2S, 4R) -2-(2-aminothiazol-4-yl)-4-methanesulfonyloxy-1-(4-nitrobenzyloxycarbonyl) pyrrolidine (1.6 g) in N,N-dimethylformamide (20 ml) was added thereto. The mixture was stirred at 90° C. for 5 hours and poured into a mixture of ethyl acetate (100 ml) and water (100 ml). The aqueous layer was separated and extracted twice with ethyl acetate (50 ml). The organic layers were combined, washed with brine, dried over magnesium sulfate and concentrated under reduced pressure to give a syrup. The syrup was subjected to a column chromatography on silica gel (60 g) eluting with a mixture of acetone and dichloromethane (1:5 V/V) to give (2S, 4S)-4-acetylthio-2-(2-aminothiazol-4-yl)-1-(4-nitrobenzyloxycarbonyl) pyrrolidine (1.26 g).

IR (Neat): 3100–3500, 1650–1720, 1520 cm$^{-1}$

NMR (CDCl$_3$, δ): 2.0–2.9 (2H, m), 2.29 (3H, s), 3.2–4.3 (3H, m), 4.86 (1H, t, J=7 Hz), 4.9–5.5 (4H, m), 6.22 (1H, br s), 7.2–7.7 (2H, m), 8.0–8.3 (2H, m)

Preparation 6-2)

(2S, 4S )-4-Acetylthio-2-(2-methylthiazol-4-yl)-1-(4-nitrobenzyloxycarbonyl) pyrrolidine (630 mg) was obtained by reacting (2S, 4R)-4-methanesulfonyloxy-2-(2-methylthiazol-4-yl)-1- (4-nitrobenzyloxycarbonyl)pyrrolidine (800 mg) with thioacetic S-acid (0.26 ml) in substantially the same manner as that of Preparation 6-1).

IR (Neat): 1680–1720, 1610, 1520 cm$^{-1}$

NMR (CDCl$_3$, δ): 2.31 (3H, s), 2.69 (3H, s), 3.3–3.7 (1H, m), 3.9–4.4 (2H, m), 4.9–5.4 (3H, m), 6.88 (1H, br s), 7.0–7.7 (2H, m), 8.0–8.3 (2H, m)

Preparation 6-3)

(2S, 4S)-4-Acetylthio-2-(thiazol-4-yl)-1-(4-nitrobenzyloxycarbonyl) pyrrolidine (856 mg) was obtained by reacting (2S, 4R)-4-methanesulfonyloxy-2-(thiazol-4-yl)-1-(4-nitrobenzyloxycarbonyl) pyrrolidine (920 mg) with thioacetic S-acid (0.30 ml) in substantially the same manner as that of Preparation 6-1).

IR (Neat): 1670–1720, 1610, 1520 cm$^{-1}$

NMR (CDCl$_3$, δ): 2.30 (3H, s), 3.3–3.7 (1H, m), 3.8–4.4 (2H, m), 5.0–5.4 (3H, m), 7.0–7.7 (3H, m), 7.9–8.4 (2H, m), 8.79 (1H, d, J=2 Hz)

Preparation 6-4)

(2S, 4S)-4-Acetylthio-1-(4-nitrobenzyloxycarbonyl)-2-[2-{N-(4-nitrobenzyloxycarbonyl)aminomethyl}thiazol-4-yl]pyrrolidine (460 mg) was obtained by reacting (2S,4R)-4-methanesulfonyloxy-1-(4-nitrobenzyloxycarbonyl)-2-[2-{N-(4-nitrobenzyloxycarbonyl)aminomethyl}thiazol-4-yl]pyrrolidine (540 mg) with thioacetic S-acid (0.26 ml) in substantially the same manner as that of Preparation 6-1).

IR (Neat): 3350, 1680–1740, 1610, 1510–1520 cm$^{-1}$
NMR (CDCl$_3$, δ): 2.29 (3H, s), 3.2–3.7 (1H, m), 3.8–4.3 (2H, m), 4.67 (2H, d, J=6 Hz), 4.9–5.4 (4H, m), 5.4–5.8 (1H, m), 6.9–7.7 (3H, m), 8.1–8.4 (2H, m)

Preparation 6-5)

(2S, 4S) -4-Acetylthio-1-(4-nitrobenzyloxycarbonyl)-2-(1H-1, 2,4-triazol-3-yl)pyrrolidine (1.14 g) was obtained by reacting (2S, 4R) -4-methanesulfonyloxy-1-(4-nitrobenzyloxycarbonyl)-2-(1H-1,2,4-triazol-5-yl)pyrrolidine (1.5 g) with thioacetic S-acid (0.52 ml) in substantially the same manner as that of Preparation 6-1).

IR (Neat): 1660–1730, 1610, 1525 cm$^{-1}$
NMR (CDCl$_3$, d): 2.30 (3H, s), 3.3–3.7 (1H, m), 3.8–4.4 (2H, m), 5.1–5.4 (3H, m), 7.2–7.7 (2H, m), 7.9–8.4 (3H, m)

Preparation 6-6)

(2S, 4S) -4-Acetylthio-1-(4-nitrobenzyloxycarbonyl)-2-(1, 2,4-thiadiazol-5-yl) pyrrolidine (580 mg) was obtained by reacting (2S, 4R) -4-methanesulfonyloxy-1-(4-nitrobenzyloxycarbonyl) -2-(1,2,4-thiadiazol-5-yl)pyrrolidine (850 mg) with thioacetic S-acid (0.28 ml) in substantially the same manner as that of Preparation 6-1).

IR (CH$_2$Cl$_2$): 1700, 1605, 1520 cm$^{-1}$
NMR (CDCl$_3$, δ): 2.27 (3H, s), 3.3–3.7 (1H, m), 3.9–4.4 (2H, m), 5.23 (2H, br s), 5.41 (1H, dd, J=5, 8 Hz), 7.3–7.7 (2H, m), 8.1–8.4 (2H, m), 8.60 (1H, s)

Preparation 7-1)

To a solution of (2S, 4S) -4-acetylthio-2-(2-aminothiazol-4-yl) -1-(4-nitrobenzyloxycarbonyl)pyrrolidine (1.26 g) in a mixture of methanol (20 ml) and dichloromethane (10 ml) was added sodium methoxide (28% solution in methanol, 1.2 ml) at −30° to −20° C. under an atmosphere of nitrogen. After stirring at 0° C. for 1 hour, acetic acid (0.36 ml) was added to the mixture. The solution was evaporated under reduced pressure, then the residue was dissolved in ethyl acetate, and washed with water, saturated aqueous sodium bicarbonate and brine successively. The dried organic layer was evaporated to give (2S ,4S)-2- (2-aminothiazol-4-yl)-4-mercapto-1-(4-nitrobenzyloxycarbonyl) pyrrolidine (1.13 g)

IR (Neat): 3100–3500, 1680–1750, 1610, 1520 cm$^{-1}$
NMR (CDCl$_3$, δ): 1.5–3.0 (3H, m), 3.2–4.0 (2H, m), 4.78 (1H, t, J=7 Hz), 4.8–5.5 (4H, m), 6.22 (1H, br s), 7.1–7.7 (2H, m), 8.0–8.4 (2H, m)

Preparation 7-2)

(2S, 4S)-4-Mercapto-2-(2-methylthiazol-4-yl)-1-(4-nitrobenzyloxycarbonyl) pyrrolidine (566 mg) was obtained by reacting (2S, 4S )-4-acetylthio-2-(2-methylthiazol-4-yl)-1-(4-nitrobenzyloxycarbonyl) pyrrolidine (630 mg) with sodium methoxide (28% solution in methanol, 0.6 ml) in substantially the same manner as that of Preparation 7-1).

IR (CHCl$_3$): 1710, 1610, 1520 cm$^{-1}$
NMR (CDCl$_3$, δ): 2.70 (3H, s), 3.0–4.3 (3H, m), 4.9–5.4 (3H, m), 6.89 (1H, m), 7.0–7.8 (2H, m), 8.0–8.3 (2H, m)

Preparation 7-3)

(2S, 4S )-4-Mercapto-1-(4-nitrobenzyloxycarbonyl)-2-(thiazol-4-yl) pyrrolidine (700 mg) was obtained by reacting (2S, 4S)-4-acetylthio-1-(4-nitrobenzyloxycarbonyl) -2-(thiazol-4-yl) pyrrolidine (850 mg) with sodium methoxide (28% solution in methanol, 0.9 ml) in substantially the same manner as that of Preparation 7-1).

IR (Neat): 1680–1740, 1610, 1520–1540 cm$^{-1}$
NMR (CDCl$_3$, δ): 3.2–3.9 (2H, m), 3.9–4.4 (1H, m), 4.9–5.4 (3H, m), 7.0–7.7 (3H, m), 8.0–8.4 (2H, m), 8.81 (1H, d, J=2 Hz)

Preparation 7-4)

(2S, 4S)-4-Mercapto-1-(4-nitrobenzyloxycarbonyl)-2-[2-{N-(4-nitrobenzyloxycarbonyl) aminomethyl} thiazol-4-yl]pyrrolidine (500 mg) was obtained by reacting (2S,4S)- 4-acetylthio-1-(4-nitrobenzyloxycarbonyl)-2-[2-{N-(4-nitrobenzyloxycarbonyl) aminomethyl} thiazol-4-yl]-pyrrolidine (460 mg) with sodium methoxide (28% solution in methanol, 0.4 ml) in substantially the same manner as that of Preparation 7-1).

IR (Neat): 3300, 1630–1740, 1610, 1510–1530 cm$^{-1}$
NMR (CDCl$_3$, δ): 3.2–4.3 (3H, m), 4.68 (2H, d, J=6 Hz), 4.9–5.4 (4H, m), 5.4–5.7 (1H, m), 6.9–7.7 (3H, m), 8.0–8.4 (2H, m)

Preparation 7-5)

(2S, 4S )-4-Mercapto-1-(4-nitrobenzyloxycarbonyl)-2-(1H-1,2,4-triazol-3-yl) pyrrolidine (1.06 g) was obtained by reacting (2S ,4S) -4-acetylthio-1-(4-nitrobenzyloxycarbonyl) -2-(1H-1,2,4 -triazol-3-yl)pyrrolidine (1.14 g) with sodium methoxide (28% solution in methanol, 1.2 ml) in substantially the same manner as that of Preparation 7-1).

IR (Neat): 3100–3300, 1670–1730, 1610, 1525 cm$^{-1}$
NMR (CDCl$_3$, δ): 3.2–3.8 (2H, m), 3.8–4.3 (2H, m), 4.9–5.4 (3H, m), 7.2–7.7 (2H, m), 7.9–8.4 (2H, m)

Preparation 7-6)

(2S,4S) -4-Mercapto-1-(4-nitrobenzyloxycarbonyl)-2-(1,2,4-thiadiazol-5-yl) pyrrolidine (460 mg) was obtained by reacting (2S, 4S) -4-acetylthio-1-(4-nitrobenzyloxycarbonyl)-2-(1, 2,4-thiadiazol-5-yl)pyrrolidine (580 mg) with sodium methoxide (28% solution in methanol, 0.6 ml) in substantially the same manner as that of Preparation 7-1).

IR (Neat): 1700–1710, 1610, 1525 cm$^{-1}$
NMR (CDCl$_3$, δ): 3.2–3.8 (2H, m), 3.9–4.5 (2H, m), 5.21 (2H, br s), 5.34 (1H, t, J=7 Hz), 7.2–7.7 (2H, m), 8.1–8.4 (2H, m), 8.60 (1H, s)

Preparation 8

To a solution of (2S, 4R)-2-cyano-4-methanesulfonyloxy-1-(4-nitrobenzyloxycarbonyl) pyrrolidine (2 g) in tetrahydrofuran (40 ml) was added 2-aminoethanethiol (630 mg) at ambient temperature. After stirring for 24 hours at the same temperature, the mixture was evaporated. The residue was extracted with dichloromethane, washed with water and brine successively, and dried over magnesium sulfate. The organic layer was evaporated, and then the obtained oil was subjected to a column chromatography on silica gel and eluted with a mixture of dichloromethane and acetone (4:1V/V) to give (2S,4R)-4-methanesulfonyloxy-1-(4-nitrobenzyloxycarbonyl)-2-(2-thiazolin-2-yl) pyrrolidine (0.96 g).

IR (CH$_2$Cl$_2$): 1720, 1635, 1615 cm$^{-1}$
NMR (CDCl$_3$, δ): 3.06 (3H, s), 3.0–3.5 (2H, m), 3.5–4.5 (4H, m), 4.5–5.1 (1H, m), 5.1–5.4 (3H, m), 7.48 (2H, d, J=9 Hz), 8.18 (2H, d, J=9 Hz)

Preparation 9

To a mixture of dimethylformamide (2.9 ml) and tetrahydrofuran (6 ml) was dropwise added phosphorus oxychloride (2.8 ml) at −5°∫5° C. and the mixture was stirred at the same temperature for 30 minutes. To the mixture was added a solution of (2S,4R)-2- carboxy-4-methanesulfonyloxy-1-(4-nitrobenzyloxycarbonyl)pyrrolidine (9.65 g) in tetrahydrofuran (20 ml) at $-5°$ ∫ $5°$ C., followed by stirring at the same temperature for 30 minutes. The mixture was dropwise added to a solution of 4-methylthiosemicarbazide (25 g) in a mixture of water (200 ml) and tetrahydrofuran (200 ml) at 0°-10° C. with stirring, keeping the pH between 8-9 with 1N aqueous sodium hydroxide. The mixture was stirred at the same condition for 2 hours. Tetrahydrofuran was evaporated under reduced pressure to give precipitates. The precipitates were collected by filtration, washed with water and diisopropyl ether successively, and dried over phosphorus pentoxide to give (2S, 4R)-4-methanesulfonyloxy -2-(4-methylthiosemicarbazidocarbonyl)-1-(4-nitrobenzyloxycarbonyl) pyrrolidine (9.61 g).

mp: 187°-189° C.

IR (Nujol): 3300, 1700, 1675 cm$^{-1}$

NMR (DMSO-d$_6$, δ) : 2.86 (3H, d, J-3 Hz), 3.30 (3H, s)

Preparation 10

A suspension of (2S, 4R)-4-methanesulfonyloxy-2-(4-methylsemicarbazidocarbonyl)-1- (4-nitrobenzyloxycarbonyl)pyrrolidine (2.00 g) in concentrated sulfuric acid (20 ml) was stirred at 0°-5° C. for 3 hours. The reaction mixture was poured into ice-water (200 ml), adjusted to pH 9 with concentrated ammonia water, extracted with dichloromethane (100 ml), dried over magnesium sulfate and concentrated under reduced pressure to give a syrup. The syrup was subjected to a column chromatography on silica gel (20 g) and eluted with a mixture of methanol and chloroform (1:99,V/V) to give (2S, 4R)-4-methanesulfonyloxy-2-{5-(methylamino)-1,3,4-thiadiazol-2-yl }-1-(4-nitrobenzyloxycarbonyl)pyrrolidine (1.94 g).

IR (CHCl$_3$): 1707 cm$^{-1}$

NMR (CDCl$_3$, δ): 3.01 (3H, s), 3.06 (3H, s)

MS: 361 (M+-96), 304 (M+-153)

Preparation 11

(2S, 4R) -4-Butyldimethylsilyloxy-1-(4-nitrobenzyloxycarbonyl) -2-thiocarbamoylpyrrolidine (1.85 g) was obtained by reacting (2S, 4R)-4-t-butyldimethylsilyloxy-2-carbamoyl-1- (4-nitrobenzyloxycarbonyl)-pyrrolidine (2.0 g) with 2,4-bis(4-methoxyphenyl)-1,3-dithia-2,4-diphosphetane-2,4-disulfide (1.15 g) in substantially the same manner as that of Preparation 2.

IR (Neat): 3300, 1700, 1610 cm$^{-1}$

NMR (CDCl$_3$, δ): 0.98 (6H, s), 0.85 (9H, s), 2.0-2.6 (2H, m), 3.4-3.8 (2H, m) , 4.3-4.6 (1H, m) , 4.6-5.1 (1H, m) , 5.24 (2H, s), 7.49 (2H, d, J=8 Hz), 8.25 (2H, d, J=8 Hz)

Preparation 12

To a solution of (2S, 4R)-4-t-butyldimethylsilyloxy-1-(4-nitrobenzyloxycarbonyl)-2-thiocarbamoylpyrrolidine (1.5 g) in tetrahydrofuran (20 ml) was added ethylenediamine (1.25 ml) at 0° C. After stirring at room temperature for 24 hours, the mixture was evaporated, extracted with ethyl acetate, and washed with water and brine successively. The dried organic layer was evaporated, and the obtained oil was subjected to a column chromatography on silica gel and eluted with a mixture of dichloromethane, methanol and triethylamine (90:10:1, V/V/V) to give (2S,4R) -4-t-butyldimethylsilyloxy -2-(2-imidazolin-2-yl)-1-(4-nitrobenzyloxycarbonyl)pyrrolidine (1.2 g).

IR (CH$_2$Cl$_2$): 1700, 1620, 1600, 1520 cm$^{-1}$

NMR (CDCl$_3$, δ) : 0.08 (6H, s), 0.89 (9H, s), 3.6 (4H, br s), 4.3-4.9 (2H, m) , 5.2-5.4 (2H, m), 7.52 (2H, d, J=9 Hz), 8.28 (2H, d, J=9 Hz)

Preparation 13

To a solution of (2S, 4R) -4-t-butyldimethylsilyloxy-2- (2-imidoxolin-2-yl)-1-(4-nitrobenzyloxycarbonyl)pyrrolidine (930 mg) in tetrahydrofuran (20 ml) was added sodium hydride (62.8% suspension in oil, 103 mg), and to this mixture was dropwise added a solution of 4-nitrobenzyloxycarbonyl chloride (531 mg) in dichloromethane (15 ml) at 0° C. After stirring at 0° C. for 1.5 hours, acetic acid (0.18 ml) was added thereto. The mixture was evaporated, extracted with ethyl acetate, and washed with saturated sodium bicarbonate and brine successively. The dried organic layer was evaporated, the obtained oil was subjected to a column chromatography on silica gel and eluted with a mixture of dichloromethane and acetone (9:1, V/V) to give (2S, 4R) -4-t-butyldimethylsilyloxy-1-(4-nitrobenzyloxycarbonyl) -2-[1-(4-nitrobenzyloxycarbonyl)-2-imidazolin-2-yl]pyrrolidine (1.4 g).

IR (Neat): 1700-1720, 1645, 1610 cm$^{-1}$

NMR (CDCl$_3$, δ): 0.02 (6H, s), 0.82 (9H, s), 3.6-4.0 (4H, m), 5.0-5.5 (5H, m), 7.51 (4H, m), 8.28 (4H, m)

Preparation 14

To a solution of (2S, 4R)-4-t-butyldimethylsilyloxy-1-(4-nitrobenzyloxycarbonyl)-2-[1-(4-nitrobenzyloxycarbonyl) -2-imidazolin-2-yl]pyrrolidine (1.4 g) in methanol was added conc. hydrochloric acid (0.4 ml). After stirring at ambient temperature for 20 hours, saturated aqueous sodium bicarbonate (3 ml) was added thereto. The mixture was evaporated, extracted with ethyl acetate, and washed with water and brine successively. The dried organic layer was evaporated, the obtained oil was subjected to a column chromatography on silica gel and eluted with a mixture of dichloromethane and methanol (20:1, V/V) to give (2S,4R)-4- hydroxy-1-(4-nitrobenzyloxycarbonyl)-2-[1-(4-nitrobenzyloxycarbonyl) -2-imidazolin-2-yl]pyrrolidine (660 mg).

mp: 55°-62° C.

IR (CH$_2$Cl$_2$): 1710, 1640, 1610 cm$^{-1}$

NMR (CDCl$_3$, δ) : 3.5-4.0 (6H, m), 4.4-4.7 (1H, m), 5.1-5.4 (4H, m), 5.5 (1H, t, J=7 Hz), 7.3-7.8 (4H, m) , 8.1-8.4 (4H, m)

Preparation 15

To a mixture of 4-hydroxymethyl-2,2-dimethyl-1,3-dioxolane (5.35 g) and pyridine (15.65 g) in dichloromethane (200 ml) was added acetic anhydride (20.56 g), and the mixture was stirred at ambient temperature for 12 hours. The mixture was poured into a mixture of water and ethyl acetate. The organic layer was separated, washed with saturated aqueous sodium hydrogen carbonate and brine successively, dried over magnesium sulfate, and evaporated in vacuo to give 4-acetoxymethyl-2,2-dimethyl-1,3-dioxolane (6.02 g).

NMR (CDCl$_3$, δ) : 1.39 (3H, s), 1.44 (3H, s), 2.10 (3H, s), 3.57-4.50 (5H, m)

Preparation 16

To a stirred solution of L-serine (3.5 g) and sodium hydrogen carbonate (7.5 g) in water (46 ml) was added 4-nitrobenzyloxycarbonyl chloride (6.4 g) in diethyl ether (10 ml) at ambient temperature. After stirring for 2 hours, to the solution were added 4-nitrobenzyloxycarbonyl chloride (6.4 g) in diethyl ether (10 ml), and sodium hydrogen carbonate (3.6 g). After stirring for 3 hours, the aqueous layer was separated and washed with ethyl acetate. After adjusting the pH to 2 with concentrated hydrochloric acid, the aqueous solution was extracted twice with ethyl acetate, dried over magnesium sulfate and evaporated. To the residue were added methanol (40 ml) and concentrated sulfuric acid (0.7 ml), and the solution was stirred at 50°–55° C. for 2.5 hours. To the mixture was added triethylamine (4.2 ml) and the mixture was evaporated in vacuo. The resulting residue was poured into a mixture of ethyl acetate and water. The organic layer was separated, washed twice with brine, dried over magnesium sulfate and evaporated. The residue was chromatographed on silica gel (300 ml) and eluted with a mixture of acetone and dichloromethane (8:92, V/V) to give methyl (2S)-3-hydroxy-2-[(4-nitrobenzyloxycarbonyl)amino]propionate (2.14 g).

NMR (DMSO-d$_6$, δ): 3.66 (3H, s) , 3.70 (2H, t, J=6 Hz), 4.03–4.40 (1H, m), 4.97 (1H, t, J=6 Hz), 5.23 (2H, s), 7.66 (2H, d, J=8 Hz) , 8.25 (2H, d, J=8 Hz)

Preparation 17

To a solution of methyl (2S)-3-hydroxy-2-[(4-nitrobenzyloxycarbonyl)amino]propionate (2.12 g) in tetrahydrofuran (20 ml) and ethanol (20 ml) was added sodium borohydride (0.54 g) at 0° C. under nitrogen atmosphere. After stirring at 0° C. for 5 hours, to the mixture was added a mixture of concentrated hydrochloric acid (1.7 ml), water (40 ml) and ethyl acetate (40 ml). The organic layer was separated, washed with 10% aqueous sodium hydrogen carbonate and brine successively, dried over magnesium sulfate, and evaporated. The residue was chromatographed on silica gel (160 ml) eluting with a mixture of acetone and dichloromethane (1:9, V/V) to give 2-[(4-nitrobenzyloxycarbonyl)amino]-1,3-propanediol (1.32 g).

NMR (DMSO-d$_6$, δ): 3.27–3.60 (5H, m) , 4.43–4.70 (2H, m), 5.20 (2H, s), 7.63 (2H, d, J=9 Hz), 8.32 (2H, d, J=9 Hz)

Preparation 18

To a suspension of (2S ,4S)-4-acetylthio-2-cyano-1-(4-nitrobenzyloxycarbonyl) pyrrolidine (2.60 g) in a mixture of methanol (26 ml) and tetrahydrofuran (52 ml) was added a 28% solution of sodium methoxide in methanol (1.8 ml) at −10° ʃ −5° C. and the mixture was stirred at the same temperature for 30 minutes. To the mixture was added trityl chloride (2.20 g) at −10° ʃ −5° C., followed by stirring at the same temperature for 1 hour. The mixture was concentrated under reduced pressure to give a residue. The residue was dissolved in ethyl acetate, washed with water, dried over magnesium sulfate and concentrated under reduced pressure to give a syrup. The syrup was subjected to a column chromatography on silica gel (40 g) and eluted with dichloromethane to give (2S,4S)-2-cyano-1-(4-nitrobenzyloxycarbonyl) -4-tritylthiopyrrolidine (2.45 g).

IR (Nujol): 1710 cm$^{-1}$

NMR (CDCl$_3$, δ): 4.27 (1H, t, J=15 Hz), 5.51 (2H, s), 8.24 (2H, d, J=8.5 Hz)

Preparation 19

A mixture of (2S, 4S)-2-cyano-1-(4-nitrobenzyloxycarbonyl)-4-tritylthiopyrrolidine (2.00 g) and sodium azide (0.30 g) in dimethylformamide (20 ml) was stirred at 110°–120° C. for 9 hours in the presence of ammonium chloride (0.05 g). The mixture was concentrated under reduced pressure to give a residue. The residue was subjected to a column chromatography on silica gel (20 g) and eluted with a mixture of acetone and chloroform (10:90, V/V) to give (2S,4S)-1-(4-nitrobenzyloxycarbonyl) -2-(1H-tetrazol-5-yl)-4-tritylthiopyrrolidine (1.86 g).

IR (Neat): 1705, 1675–1655 cm$^{-1}$

NMR (CDCl$_3$, δ): 5.00 (2H, s)

Preparation 20

A mixture of (2S, 4S)-1-(4-nitrobenzyloxycarbonyl)-2- (1H-tetrazol-5-yl)-4-tritylthiopyrrolidine (1.75 g), methyl iodide (0.25 ml) and potassium butoxide (0.36 g) was stirred at ambient temperature for 18 hours. The mixture was poured into water (50 ml) and extracted with ethyl acetate (50 ml). The organic layer was dried over magnesium sulfate and concentrated under reduced pressure to give a syrup. The syrup was subjected to a column chromatography on silica gel (20 g) and eluted with chloroform to give a mixture of (2S, 4S )-2-(1-methyl-1H-tetrazol-5-yl)-1-(4-nitrobenzyloxycarbonyl) -4-tritylthiopyrrolidine and (2S, 4S)-2-(2-methyl-2H-tetrazol-5-yl) -1-(4-nitrobenzyloxycarbonyl)-4-tritylthiopyrrolidine (1.33 g).

mp: 62°–66 ° C.

IR (Nujol): 1705 cm$^{-1}$

Preparation 21-1)

(2S, 4S)-4-Acetylthio-1-(4-nitrobenzyloxycarbonyl)-2- (2-thiazolin-2-yl)pyrrolidine (996 mg) was obtained by reacting (2S, 4R)-4-methanesulfonyloxy-1-(4-nitrobenzyloxycarbonyl) -2-(2-thiazolin-2-yl)pyrrolidine (1.28 g) with thioacetic S-acid (0.43 ml) in substantially the same manner as that of Preparation 6.

IR (CH$_2$Cl$_2$) 1720, 1630, 1610 cm$^{-1}$

NMR (CDCl$_3$, δ) : 2.32 (3H, s), 3.1–3.8 (3H, m), 3.8–4.5 (4H, m), 4.8–5.0 (1H, m), 5.1–5.4 (2H, m) , 7.52 (2H, d, J=9 Hz ), 8.29 (2H, d, J=9 Hz)

Preparation 21-2)

(2S, 4S) -4-Acetylthio-2-[5-(methylamino)-1,3, 4-thiadiazol-2-yl]-1-(4-nitrobenzyloxycarbonyl)pyrrolidine (1.10 g) was obtained by reacting (2S, 4R)-4-methanesulfonyloxy-2- [5-(methylamino)-1,3,4-thiadiazol-2-yl]-1-(4-nitrobenzyloxycarbonyl) pyrrolidine (1.92 g) in substantially the same manner as that of Preparation 6.

mp: 72°–78° C.

IR (CHCl$_3$): 1700 cm$^{-1}$

NMR (CDCl$_3$, δ): 2.32 (3H, s) , 3.01 (3H, s)

EI-MS: 436 (M+-1), 402 (M+-35), 393 (M+-44), 362 (M+-75)

Preparation 22

(2S, 4R) -4-Hydroxy-1-(4-nitrobenzyloxycarbonyl)-2- [1-(4-nitrobenzyloxycarbonyl)-2-imidazolin-2-yl]-pyrrolidine (655 mg) and triphenylphosphine (0.51 g) were dissolved in tetrahydrofuran (20 ml) at 0° C. To this solution was added dropwise a solution of diethyl azodicarboxylate (0.30 ml) in tetrahydrofuran (5 ml) with stirring for 30 minutes, followed by addition of a solution of thioacetic S-acid (0.14 ml). Stirring was continued at ambient temperature for 2 hours. The reaction mixture was diluted with ethyl acetate, washed with saturated sodium bicarbonate and brine, dried over magnesium sulfate and evaporated. The obtained oily residue was subjected to a column chromatography on silica gel and eluted with a mixture of dichloromethane and acetone (20:1, V/V) to give (2S, 4S )-4-acetylthio-1-(4-nitrobenzyloxycarbonyl)-2-[1-(4-nitrobenzyloxycarbonyl)-2-imidazolin-2 -yl]-pyrrolidine (1.2 g).

IR (CH$_2$Cl$_2$): 1690–1730, 1610 cm$^{-1}$

NMR (CDCl$_3$, δ): 2.30 (3H, s), 3.7–4.1 (4H, m), 5.0–5.5 (5H, m)

Preparation 23-1)

A solution of 4-acetoxymethyl-2,2-dimethyl-1,3-dioxolane (1.23 g) in 4N aqueous hydrochloric acid (5 ml) and tetrahydrofuran (5 ml) was stirred at ambient temperature for 14 hours, and the mixture was evaporated in vacuo. Water in the solvent was removed as the toluene azeotrope, and to the residue were added (2S, 4S)-4-acetylthio-2-formyl-1- (4-nitrobenzyloxycarbonyl)pyrrolidine (1.00 g) and 4-toluenesulfonic acid (0.20 g) in toluene. The mixture was refluxed for 3 hours with removing water under azeotropic condition to give (2S, 4S )-2-(4-acetoxymethyl-1,3-dioxolan-2-yl)-4-acetylthio1-(4-nitrobenzyloxycarbonyl) pyrrolidine (0.50 g).

IR (CH$_2$Cl$_2$): 1700 cm$^{-1}$

NMR (CDCl$_3$, δ): 1.70–2.70 (2H, m), 2.18 (3H, s), 2.34 (3H, s), 3.03 (9H, m), 4.97–5.60 (1H, m), 5.23 (2H, s), 7.53 (2H, d, J=9 Hz), 8.20 (2H, d, J=9 Hz)

Preparation 23-2)

To a solution of (2S,4S)-4-acetylthio-2-formyl-1-(4-nitrobenzyloxycarbonyl) pyrrolidine (1.00 g) and 1,2-ethanedithiol (0.36 ml) in dichloromethane (20 ml) was added boron trifluoride etherate (0.1 ml), and the solution was stirred for 14 hours at ambient temperature. To the mixture was added saturated aqueous sodium hydrogen carbonate and the organic layer was separated, and washed with brine. The organic layer was dried over magnesium sulfate and evaporated. The residue was chromatographed on silica gel (50 ml) and eluted with a mixture of acetone and dichloromethane (2:98, V/V) to give (2S, 4S)-4-acetylthio-2-(1,3-dithiolan-2-yl)-1-(4-nitrobenzyloxycarbonyl)pyrrolidine (1.14 g).

IR (CH$_2$Cl$_2$): 1715, 1705 cm$^{-1}$

NMR (CDCl$_3$, δ): 2.33 (3H, s), 1.90–4.53 (6H, m), 3.22 (4H, s), 5.20–5.53 (1H, m), 5.25 (2H, s), 7.53 (2H, d, J=9 Hz), 8.25 (2H, d, J=9 Hz)

Preparation 23-3)

(2S, 4S )-4-Acetylthio-2-(4-bromomethyl-1,3-dioxolan-2-yl) -1-(4-nitrobenzyloxycarbonyl)pyrrolidine (4.50 g) was obtained by reacting (2S,4S)-4-acetylthio-2-formyl-1- (4-nitrobenzyloxycarbonyl)pyrrolidine (3.00 g) with 3-bromo-1,2-propanediol (2.66 g) in substantially the same manner as that of Preparation 23-2).

NMR (CDCl$_3$, δ): 1.70–2.67 (2H, m), 2.32 (3H, s), 3.03–4.53 (9H, m), 5.13–5.47 (1H, m), 5.23 (2H, s), 7.53 (2H, d, J=9 Hz), 8.24 (2H, d, J=9 Hz)

Preparation 23-4)

(2S, 4S)-4-Acetylthio-2-(1,3-dioxolan-2-yl)-1-(4-nitrobenzyloxycarbonyl) pyrrolidine (1.55 g) was obtained by reacting (2S, 4S)-4-acetylthio-2-formyl-1-(4-nitrobenzyloxycarbonyl) pyrrolidine (1.50 g) with ethylene glycol (0.52 g) in substantially the same manner as that of Preparation 23-2).

IR (CH$_2$Cl$_2$): 3000–2800, 1710, 1700 cm$^{-1}$

NMR (CDCl$_3$, δ): 1.73–2.67 (2H, m), 2.65 (3H, s), 3.03–3.30 (1H, m), 3.37–4.40 (7H, m), 5.07–5.33 (1H, m), 5.23 (2H, s), 7.53 (2H, d, J=9 Hz), 8.23 (2H, d, J=9 Hz)

Preparation 23-5)

(2S, 4S)-4-Acetylthio-2-(1,3-dithian-2-yl)-1-(4-nitrobenzyloxycarbonyl) pyrrolidine (1.88 g) was obtained by reacting (2S, 4S)-4-acetylthio-2-formyl-1-(4-nitrobenzyloxycarbonyl) pyrrolidine (1.53 g) with 1,3-propanedithiol (0.97 g) in substantially the same manner as that of Preparation 23-2).

IR (CH$_2$Cl$_2$): 1705, 1700 cm$^{-1}$

NMR (CDCl$_3$, δ): 1.67–5.10 (16 H, m), 2.30 (3H, s), 5.23 (2H, s), 7.53 (2H, d, J=9 Hz), 8.21 (2H, d, J=9 Hz)

Preparation 23-6)

A solution of 2-(4-nitrobenzyloxycarbonyl)amino-1,3-propanediol (1.42 g), (2S,4S)-4-acetylthio-2-formyl-1-(4-nitrobenzyloxycarbonyl) pyrrolidine (1.00 g) and 4-toluene-sulfonic acid (0.30 g) in toluene was refluxed for 2 hours with removing water under azeotropic condition. The reaction mixture was poured into a mixture of water and ethyl acetate. The organic layer was separated, washed with brine, dried over magnesium sulfate and evaporated. The residue was chromatographed on silica gel (80 ml) and eluted with a mixture of acetone and dichloromethane (1:9, V/V) to give (2S, 4S)-4-acetylthio-1- (4-nitrobenzyloxycarbonyl)-2-[5-(4-nitrobenzyloxycarbonylamino) -1,3-dioxan-2-yl]pyrrolidine (1.47 g).

IR (CH$_2$Cl$_2$): 1720, 1700, 1605, 1520 cm$^{-1}$

NMR (CDCl$_3$, δ): 1.93–2.70 (2H, m), 2.31 (3H, s), 2.98–4.33 (8H, m), 4.78–5.33 (2H, m), 5.23 (4H, s), 7.53 (2H, d, J=6 Hz), 7.56 (2H, d, J=6 Hz), 8.92 (4H, d, J=6 Hz)

Preparation 24-1)

(2S, 4S)-4-Mercapto-1-(4-nitrobenzyloxycarbonyl)-2-(2-thiazolin-2-yl) pyrrolidine (840 mg) was obtained by reacting (2S, 4S)-4-acetylthio-1-(4-nitrobenzyloxycarbonyl) -2-(2-thiazolin-2-yl)pyrrolidine (996 mg) with 28% sodium methoxide in methanol (0.8 ml) in substantially the same manner as that of Preparation 7-1).

IR (CH$_2$Cl$_2$): 3200–3400, 1690–1720, 1625, 1605 cm$^{-1}$

NMR (CDCl$_3$, δ): 4.7–5.1 (1H, m), 5.1–5.4 (2H, m), 7.62 (2H, d, J=9 Hz), 8.30 (2H, d, J=9 Hz)

Preparation 24-2)

(2S, 4S)-4-Mercapto-2-{5-(methylamino)-1,3,4-thiadiazol-2-yl}-1-(4-nitrobenzyloxycarbonyl)pyrrolidine (0.85 g) was obtained by reacting (2S, 4S )-4-acetylthio-2-[5-(methylamino)-1,3,4-thiadiazol-2-yl]-1-(4-nitrobenzyloxycarbonyl) pyrrolidine (1.08 g) with 28% sodium methoxide in methanol in substantially the same manner as that of Preparation 7-1).

IR (CHCl$_3$): 1705 cm$^{-1}$

NMR (CDCl$_3$, δ) : 3.00 (3H, s)

MS: 395 (M+), 362 (M+-33), 318 (M+-77)

Preparation 24-3)

(2S, 4S)-4-Mercapto-1-(4-nitrobenzyloxycarbonyl)-2-[1-(4-nitrobenzyloxycarbonyl)-2-imidazolin-2-yl]-pyrrolidine (630 mg) was obtained by reacting (2S, 4S)-4-acetylthio-1- (4-nitrobenzyloxycarbonyl)-2-[1-(4-nitrobenzyloxycarbonyl) -2-imidazolin-2-yl]pyrrolidine (1.2 g) with 28% sodium methoxide in methanol (0.53 ml) in substantially the same manner as that of Preparation 7-1).

IR (CH$_2$Cl$_2$): 3400, 1710–1720, 1645, 1610 cm$^{-1}$

NMR (CDCl$_3$, δ) 3.7–4.0 (4H, m), 5.1–5.5 (5H, m), 8.1–8.4 (4H, m)

Preparation 24-4)

(2S, 4S)-2-(4-Hydroxymethyl-1,3-dioxolan-2-yl)-4-mercapto-1- (4-nitrobenzyloxycarbonyl)pyrrolidine (1.42 g) was obtained by reacting (2S, 4S )-2-(4-acetoxymethyl1, 3-dioxolan-2-yl)-4-acetylthio-1-(4-nitrobenzyloxycarbonyl) pyrrolidine (1.85 g) with 28% solution of sodium methoxide in methanol (1.6 ml) in substantially the same manner as that of Preparation 7-1).

IR (CH$_2$Cl$_2$): 3550–3300, 1700 cm$^{-1}$

NMR (CDCl$_3$, δ): 1.57–2.90 (4H, m), 2.93–4.40 (9H, m), 4.87–5.63 (1H, m), 5.23 (2H, s), 7.53 (2H, d, J=9 Hz), 8.23 (2H, d, J=9 Hz)

Preparation 24-5)

(2s, 4s)-2-(1,3-Dithiolan-2-yl)-4-mercapto-1-(4-nitrobenzyloxycarbonyl) pyrrolidine (0.98 g) was obtained by reacting (2S, 4S)-4-acetylthio-2-(1,3-dithiolan-2-yl)-1-(4-nitrobenzyloxycarbonyl) pyrrolidine (1.10 g)

with 28% sodium methoxide in methanol in substantially the same manner as that of Preparation 7-1).

NMR (CDCl₃, δ): 1.62–4.53 (7H, m), 3.28 (4H, s), 5.27–5.63 (1H, m), 7.58 (2H, d, J=9 Hz), 8.27 (2H, d, J=9 Hz)

Preparation 24-6)

A solution of (2S, 4S )-4-acetylthio-2-(4-bromomethyl1,3-dioxolan-2-yl)-1- (4-nitrobenzyloxycarbonyl)-pyrrolidine (1.67 g) and sodium azide (0.24 g) in N,N-dimethylformamide (25 ml) was stirred at 60° C. for 1.5 hours, and the mixture was poured into a mixture of water (250 ml) and ethyl acetate (200 ml). The organic layer was separated, washed with brine, dried over magnesium sulfate and evaporated. The residue was dissolved in a mixture of methanol (8 ml) and tetrahydrofuran (8 ml), and then deacetylated by reacting the resultant product with 28% solution of sodium methoxide in methanol (0.7 ml) to give (2S,4S)-2-(4-azidomethyl-1,3-dioxolan-2-yl) -4-mercapto-1-(4-nitrobenzyloxycarbonyl)pyrrolidine (0.99 g) in substantially the same manner as that of Preparation 7-1).

IR (Neat): 2200, 1760–1630 cm⁻¹

NMR (CDCl₃, δ) : 1.57–4.50 (12H, m) , 5.00–5.50 (1H, m), 5.21 (2H, s), 7.53 (2H, d, J=9 Hz), 8.23 (2H, d, J=9 Hz)

Preparation 24-7)

(2S, 4S )-2-(1,3-Dioxolan-2-yl)-4-mercapto-1-(4-nitrobenzyloxycarbonyl) pyrrolidine (1.73 g) was obtained by reacting (2S, 4S)-4-acetylthio-2-(1,3-dioxolan-2-yl)-1- (4-nitrobenzyloxycarbonyl)pyrrolidine (1.55 g) with 28% sodium methoxide in methanol in substantially the same manner as that of Preparation 7-1).

NMR (CDCl₃, δ): 1.66–2.66 (3H, m) , 3.10–3.33 (1H, m), 3.87–4.40 (7H, m), 5.03–5.37 (1H, m), 5.24 (2H, s), 7.56 (2H, d, J=9 Hz), 8.25 (2H, d, J=9 Hz)

Preparation 24-8)

(2s, 4s)-2-(1,3-Dithian-2-yl)-4-mercapto-1-(4-nitrobenzyloxycarbonyl) pyrrolidine (1.54 g) was obtained by reacting (2S, 4S)-4-acetylthio-2-(1,3-dithian-2-yl)-1-(4-nitrobenzyloxycarbonyl) pyrrolidine (1.51 g) with 28% sodium methoxide in methanol in substantially the same manner as that of Preparation 7-1).

IR (CH₂Cl₂): 1710 cm⁻¹

NMR (CDCl₃, δ): 1.22–5.13 (14H, m), 5.24 (2H, s), 7.22 (2H, d, J=9 Hz), 8.25 (2H, d, J=9 Hz)

Preparation 24-9)

(2S, 4S)-4-Mercapto-1-(4-nitrobenzyloxycarbonyl)-2-[5- (4-nitrobenzyloxycarbonylamino)-1,3-dioxan-2-yl]-pyrrolidine (0.97 g) was obtained by reacting (2S,4S)-4-acetylthio-1- (4-nitrobenzyloxycarbonyl)-2-[5-(4-nitrobenzyloxycarbonylamino) -1,3-dioxan-2-yl]pyrrolidine (1.46 g), with 28% sodium methoxide in methanol in substantially the same manner as that of Preparation 7-1).

IR (CH₂Cl₂): 1720, 1705 cm⁻¹

NMR (CDCl₃, δ): 1.57–1.85 (1H, m), 1.94–2.73 (3H, m), 2.90–4.35 (8H, m), 4.73–5.77 (2H, m), 5.22 (4H, s), 7.48 (2H, d, J=6 Hz), 7.51 (2H, d, J=6 Hz), 8.15 (4H, d, J=6 Hz)

Preparation 24-10)

A mixture of (2S, 4S)-2-(1-methyl-1H-tetrazol-5-yl)-1- (4-nitrobenzyloxycarbonyl)-4-(tritylthio)pyrrolidine and (2S, 4S)-2-(2-methyl-2H-tetrazol-5-yl)-1- (4-nitrobenzyloxycarbonyl) -4-(tritylthio)pyrrolidine (1.30 g) was dissolved in a mixture of pyridine (0.36 ml) and methanol (25 ml), and a solution of silver nitrate (0.73 g) in a mixture of water (5 ml) and methanol (50 ml) was added to the mixture with stirring at ambient temperature. After stirring for 1 hour, the resulting precipitates were collected by filtration and washed with diisopropyl ether. To a suspension of these precipitates in dimethylformamide (30 ml) was added potassium iodide (3.56 g) and the mixture was stirred at ambient temperature for 1 hour. The reaction mixture was poured into a mixture of water (150 ml) and ethyl acetate (150 ml). The mixture was adjusted to pH 2 with concentrated hydrochloric acid. The resultant precipitates were filtered off. The organic layer was separated, dried over magnesium sulfate and concentrated under reduced pressure to give a syrup. The syrup was subjected to a column chromatography on silica gel (20 g) and eluted with a mixture of methanol and chloroform (1:99, V/V) to give a mixture of (2S,4S)-4-mercapto-2- (1-methyl-1H-tetrazol-5-yl)-1-(4-nitrobenzyloxycarbonyl) pyrrolidine and (2S, 4S) -4-mercapto-2- (2-methyl-2H-tetrazol-5-yl)-1-(4-nitrobenzyloxycarbonyl) pyrrolidine (0.55 g).

IR (CHCl₃): 1705 cm⁻¹

EI-MS: 364 (M+), 331 (M+-33), 287 (M+-77)

Preparation 24-11)

(2S, 4S)-4-Mercapto-2-(1H-tetrazol-5-yl)-1-(4-nitrobenzyloxycarbonyl) pyrrolidine (0.58 g) was obtained by reacting (2S, 4S)-2-(1H-tetrazol-5-yl)-1-(4-nitrobenzyloxycarbonyl) -4-(tritylthio)pyrrolidine (1.85 g) with silver nitrate and potassium iodide successively in substantially the same manner as that of Preparation 24-10).

IR (CHCl₃): 1720–1660 cm⁻¹

NMR (CDCl₃, d): 1.8–2.0 (1H, m), 2.8–3.05 (2H, m), 3.2–3.7 (2H, m), 3.9–4.25 (1H, m), 5.0–5.3 (1H, m), 5.24 (2H, s), 7.45 (2H, d, J=8.5 Hz), 8.17 (2H, d, J=8.5 Hz)

Preparation 25

(2S, 4R)-4-Methanesulfonyloxy-1-(4-nitrobenzyloxycarbonyl) -2-[2-{2-(4-nitrobenzyloxycarbonylamino)ethyl}-thiazol-4-yl]pyrrolidine (1.04 g) was obtained by reacting (2S, 4R)-2-bromoacetyl-4-methanesulfonyloxy-1-(4-nitrobenzyloxycarbonyl) pyrrolidine (1.5 g) with 3-(4-nitrobenzyloxycarbonylamino) propionthioamide (0.92 g) in substantially the same manner as that of Preparation 3-1).

IR (Neat): 3350, 1700–1720, 1610 cm⁻¹

NMR (CDCl₃, δ): 3.08 (3H, s), 5.1–5.7 (6H, m), 7.52 (4H, d, J=9 Hz), 8.25 (4H, d, J=9 Hz)

Preparation 26

(2S, 4R)-4-Methanesulfonyloxy-2-[2-(methylamino)-thiazol-4-yl]-1- (4-nitrobenzyloxycarbonyl)pyrrolidine (2.0 g) was obtained by reacting (2S,4R)-2-bromoacetyl-4-methanesulfonyloxy-1- (4-nitrobenzyloxycarbonyl)pyrrolidine (2.0 g) with N-methylthiourea (0.8 g) in substantially the same manner as that of Preparation 3-1).

Preparation 27

To a solution of (2S, 4R)-2-bromoacetyl-4-methanesulfonyloxy-1- (4-nitrobenzyloxycarbonyl)pyrrolidine (4.0 g) in a mixture of N,N-dimethylacetamide (10 ml) and dichloromethane (5 ml) was added 2,2-dimethoxythioacetamide (1.28 g) at room temperature. After stirring at room temperature for 12 hours, the mixture was poured into ethyl acetate. The organic layer was washed with water, saturated sodium bicarbonate and brine successively, dried over magnesium sulfate, and evaporated. The obtained oil was subjected to a column chromatography on silica gel and eluted with a mixture of dichloromethane and acetone (20:1, V/V) to give (2S, 4R)-2-[2-(dimethoxymethyl)thiazol-4-yl]-4-methanesulfonyloxy-1- (4-nitrobenzyloxycarbonyl)pyrrolidine (2.6 g).

IR (CH$_2$Cl$_2$): 1700, 1600 cm$^{-1}$

NMR (CDCl$_3$, δ): 2.5–2.8 (2H, m), 3.08 (3H, s), 3.41 (6H, s), 3.9–4.1 (2H, m), 5.1–5.6 (5H, m), 7.0–7.7 (3H, m), 8.0–8.3 (2H, m)

Preparation 28

To a solution of (2S, 4R)-2-[2-(dimethoxymethyl)-thiazol-4-yl]-4-methanesulfonyloxy-1-(4-nitrobenzyloxycarbonyl) pyrrolidine (2.6 g) in acetone (100 ml) was added p-toluenesulfonic acid (0.49 g) at room temperature. After stirring under reflux for 1 hour, the mixture was evaporated. The residue was dissolved in ethyl acetate, washed in turn with saturated aqueous sodium bicarbonate and brine, and dried over magnesium sulfate. The organic layer was evaporated to give (2S,4R)-2-(2-formylthiazol-4-yl) -4-methanesulfonyloxy-1-(4-nitrobenzyloxycarbonyl) pyrrolidine (2.26 g).

IR (CH$_2$Cl$_2$): 1710, 1615 cm$^{-1}$

NMR (CDCl$_3$, δ): 3.10 (3H, s), 5.1–5.7 (4H, s), 7.0–7.8 (3H, m), 8.1–8.4 (2H, m), 10.01 (1H, s)

Preparation 29

To a solution of (2S,4R)-2-(2-formylthiazol-4-yl)-4-methanesulfonyloxy-1- (4-nitrobenzyloxycarbonyl)pyrrolidine (2.26 g) in a mixture of methanol (30 ml) and tetrahydrofuran (30 ml) was added sodium borohydride (94 mg) at 0° C. After stirring at 0° C. for 30 minutes, acetic acid (0.6 ml) was added to the solution. After the mixture was evaporated, the residue was dissolved in ethyl acetate, washed with water, saturated sodium bicarbonate and brine successively. The dried organic layer was evaporated to give (2S, 4R)-2-[2-(hydroxymethyl) thiazol-4-yl]-4-(methanesulfonyloxy)-1-(4-nitrobenzyloxycarbonyl) pyrrolidine (2.09 g)

IR (CH$_2$Cl$_2$): 3600, 1705, 1600 cm$^{-1}$

NMR (CDCl$_3$, δ): 2.5–2.8 (2H, m), 3.11 (3H, s), 4.90 (2H, s), 5.1–5.6 (4H, m), 7.0–7.7 (3H, m), 8.1–8.4 (2H, m)

Preparation 30

To a solution of (2S, 4R)-2-[2-(hydroxymethyl)-thiazol-4-yl]-4-methanesulfonyloxy-1-(4-nitrobenzyloxycarbonyl) pyrrolidine (2.1 g) in acetonitrile (50 ml) was added chlorosulfonyl isocyanate (0.48 ml) at 0°–5° C. and the mixture was stirred at ambient temperature for 1 hour. Water (3 ml) was added to the solution at the same temperature and the mixture was stirred for 20 hours. After the solvent was removed, the residue was dissolved in ethyl acetate, and washed with water, saturated sodium bicarbonate and brine successively. The dried organic layer was evaporated to give (2S,4R)2-[2-(carbamoyloxymethyl)thiazol-4-yl]-4-methanesulfonyloxy-1-(4-nitrobenzyloxycarbonyl) pyrrolidine (2.2 g).

IR (CH$_2$Cl$_2$): 3550, 3440, 1740, 1710, 1610 cm$^{-1}$

NMR (CDCl$_3$, δ): 2.5–2.8 (2H, m), 3.11 (3H, s), 4.9–5.6 (6H, m), 7.0–7.7 (3H, m), 8.1–8.4 (2H, m)

Preparation 31

To a solution of S-methylisothiourea sulfate (2 g) in 2N sodium hydroxide (20 ml) was dropwise added a solution of (2S, 4R)-2-chloroformyl-4-methanesulfonyloxy-1-(4-nitrobenzyloxycarbonyl) pyrrolidine (3 g) in tetrahydrofuran (20 ml) and dichloromethane (20 ml) at 0°–5° C. After stirring at the same temperature for 30 minutes, the mixture was evaporated to remove organic solvent, extracted with ethyl acetate and washed with water and brine successively. The dried organic layer was evaporated and the resulting residue was dissolved in glacial acetic acid (30 ml) and 1,4-dioxane (20 ml). Sodium acetate (1 g) and hydroxylamine hydrochloride (770 mg) were added to the solution and the mixture was stirred at 90° C. for 2 hours. After the mixture was evaporated, the oily residue was dissolved in ethyl acetate. The organic layer was washed with water and brine successively, dried over magnesium sulfate, and evaporated. The obtained syrup was subjected to a column chromatography on silica gel and eluted with a mixture of acetone and dichloromethane (1:5, V/V) to give (2S, 4R)-4-methanesulfonyloxy-1-(4-nitrobenzyloxycarbonyl) -2-(3-amino-1,2,4-oxadiazol-5-yl)pyrrolidine (500 mg).

IR (Nujol): 1690–1710, 1605 cm$^{-1}$

NMR (CDCl$_3$-DMSO-d$_6$, d): 3.18 (3H, s), 3.9–4.1 (2H, m), 5.0–5.6 (4H, m), 7.3–7.7 (2H, m), 8.1–8.4 (2H, m)

Preparation 32

To a solution of ethyl 2-(4-nitrobenzyloxycarbonylamino)acetimidate hydrochloride (1.6 g) in tetrahydrofuran (50 ml) were dropwise added triethylamine (0.7 ml) and a solution of (2S, 4R)-2-chloroformyl-4-methaneslufonyloxy-1-(4-nitrobenzyloxycarbonyl) pyrrolidine (1.8 g) in tetrahydrofuran (30 ml) at −30° C. After stirring at 0° C. for 3 hours, the mixture was evaporated to remove the solvent. The residue was dissolved in ethyl acetate, and washed with water and brine successively. The dried organic layer was evaporated and the residue was dissolved in glacial acetic acid (30 ml) and 1,4-dioxane (20 ml). Sodium acetate (550 mg) and hydroxylamine hydrochloride (470 mg) were added to the solution and the solution was stirred at 90° C. for 1 hour. After the solvent was removed, the oily residue was dissolved in ethyl acetate, washed with water and brine, dried over magnesium sulfate and evaporated. The obtained syrup was subjected to a column chromatography on silica gel and eluted with a mixture of acetone and dichloromethane (1:9, V/V) to give (2S,4R)-4-methanesulfonyloxy-1-(4-nitrobenzyloxycarbonyl) -2-[3-{N-(4-nitrobenzyloxycarbonyl) aminomethyl}-1,2,4-oxadiazol-5-yl]pyrrolidine (1.8 g).

IR (CH$_2$Cl$_2$): 3480, 1740, 1620, 1600 cm$^{-1}$

NMR (CDCl$_3$, δ): 3.08 (3H, s), 3.8–4.1 (2H, m), 4.3–4.6 (2H, m), 4.9–5.7 (6H, m), 7.1–7.6 (4H, m), 8.0–8.3 (4H, m)

Preparation 33

To a solution of ethyl 2-(4-nitrobenzyloxycarbonylamino)acetimidate hydrochloride (1.4 g) in dichloromethane (30 ml) were dropwise added triethylamine (0.66 ml) and a solution of (2S, 4R) -2-chloroformyl-4-methanesulfonyloxy-1- (4-nitrobenzyloxycarbonyl)pyrrolidine (1.5 g) in dichloromethane (30 ml) at 0° C. After stirring at 0° C. for 1 hour, the mixture was evaporated to remove the solvent. The residue was dissolved in ethyl acetate, and washed with water and brine successively. The dried organic layer was evaporated and the residue was dissolved in acetic acid (20 ml). Hydrazine hydrate (0.22 ml) and sodium acetate (360 mg) were added to the solution and the mixture was stirred at room temperature for 2 hours. After the solvent was removed, the oily residue was dissolved in ethyl acetate, washed with water and brine, dried over magnesium sulfate, and evaporated. The obtained syrup was subjected to a column chromatography on silica gel and eluted with a mixture of acetone and dichloromethane (1:9, V/V) to give (2S, 4R)-4-methanesulfonyloxy-1-(4-nitrobenzyloxycarbonyl) -2-[3-{N-(4-nitrobenzyloxycarbonyl)aminomethyl}-1H-1,2,4-triazol-5-yl]pyrrolidine (1.5 g).

IR (CH$_2$Cl$_2$): 3400–3450, 1710, 1610 cm$^{-1}$

NMR (CDCl$_3$, δ): 3.02 (3H, s), 4.44 (2H, d, J=7 Hz), 5.0–5.6 (6H, m), 5.7–6.1 (1H, m), 7.4–7.7 (4H, m), 8.1–8.4 (4H, m)

Preparation 34

To a solution of (2S, 4R)-4-methanesulfonyloxy-1-(4-nitrobenzyloxycarbonyl) -2-thiocarbamoylpyrrolidine (2.0 g) in dichloromethane (40 ml) was added a solution of ethyl bromopyruvate (1.04 ml) in absolute ethanol (10 ml) at 0° C. After stirring at room temperature for 2 hours, the mixture was evaporated. The residue was dissolved in ethyl acetate, and washed with saturated sodium bicarbonate and brine successively. The dried organic layer was evaporated and the residue was dissolved in tetrahydrofuran (15 ml) and in sodium hydroxide (15 ml). After stirring at 35°–45° C. for 1 hour, the mixture was evaporated and poured into ethyl acetate. To this mixture was added 1N hydrochloric acid (20 ml), and then organic layer was separated, and washed with brine. The dried organic layer was evaporated to give (2S,4R)-2- (4-carboxythiazol-2-yl)-4-methanesulfonyloxy-1-(4-nitrobenzyloxycarbonyl) pyrrolidine (1.54 g).

IR (CH$_2$Cl$_2$): 3500, 3380, 1700, 1670, 1600 cm$^{-1}$

NMR (CDCl$_3$, δ): 3.09 (3H, s), 5.1–5.5 (4H, m), 6.50 (1H, br s), 7.0–7.8 (3H, m), 7.9–8.3 (3H, m)

Preparation 35

To a mixture of dimethylformamide (0.45 ml) and tetrahydrofuran (10 ml) was dropwise added phosphorus oxychloride (0.46 ml) at −5°∫5° C., and the mixture was stirred at the same temperature for 30 minutes. To the mixture was added a solution of (2S,4R)-2-(4-carboxythiazol-2-yl) -4-methanesulfonyloxy-1-(4-nitrobenzyloxycarbonyl) pyrrolidine (1.54 g) in tetrahydrofuran (20 ml) at −5°∫5° C., followed by stirring at the same temperature for 30 minutes. The mixture was dropwise added to concentrated ammonia water (15 ml) at 0°–10° C. with stirring. The mixture was stirred at the same condition for 2 hours. Tetrahydrofuran was removed under reduced pressure to give a residue, which was extracted with ethyl acetate. The organic layer was dried over magnesium sulfate and concentrated under reduced pressure to give (2S, 4R)-2-(4-carbamoylthiazol)-2-yl) -4-methanesulfonyloxy-1-(4-nitrobenzyloxycarbonyl)pyrrolidine (1.4 g).

IR (CHCl$_3$): 1760, 1700, 1600 cm$^{-1}$

NMR (CDCl$_3$, δ): 3.11 (3H, s), 5.1–5.6 (4H, m), 7.2–8.3 (5H, m)

Preparation 36-1)

(2S, 4S)-4-Acetylthio-1-(4-nitrobenzyloxycarbonyl)-2- [2-{2-(4-nitrobenzyloxycarbonylamino)ethyl}thiazol-4-yl]pyrrolidine (640 mg) was obtained by reacting (2S,4R)-4-methanesulfonyloxy-1- (4-nitrobenzyloxycarbonyl)-2-[2-{2- (4-nitrobenzyloxycarbonylamino)ethyl} thiazol-4-yl]pyrrolidine (1.04 g) with thioacetic S-acid (0.23 ml) in substantially the same manner as that of Preparation 6.

IR (Neat): 3350, 1690–1720, 1610 cm$^{-1}$

NMR (CDCl$_3$, δ): 2.30 (3H, s), 5.0–5.4 (5H, m), 5.4–5.7 (1H, m), 6.98 (1H, br s), 7.2–7.7 (4H, m), 8.0–8.4 (4H, m)

Preparation 36-2)

(2S, 4S)-4-Acetylthio-2-[2-(methylamino)thiazol-4-yl]-1-(4-nitrobenzyloxycarbonyl)pyrrolidine (1.07 g) was obtained by reacting (2S, 4R)-4-methanesulfonyloxy-2- [2-(methylamino)thiazol-4-yl]-1-(4-nitrobenzyloxycarbonyl) pyrrolidine (2.0 g) with thioacetic S-acid (0.61 ml) in substantially the same manner as that of Preparation 6.

IR (Neat): 1670–1740, 1610 cm$^{-1}$

NMR (CDCl$_3$, δ): 2.31 (3H, s), 2.98 (3H, s), 4.8–5.6 (4H, m), 6.28 (1H, br s), 7.2–7.8 (2H, m), 8.0–8.4 (2H, m)

Preparation 36-3)

(2S, 4S)-4-Acetylthio-2-[2-(carbamoyloxymethyl)-thiazol-4-yl]-1-(4-nitrobenzyloxycarbonyl)pyrrolidine (1.5 g) was obtained by reacting (2S,4R)-2-[2-(carbamoyloxymethyl) thiazol-4-yl]-4-methanesulfonyloxy-1-(4-nitrobenzyloxycarbonyl) pyrrolidine (2.2 g) with thioacetic S-acid (0.66 ml) in substantially the same manner as that of Preparation 6.

IR (CH$_2$Cl$_2$): 3540, 3420, 1740, 1700, 1600 cm$^{-1}$

NMR (CDCl$_3$, δ): 2.29 (3H, s), 3.8–4.4 (2H, m), 4.8–5.4 (5H, m), 6.9–7.7 (3H, m), 8.0–8.3 (2H, m)

Preparation 36-4)

(2S, 4S )-4-Acetylthio-1-(4-nitrobenzyloxycarbonyl)-2- (3-amino-1,2,4-oxadiazol-5-yl)pyrrolidine (420 mg) was obtained by reacting (2S,4R)-4-methanesulfonyloxy-1- (4-nitrobenzyloxycarbonyl)-2-(3-amino-1,2,4-oxadiazol-5-yl) pyrrolidine (930 mg) with thioacetic S-acid (0.31 ml) in substantially the same manner as that of Preparation 6.

IR (Nujol): 1695, 1635, 1600 cm$^{-1}$

NMR (DMSO-d$_6$, δ) : 2.32 (3H, s), 3.9–4.2 (2H, m), 5.0–5.4 (3H, m), 6.32 (2H, br s) , 7.3–7.8 (2H, m), 8.2–8.5 (2H, m)

Preparation 36-5)

(2S, 4S)-4-Acetylthio-1-(4-nitrobenzyloxycarbonyl)-2- [3-{N-(4-nitrobenzyloxycarbonylamino)methyl}-1,2, 4-oxadiazol-5-yl]pyrrolidine (1.5 g) was obtained by reacting (2S, 4R)-4-methanesulfonyloxy-1-(4-nitrobenzyloxycarbonyl) -2-[3-{N-(4-nitrobenzyloxycarbonyl)aminomethyl}-1,2,4-oxadiazol-5-yl]pyrrolidine (1.8 g) with thioacetic S-acid (0.42 ml) in substantially the same manner as that of Preparation 6.

IR (CH$_2$Cl$_2$): 1720, 1705, 1610 cm$^{-1}$

NMR (CDCl$_3$, δ): 2.32 (3H, s) , 3.9–4.4 (2H, m), 4.6–4.8 (2H, m), 5.1–5.7 (5H, m) , 7.3–7.7 (4H, m), 8.1–8.4 (4H, m)

Preparation 36-6)

(2S, 4S)-4-Acetylthio-1-(4-nitrobenzyloxycarbonyl)-2- [3-{N-(4-nitrobenzyloxycarbonyl)aminomethyl}-1H-1,2,4-triazol-5-yl]pyrrolidine (800 mg) was obtained by reacting (2S, 4R)-4-methanesulfonyloxy-1-(4-nitrobenzyloxycarbonyl)-2- [3-{N-(4-nitrobenzyloxycarbonyl)aminomethyl}-1H-1,2,4-triazol-5-yl]pyrrolidine (1.5 g) with thioacetic S-acid (0.35 ml) in substantially the same manner as that of Preparation 6.

IR (CH$_2$Cl$_2$): 1710, 1615 cm$^{-1}$

NMR (CDCl$_3$-DMSO-d$_6$, δ): 2.31 (3H, s) , 4.42 (2H, d, J=6 Hz) , 4.9–5.4 (5H, m), 7.0–7.8 (4H, m), 8.0–8.3 (4H, m)

Preparation 36-7)

(2S,4S)-4-Acetylthio-2-(4-carbamoylthiazol-2-yl) -1-(4-nitrobenzyloxycarbonyl) pyrrolidine (1.1 g) was obtained by reacting (2S, 4R)-2-(4-carbamoylthiazol-2-yl)-4-methanesulfonyloxy-1- (4-nitrobenzyloxycarbonyl)-pyrrolidine (1.4 g) with thioacetic S-acid (0.43 ml) in substantially the same manner as that of Preparation 6.

IR (CH$_2$Cl$_2$): 3500, 3400, 1700, 1690 cm$^{-1}$

NMR (CDCl$_3$, δ): 2.31 (3H, s), 3.4–3.7 (1H, m), 3.9–4.4 (2H, m), 5.2–5.4 (3H, m), 6.1 (1H, br s), 6.9–7.7 (3H, m), 8.0–8.3 (3H, m)

Preparation 37-1)

(2s, 4s)-4-Mercapto-1-(4-nitrobenzyloxycarbonyl)-2-[2-{2-(4-nitrobenzyloxycarbonylamino)ethyl}thiazol-4-yl]pyrrolidine (630 mg) was obtained by reacting (2S, 4S)-4-acetylthio-1-(4-nitrobenzyloxycarbonyl)-2-[2- {2-

(4-nitrobenzyloxycarbonylamino)ethyl}thiazol-4-yl]pyrrolidine (640 mg) with 28% sodium methoxide in methanol in substantially the same manner as that of Preparation 7-1).

IR (Neat): 3350, 1690–1740, 1610 cm$^{-1}$

NMR (CDCl$_3$, δ): 4.9–5.3 (5H, m), 5.3–5.6 (1H, m), 7.50 (4H, d, J=9 Hz), 8.28 (4H, d, J=9 Hz)

Preparation 37-2)

(2S, 4S)-4-Mercapto-2-[2-(methylamino)thiazol-4-yl]-1-(4-nitrobenzyloxycarbonyl)pyrrolidine (0.91 g) was obtained by reacting (2S, 4S)-4-acetylthio-2-[2-(methylamino) thiazol-4-yl]-1-(4-nitrobenzyloxycarbonyl)-pyrrolidine (1.07 g) with 28% sodium methoxide in methanol solution (1.2 ml) in substantially the same manner as that of Preparation 7-1).

IR (Neat): 3350, 1690–1710, 1605 cm$^{-1}$

NMR (CDCl$_3$, δ): 2.98 (3H, s), 4.7–5.5 (4H, m), 6.2–6.4 (1H, m), 7.2–7.7 (2H, m), 8.0–8.3 (2H, m)

Preparation 37-3)

(2S, 4S)-2-[2-(Carbamoyloxymethyl)thiazol-4-yl]-4-mercapto-1- (4-nitrobenzyloxycarbonyl)pyrrolidine (1.2 g) was obtained by reacting (2S, 4S)-4-acetylthio-2-[2-(carbamoyloxymethyl)thiazol-4-yl]-1-(4-nitrobenzyloxycarbonyl) pyrrolidine (1.53 g) with 28% sodium methoxide in methanol solution (1.5 ml) in substantially the same manner as that of Preparation 7-1).

IR (CH$_2$Cl$_2$) 3550, 3450, 1740, 1710, 1610 cm$^{-1}$

NMR (CDCl$_3$, δ): 4.8–5.4 (5H, m), 7.0–7.7 (3H, m), 8.0–8.3 (2H, m)

Preparation 37-4)

(2S, 4S)-2-(3-Amino-1,2,4-oxadiazol-5-yl)-4-mercapto-1- (4-nitrobenzyloxycarbonyl) pyrrolidine (400 mg) was obtained by reacting (2S, 4S)-4 -acetylthio-1-(4-nitrobenzyloxycarbonyl) -2-(3-amino-1,2,4-oxadiazol-5-yl)pyrrolidine (420 mg) with 28% solution of sodium methoxide in methanol (0.4 ml) in substantially the same manners as that of Preparation 7-1).

IR (Neat): 1705, 1630, 1605 cm$^{-1}$

NMR (CDCl$_3$, δ): 4.3–4.7 (2H, m), 4.9–5.5 (3H, m), 7.2–7.7 (2H, m), 8.1–8.4 (2H, m)

Preparation 37-5)

(2S, 4S) -4-Mercapto-1-(4-nitrobenzyloxycarbonyl)-2-[3-{N- (4-nitrobenzyloxycarbonylamino)methyl}-1,2,4-oxadiazol-5-yl]pyrrolidine (1.4 g) was obtained by reacting (2S, 4S) -4-acetylthio-1-(4-nitrobenzyloxycarbonyl)-2- [3-{N-(4-nitrobenzyloxycarbonyl)aminomethyl}-1,2,4-oxadiazol-5-yl]pyrrolidine (1.5 g) with 28% solution of sodium methoxide in methanol (1.0 ml) in substantially the same manner as that of Preparation 7-1).

IR (Neat): 3300–3450, 1705–1720, 1610 cm$^{-1}$

NMR (CDCl$_3$, δ): 3.9–4.3 (2H, m), 4.5–4.7 (2H, m), 5.1–5.6 (5H, m), 7.4–7.7 (4H, m) , 8.1–8.4 (4H, m)

Preparation 37-6)

(2 S, 4S )-4-Mercapto-1-(4-nitrobenzyloxycarbonyl)-2- [3-{N-(4-nitrobenzyloxycarbonylamino)methyl}-1H-1,2,4-triazol-5-yl]pyrrolidine (780 mg) was obtained by reacting (2S, 4S )-4-acetylthio-1-(4-nitrobenzyloxycarbonyl)-2- [3-{N-(4-nitrobenzyloxycarbonyl)aminomethyl}-1H-1,2,4-triazol-5-yl]pyrrolidine (800 mg) with 28% solution of sodium methoxide in methanol (0.54 ml) in substantially the same manner as that of Preparation 7-1).

IR (CH$_2$Cl$_2$): 3690, 1700, 1610 cm$^{-1}$

NMR (CDCl$_3$, δ): 4.48 (2H, d, J=6 Hz), 5.1–5.6 (5H, m), 7.3–7.7 (4H, m), 8.1–8.4 (4H, m)

Preparation 37-7)

(2S, 4S)-2-(4-Carbamoylthiazol-2-yl)-4-mercapto-1-(4-nitrobenzyloxycarbonyl) pyrrolidine (860 mg) was obtained by reacting (2S, 4S)-4-acetylthio-2-(4-carbamoylthiazol-2-yl) -1-(4-nitrobenzyloxycarbonyl)pyrrolidine (1.1 g) with 28% sodium methoxide solution in methanol (1.2 ml) in substantially the same manner as that of Preparation 7-1).

IR (CH$_2$Cl$_2$): 3600, 3430, 3300,. 1710, 1695 cm$^{-1}$

NMR (CDCl$_3$, δ): 5.1–5.4 (3H, m), 5.9 (1H, br s), 6.9–7.7 (3H, m), 8.1 (1H, s), 8.22 (2H, d, J=9 Hz)

Preparation 38

(2S, 4S)-4-Acetylthio-2-carbamoyl-1-(4-nitrobenzyloxycarbonyl) pyrrolidine (2 g) was obtained by reacting (2S, 4R)-2-carbamoyl-4-methanesulfonyloxy-1-(4-nitrobenzyloxycarbonyl) pyrrolidine (2.5 g) with thioacetic S-acid (0.69 ml) in substantially the same manner as that of Preparation 6-1).

Preparation 39

(2S, 4S)-2-Carbamoyl-1-(4-nitrobenzyloxycarbonyl)-4-(tritylthio) pyrrolidine (2.8 g) was obtained by reacting (2S, 4S)-4-acetylthio-2-carbamoyl-1-(4-nitrobenzyloxycarbonyl) pyrrolidine (2.0 g) with 28% sodium methoxide in methanol (1.4 ml) and trityl chloride (2.3 g) in substantially the same manner as that of Preparation 18.

IR (CH$_2$Cl$_2$): 1700, 1605 cm$^{-1}$

NMR (CDCl$_3$, δ): 2.6–3.2 (2H, m), 4.03 (1H, t, J=7 Hz), 5.08, 5.19 (2H, ABq, J=13 Hz), 5.8–6.3 (2H, m), 7.1–7.7 (17H, m), 8.21 (2H, d, J=8 Hz)

Preparation 40

To (2S, 4R)-2-Carbamoyl-1-(4-nitrobenzyloxycarbonyl)-4-(tritylthio) pyrrolidine (2 g) was added N,N-dimethylformamide dimethyl acetal (1 ml) and the mixture was stirred at 70° C. for 1 hour, and evaporated in vacuo. The oily residue was dissolved in acetic acid (20 ml) and to this solution were added sodium acetate (0.43 g) and hydroxylamine hydrochloride (0.37 g) at room temperature. After stirring at 70° C. for 1 hour, the mixture was poured into water and ethyl acetate. The organic layer was washed with saturated sodium bicarbonate and brine successively, and dried over magnesium sulfate. After the solvent was evaporated, the residue was subjected to a column chromatography on silica gel and eluted with a mixture of acetone and dichloromethane (1:20, V/V) to give (2S ,4S)-1-(4-nitrobenzyloxycarbonyl)-2-(1,2,4-oxadiazol-5-yl)-4-(tritylthio)pyrrolidine (1.16 g).

IR (CH$_2$Cl$_2$): 1710, 1610, 1580 cm$^{-1}$

NMR (CDCl$_3$, δ): 4.8–5.3 (3H, m), 7.1–7.7 (17H, m), 8.0–8.4 (3H, m)

Preparation 41

To a solution of (2S, 4R)-2-bromoacetyl-4-methanesulfonyloxy-1- (4-nitrobenzyloxycarbonyl)pyrrolidine (20 g) in a mixture of methanol (200 ml) and dichloromethane (200 ml) was added 2-(N-t-butoxycarbonylamino)thioacetamide (20 g) at room temperature. After stirring at ambient temperature for 12 hours, the mixture was poured into ethyl acetate, washed with saturated sodium bicarbonate and brine successively. The dried organic layer was evaporated, and the obtained oil was subjected to a column chromatography on silica gel and eluted with a mixture of acetone and dichloromethane (1:5, V/V) to give (2S,4R)-2-[2-(N-t-butoxycarbonylamino) methylthiazol-4-yl]-4-methanesulfonyloxy-1- (4-nitrobenzyloxycarbonyl)pyrrolidine (9.7 g).

IR (CH$_2$Cl$_2$): 1705, 1605 cm$^{-1}$

NMR (CDCl$_3$, δ): 1.42 (9H, s) , 2.4–2.7 (2H, m), 3.02 (3H, s), 3.6–4.2 (2H, m), 4.52 (2H, d, J=7 Hz), 5.0–5.6 (3H, m) , 6.9–7.8 (3H, m), 8.0–8.3 (2H, m)

Preparation 42

To a solution of (2S, 4R)-2-[2-(N-t-butoxycarbonylamino) methylthiazol-4-yl]-4-methanesulfonyloxy-1-(4-nitrobenzyloxycarbonyl) pyrrolidine (2.85 g) in dichloromethane was added trifluoroacetic acid (30 ml) at ambient temperature. After stirring at the same temperature for 1 hour, the solvent was removed. The residue was dissolved in a mixture of tetrahydrofuran (30 ml) and water (10 ml), and a solution of potassium cyanate (2.2 g) in water (10 ml) was dropwise added to the solution, keeping the pH between 3 and 4 with conc. hydrochloric acid at 50° C. After stirring at the same temperature for 2 hours, the solvent was evaporated, and extracted with ethyl acetate. The organic layer was washed with brine, dired over magnesium sulfate and concentrated to give a syrup. The syrup was subjected to a column chromatography on silica gel and eluted with a mixture of methanol and dichloromethane (1:20, V/V) to give (2S,4R)-4-methanesulfonyloxy-1-(4-nitrobenzyloxycarbonyl) -2-[2-(ureidomethyl)thiazol-4-yl]pyrrolidine (1.5 g).

IR (CH$_2$Cl$_2$): 3200–3300, 1670–1690, 1610 cm$^{-1}$

NMR (CDCl$_3$, δ): 2.4–2.7 (2H, m), 3.09 (3H, s), 3.9–4.1 (2H, m), 4.52 (2H, d, J=6 Hz), 6.9–7.6 (3H, m), 8.1–8.4 (2H, m)

Preparation 43

(2S, 4S)-4-Acetylthio-1-(4-nitrobenzyloxycarbonyl)-2-[2-(ureidomethyl) thiazol-4-yl]pyrrolidine (1.4 g) was obtained by reacting (2S, 4R) -4-methanesulfonyloxy-1-(4-nitrobenzyloxycarbonyl) -2-[2-(ureidomethyl)-thiazol-4-yl]pyrrolidine with thioacetic S-acid in substantially the same manner as that of Preparation 6-1).

IR (CH$_2$Cl$_2$): 3300–3400, 1660–1700, 1605 cm$^{-1}$

NMR (CDCl$_3$, δ): 2.19 (3H, s), 3.3–3.7 (1H, m), 3.8–4.4 (2H, m), 4.56 (2H, d, J=6 Hz), 4.9–5.4 (5H, m), 6.0–6.3 (1H, m), 6.92 (1H, s), 7.1–7.7 (2H, m), 8.0–8.4 (2H, m)

Preparation 44

To a solution of sodium borohydride (0.74 g) in tetrahydrofuran (30 ml) was dropwise added boron trifluoride etherate (about 47%, 9 ml) at 0° C. After stirring at the same temperature for 30 minutes, a solution of (2S, 4R)-2-(4-carboxythiazol-2-yl)-4-methanesulfonyloxy-1-(4-nitrobenzyloxycarbonyl)pyrrolidine (2.8 g) in tetrahydrofuran (20 ml) was added thereto at 0° C., and the mixture was stirred at ambient temperature for 12 hours. To the mixture was added methanol (10 ml) and the mixture was evaporated. The residue was dissolved in ethyl acetate, washed with water and brine successively, dried over magnesium sulfate and then evaporated. The obtained oily residue was subjected to a column chromatography on silica gel and eluted with a mixture of acetone and dichloromethane (1:5, V/V) to give (2S, 4R)-2-(4-hydroxymethylthiazol-2-yl)-2-methanesulfonyloxy-1- (4-nitrobenzyloxycarbonyl)pyrrolidine (860 mg)

IR (CH$_2$Cl$_2$): 3300–3400, 1700–1710, 1610 cm$^{-1}$

NMR (CDCl$_3$, δ): 3.07 (3H, s), 3.7–4.3 (2H, m), 4.69 (2H, s), 5.1–5.6 (4H, m), 7.1–7.7 (3H, m), 8.0–8.4 (2H, m)

Preparation 45

(2S, 4S)-4-Acetylthio-2-(4-hydroxymethylthiazol-2-yl)-1-(4-nitrobenzyloxycarbonyl) pyrrolidine (620 mg) was obtained by reacting (2S, 4R)-2-(4-hydroxymethylthiazol-2-yl) -4-methanesulfonyloxy-1-(4-nitrobenzyloxycarbonyl)-pyrrolidine (860 mg) with thioacetic S-acid (0.27 ml) in substantially the same manner as that of Preparation 6-1).

IR (CH$_2$Cl$_2$): 3300–3400, 1690–1710, 1610 cm$^{-1}$

NMR (CDCl$_3$, δ): 2.30 (3H, s), 3.3–3.7 (1H, m), 4.0–4.5 (3H, m), 4.71 (2H, s), 5.1–5.6 (3H, m), 7.19 (1H, s), 7.2–7.8 (2H, m), 8.0–8.4 (2H, m)

Preparation 46

To a solution of (2S,4S)-4-acetylthio-2-(4-hydroxymethylthiazo-1-2-yl) -1-(4-nitrobenzyloxycarbonyl)-pyrrolidine (2.24 g) in dichloromethane (40 ml) was added triethylamine (2.1 ml) and methanesulfonyl chloride (1.2 ml) at 0° C. After stirring for 30 minutes at the same temperature, water (40 ml) was added thereto. The organic layer was washed with brine, dried over magnesium sulfate and evaporated to give (2S,4S)-4-acetylthio-2-[4- (methanesulfonyloxymethyl)thiazol-2-yl]-1-(4-nitrobenzyloxycarbonyl) pyrrolidine (1.6 g).

IR (CH$_2$Cl$_2$): 1690–1710, 1610 cm$^{-1}$

NMR (CDCl$_3$, δ): 2.31 (3H, s), 3.09 (3H, s), 3.4–3.7 (1H, m), 5.2–5.5 (5H, m), 7.41 (1H, s), 7.0–7.7 (2H, m), 8.2–8.4 (2H, m)

Preparation 47

To a solution of (2S,4S)-4-acetylthio-2-[4-(methanesulfonyloxymethyl) thiazol-2-yl]-1-(4-nitrobenzyloxycarbonyl)pyrrolidine (1.5 g) in dimethylformamide (20 ml) was added sodium azide (0.15 g) at ambient temperature. After stirring at 70° C. for 2 hours, the mixture was partitioned between ethyl acetate and water. The organic layer was washed with water and brine successively, dried over magnesium sulfate and concentrated to give a syrup. The syrup was subjected to a column chromatography on silica gel and eluted with a mixture of acetone and dichloromethane (1:9, V/V) to give (2S, 4S)-4-acetylthio-2-(4-azidomethylthiazol-2-yl) -1-(4-nitrobenzyloxycarbonyl)pyrrolidine (500 mg).

IR (CH$_2$Cl$_2$): 2200, 1690–1710, 1610 cm$^{-1}$

NMR (CDCl$_3$, δ): 2.24 (3H, s), 4.41 (2H, s), 5.1–5.5 (3H, m), 7.18 (1H, s), 7.1–7.7 (2H, m), 8.1–8.4 (2H, m)

Preparation 48

To a solution of (2S, 4R)-4-t-butyldimethylsilyloxy-1-(4-nitrobenzyloxycarbonyl)-2-thiocarbamoylpyrrolidine (3.7 g) in tetrahydrofuran (50 ml) was added methyl iodide (5 ml) at ambient temperature. After stirring at the same temperature for 24 hours, the mixture was evaporated and dissolved in methanol (50 ml). Aminoacetaldehyde dimethyl acetal (0.93 ml) was added to the solution at ambient temperature. After stirring at ambient temperature for 2 hours, the solvent was removed, and then the obtained oil was subjected to a column chromatography on silica gel and eluted with a mixture of methanol and dichloromethane (1:5, V/V) to give (2S, 4R)-4-t-butyldimethylsilyloxy-2-[N$^1$-(2,2-dimethoxyethyl) amidino]-1-(4-nitrobenzyloxycarbonyl)pyrrolidine hydriodide (5.4 g).

IR (CH$_2$Cl$_2$): 1680, 1610 cm$^{-1}$

NMR (CDCl$_3$, δ): 0.05 (6H, s), 0.81 (9H, s), 3.41 (3H, s), 3.43 (3H, s), 5.30 (2H, s), 7.62 (2H, d, J=9 Hz), 8.26 (2H, d, J=9 Hz)

Preparation 49

To a solution of (2S, 4R)-4-t-butyldimethylsilyloxy-2-[N$^1$-(2,2-dimethoxyethyl)amidino]-1-(4-nitrobenzyloxycarbonyl) pyrrolidine hydriodide (3.4 g) in tetrahydrofuran (60 ml) was added p-toluenesulfonic acid (10 mg) at ambient temperature. After stirring under reflux for 2 hours, the solvent was removed. The residue was dissolved in ethyl acetate and washed with saturated sodium bicarbonate and brine successively. The dried organic layer was evaporated and the residue was dissolved in methanol (20 ml), and to this solution was added conc. hydrochloric acid (0.7 ml) at ambient temperature. After stirring for 2 hours at the same temperature, the solvent was removed, and the residue was dissolved in ethyl acetate and then washed with saturated sodium bicarbonate and brine successively. The dried organic layer was evaporated and the obtained oil was crystallized from isopropyl ether to give (2S, 4R)-4-hydroxy-2-(imidazol-2-yl)-1-(4-nitrobenzyloxycarbonyl) pyrrolidine (1.0 g).

mp: 95°–97° C.

IR (Nujol): 1680–1690, 1605 cm$^{-1}$

NMR (DMSO-d$_6$, δ): 3.3–4.0 (3H, m), 4.3–4.6 (1H, m), 4.8–5.4 (4H, m), 6.99 (2H, s), 7.0–7.8 (2H, m), 8.0–8.4 (2H, m)

Preparation 50

To a solution of (2S,4R)-2-(imidazol-2-yl)-4-hydroxy-1- (4-nitrobenzyloxycarbonyl)pyrrolidine (1.0 g) in a mixture of water (10 ml) and tetrahydrofuran (20 ml) was dropwise added a solution of 4-nitrobenzyloxycarbonyl chloride (0.85 g) in tetrahydrofuran (5 ml) under ice-cooling with stirring, keeping the pH between 9 and 10 with 4N aqueous sodium hydroxide. The mixture was stirred under the same condition for 1 hour, extracted with ethyl acetate. The organic layer was washed with brine, dried over sodium sulfate and concentrated to give (2S, 4R)-4-hydroxy-2-[N-(4-nitrobenzyloxycarbonyl) imidazol-2-yl]-1-(4-nitrobenzyloxycarbonyl) pyrrolidine (970 mg).

IR (CH$_2$Cl$_2$): 1760, 1710, 1605 cm$^{-1}$

Preparation 51

(2S, 4R)-4-Methanesulfonyloxy-2-[N-(4-nitrobenzyloxycarbonyl) imidazol-2-yl]-1-(4-nitrobenzyloxycarbonyl)pyrrolidine (1.36 g) was obtained by reacting (2S, 4R)-4-hydroxy-2- [N-(4-nitrobenzyloxycarbonyl-)imidazol-2-yl]-1-(4-nitroenzyloxycarbonyl) pyrrolidine (970 mg) with methanesulfonyl chloride (0.28 ml) in substantially the same manner as that of Preparation 46.

IR (CH$_2$Cl$_2$): 1760, 1710, 1610 cm$^{-1}$

NMR (CDCl$_3$, δ): 3.06 (3H, s), 4.0–4.2 (2H, m), 5.1–5.6 (5H, m), 5.7–6.0 (1H, m), 6.9–7.7 (6H, m), 8.0–8.4 (4H, m)

Preparation 52

(2S, 4S)-4-Acetylthio-2-(imidazol-2-yl)-1-(4-nitrobenzyloxycarbonyl) pyrrolidine (750 mg) was obtained by reacting (2S, 4R)-4-methanesulfonyloxy-2-[N-(4-nitrobenzyloxycarbonyl) imidazol-2-yl]-1-(4-nitrobenzyloxycarbonyl)pyrrolidine with thioacetic S-acid in substantially the same manner as that of Preparation 6-1).

IR (CH$_2$Cl$_2$) 1690–1710, 1605 cm$^{-1}$

NMR (CDCl$_3$, δ): 2.30 (3H, s), 3.8–4.3 (2H, m), 4.8–5.4 (3H, m), 6.98 (2H, br s), 7.42 (2H, d, J=8 Hz), 8.17 (2H, d, J=8 Hz)

Preparation 53-1)

(2S, 4S)-4-Mercapto-1-(4-nitrobenzyloxycarbonyl)-2-(1,2,4-oxadiazol-5-yl)pyrrolidine (960 mg) was obtained by reacting (2S, 4S)-1-(4-nitrobenzyloxycarbonyl)-2-(1,2,4-oxadiazol-5-yl)-4-(tritylthio)pyrrolidine with silver nitrate and potassium iodide successively in substantially the same manner as that of Preparation 24-10).

IR (CH$_2$Cl$_2$): 1705, 1605, 1580 cm$^{-1}$

NMR (CDCl$_3$, δ): 2.7–3.1 (1H, m), 3.2–3.7 (2H, m), 4.9–5.4 (3H, m), 7.2–7.8 (2H, m), 8.1–8.3 (2H, m), 8.37 (1H, s)

Preparation 53-2)

(2S, 4S)-4-Mercapto-1-(4-nitrobenzyloxycarbonyl)-2-[2- (ureidomethyl)thiazol-4-yl]pyrrolidine (1.2 g) was obtained by reacting (2S ,4S)-4-acetylthio-1-(4- nitrobenzyloxycarbonyl)-2-[2-(ureidomethyl)thiazol-4-yl]-pyrrolidine with 28% solution of sodium methoxide in methanol in substantially the same manner as that of Preparation 7-1).

IR (CH$_2$Cl$_2$): 3300–3400, 1670–1700, 1605 cm$^{-1}$

NMR (CDCl$_3$, δ): 4.51 (2H, d, J=6 Hz), 4.6–5.4 (5H, m), 5.6–5.9 (1H, m), 6.9–7.7 (3H, m), 8.0–8.3 (2H, m)

Preparation 53-3)

(2S, 4S)-2-(4-Azidomethylthiazol-2-yl)-4-mercapto1-(4-nitrobenzyloxycarbonyl)pyrrolidine (430 mg) was obtained by reacting (2S, 4S)-4-acetylthio-2-(4-azidomethylthiazol-2-yl) -1-(4-nitrobenzyloxycarbonyl)pyrrolidine with 28% solution of sodium methoxide in methanol in substantially the same manner as that of Preparation 7-1).

IR (CH$_2$Cl$_2$) 2200 , 1710, 1605 cm$^{-1}$

NMR (CDCl$_3$, δ): 4.48 (2H, s), 5.1–5.4 (3H, m), 7.20 (1H, s), 7.1–7.7 (2H, m), 8.1–8.4 (2H, m)

Preparation 53-4)

(2S, 4S)-2-(Imidazol-2-yl)-4-mercapto-1-(4-nitrobenzyloxycarbonyl) pyrrolidine (570 mg) was obtained by reacting (2S, 4S)-4-acetylthio-2-(imidazol-2-yl) -1-(4-nitrobenzyloxycarbonyl)pyrrolidine with 28% solution of sodium methoxide in methanol in substantially the same manner as that of Preparation 7-1).

IR (CH$_2$Cl$_2$): 1690–1710, 1605 cm$^{-1}$

NMR (THF-d$_6$, δ): 3.8–4.3 (2H, m), 4.9–5.4 (3H, m), 6.97 (2H, s) , 7.0–7.8 (2H, m), 8.0–8.4 (2H, m)

EXAMPLE 1

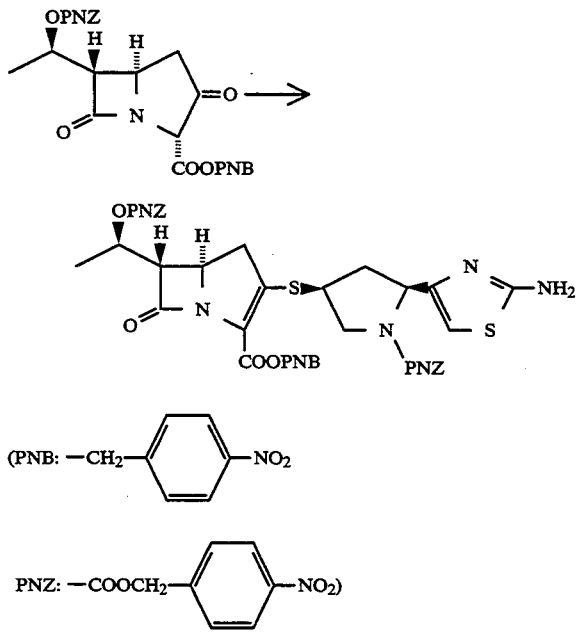

To a solution of 4-nitrobenzyl (2R,5R,6S)-6-[(1R)-1-(4-nitrobenzyloxycarbonyloxy)ethyl]-3,7-dioxo-1-azabicyclo[3.2.0]heptane-2-carboxylate (1.92 g) in dichloromethane (50 ml) were added N,N-diisopropyl-N-ethylamine (0.76 ml) and trifluoromethanesulfonic anhydride (0.73 ml) at −30° C., and the solution was stirred at the same temperature for 30 minutes. To this solution was added (2S, 4S)-2-(2-aminothiazol-4-yl)-4-mercapto-1- (4-nitrobenzyloxycarbonyl)pyrrolidine (1.13 g) in dichloromethane (20 ml) at −30° C. and the solution was stirred at 0° C. for 3 hours. The mixture was washed in turn with water and brine, dried over magnesium sulfate, and evaporated in vacuo. The oily residue was chromatographed on silica gel (60 g) eluting with a mixture of dichloromethane and acetone (5:1 V/V) to give 4-nitrobenzyl (5R,6S)-3-[(2S,4S)-2-(2-aminothiazol-4-yl) -1-(4-nitrobenzyloxycarbonyl)pyrrolidin-4-ylthio]-6-[(1R)-1-(4-nitrobenzyloxycarbonyloxy) ethyl]-7-oxo-1-azabicyclo[3.2.0]hept-2-ene-2-carboxylate (1.85 g).

IR (Nujol): 3300–3500, 1780, 1720, 1690–1720, 1610, 1520 cm$^{-1}$

NMR (CDCl$_3$, δ): 1.41 (3H, d, J=7 Hz), 2.0–3.02 (2H, m), 3.0–4.0 (6H, m), 4.0–4.4 (2H, m), 4.7–5.7 (9H, m), 6.22 (1H, br s), 7.2–7.8 (6H, m), 8.0–8.3 (6H, m)

EXAMPLE 2-1)

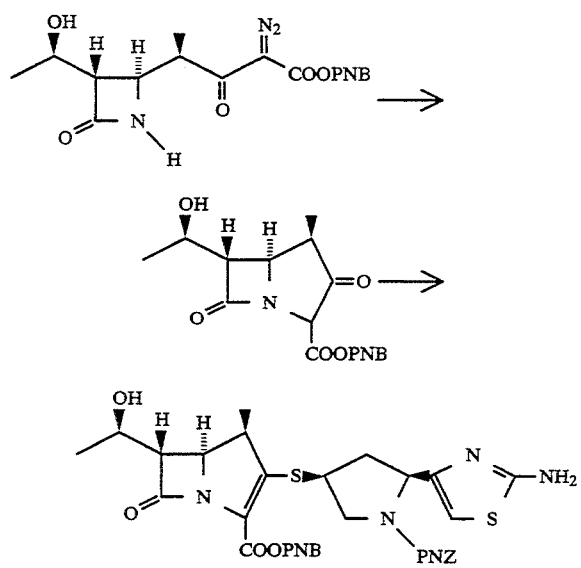

To a solution of 4-nitrobenzyl (4R)-2-diazo-4-[(2R, 3S)-3-{(1R)-1-hydroxyethyl}-4-oxoazetidin-2-yl]-3-oxopentanoate (1.0 g) in dichloroethane (50 ml) was added rhodium (II) acetate (2 mg) under refluxing. After refluxing for 1 hour, the reaction mixture was evaporated in vacuo to give a residue. The residue was dissolved in anhydrous benzene (10 ml) and then evaporated. This operation was repeated once again to give 4-nitrobenzyl (4R, 5R, 6S)-6-[(1R)-1-hydroxyethyl]-4-methyl-3, 7-dioxo-1-azabicyclo[3.2.0]heptane-2-carboxylate. The compound obtained above was dissolved in anhydrous acetonitrile (20 ml) and cooled to 0° C. under an atmosphere of nitrogen. To this solution were added N,N-diisopropyl-N-ethylamine (0.59 ml) and diphenyl phosphorochloridate (0.61 ml) successively, and the solution was stirred at 0°–5° C. for 40 minutes. To the resulting solution were added a solution of (2S, 4S)-2-(2-aminothiazol-4-yl)-4-mercapto-1-(4-nitrobenzyloxycarbonyl) pyrrolidine (1.07 g) in acetonitrile and N,N-diisopropyl-N-ethylamine (0.59 ml) and the stirring was continued at the same temperature for 2 hours. The reaction mixture was poured into ethyl acetate (60 ml) and washed with 0.1N hydrochloric acid, saturated aqueous sodium bicarbonate and brine successively. The dried organic layer was evaporated and the oily residue was chromatographed on silica gel (60 g) eluting with a mixture of dichloromethane and acetone (5:2 V/V) to give 4-nitrobenzyl (4R, 5S, 6S )-3- [(2S, 4S)-2-(2-aminothiazol-4-yl)-1-(4-nitrobenzyloxycarbonyl) pyrrolidin-4-ylthio]-6-[(1R)-1-hydroxyethyl]-4-methyl-7-oxo-1-azabicyclo [3.2.0]hept-2-ene-2-carboxylate (900 mg).

IR (CHCl$_3$): 3500, 3400, 1765, 1705, 1600, 1510 cm$^{-1}$

NMR (CDCl$_3$, δ): 1.27 (3H, d, J=6 Hz), 1.36 (3H, d, J=7 Hz) , 2.15 (3H, s) , 3.2–4.5 (8H, m), 4.7–5.7 (5H, m), 6.24 (1H, m), 7.1–8.4 (8H, m)

EXAMPLE 2—2)

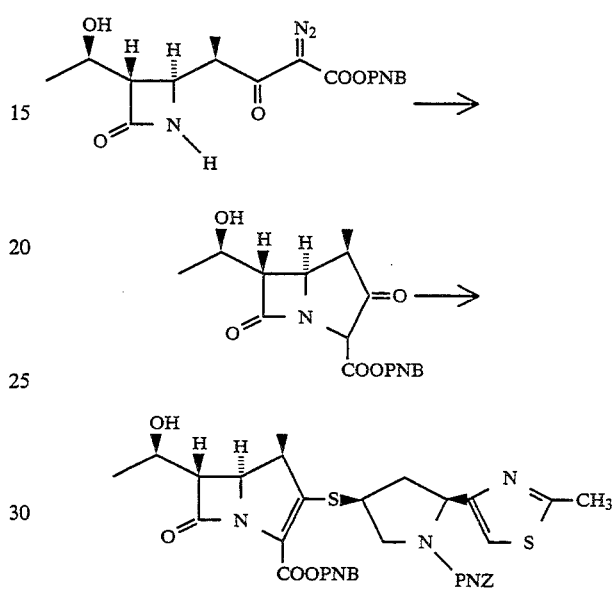

4-Nitrobenzyl (4R,5S ,6S)-6-[(1R)-1-hydroxyethyl]-4-methyl-3- [(2S, 4S )-2-(2-methylthiazol-4-yl)-1-(4-nitrobenzyloxycarbonyl) pyrrolidin-4-ylthio]-7-oxo-1-azabicyclo [3.2.0]hept-2-ene-2-carboxylate (790 mg) was obtained by reacting 4-nitrobenzyl (4R)-2-diazo-4-[(2R, 3S)-3-{(1R)-1-hydroxyethyl}-4-oxoazetidin-2-yl]-3-oxopentanoate (583 mg) with catalytic amount of rhodium(II) acetate and then with (2S,4S)-4-mercapto-2-(2-methylthiazol-4-yl) -1-(4-nitrobenzyloxycarbonyl)-pyrrolidine (566 mg) in substantially the same manner as that of Example 2-1).

IR (CHCl$_3$): 3200–3600, 1765, 1710, 1610 cm$^{-1}$

NMR (CDCl$_3$, δ): 1.2–1.7 (6H, m) , 2.68 (3H, s), 3.0–4.5(7H, m), 4.8–5.7 (6H, m), 6.8–8.6 (9H, m)

EXAMPLE 2-3)

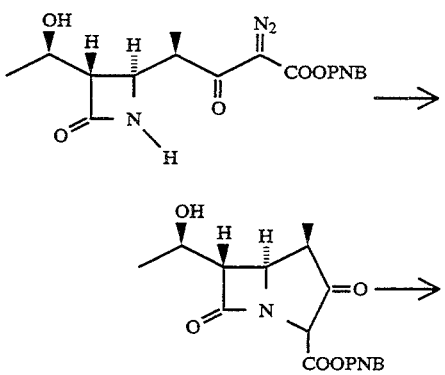

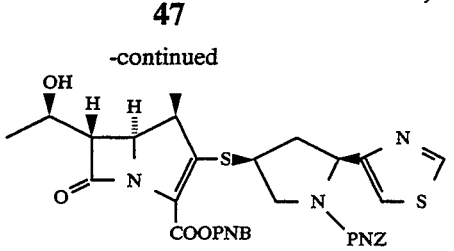

4-Nitrobenzyl (4R, 5S, 6S)-6-[(1R)-1-hydroxyethyl]-4-methyl-3- [(2S, 4S)-1-(4-nitrobenzyloxycarbonyl)-2-(thiazol-4-yl) pyrrolidin-4-ylthio]-7-oxo-1-azabicyclo-[3.2.0]hept-2-ene-2-carboxylate (760 mg) was obtained by reacting 4-nitrobenzyl (4R)-2-diazo-4-[(2R,3S)-3-{(1R) -1-hydroxyethyl}-4-oxoazetidin-2-yl]-3-oxopentanoate (820 mg) with catalytic amount of rhodium (II) acetate and then with (2S, 4S)-4-mercapto-1-(4-nitrobenzyloxycarbonyl) -2-(thiazol-4-yl)pyrrolidine (850 mg) in substantially the same manner as that of Example 2-1).

IR (Neat): 3300–3600, 1770, 1680–1720, 1610 cm$^{-1}$

NMR (CDCl$_3$, δ): 1.1–1.6 (6H, m), 3.8–4.4 (3H, m), 4.8–5.7 (6H, m), 8.0–8.3 (4H, m), 8.8 (1H, br s)

EXAMPLE 2-4)

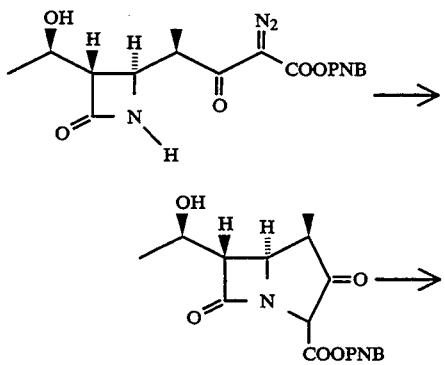

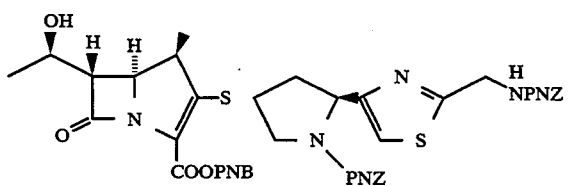

4-Nitrobenzyl (4R, 5S, 6S)-6-[(1R)-1-hydroxyethyl]-4-methyl-3- [(2S, 4S)-1-(4-nitrobenzyloxycarbonyl)-2-[2-{N-(4-nitrobenzyloxycarbonyl)aminomethyl}thiazol-4-yl]- pyrrolidin-4-ylthio]-7-oxo-1-azabicyclo[3.2.0]hept-2-ene-2-carboxylate (400 mg) was obtained by reacting 4-nitrobenzyl (4R)-2-diazo-4-[(2R,3S)-3-{(1R)-1-hydroxyethyl}-4-oxoazetidin-2-yl]-3-oxopentanoate (300 mg) with catalytic amount of rhodium (II) acetate and then with (2S, 4S)-4-mercapto-1-(4-nitrobenzyloxycarbonyl)-2-[2-{N-(4-nitrobenzyloxycarbonyl)aminomethyl}thiazol-4-yl]pyrrolidine (500 mg) in substantially the same manner as that of Example 2-1).

IR (CHCl3): 3450, 1760, 1700, 1600, 1500 cm$^{-1}$

NMR (CDCl$_3$, δ): 1.1–1.4 (6H, m), 3.2–3.8 (4H, m), 3.8–4.5 (3H m) 4.63 (2H, d, J=7 Hz), 4.8–5.9 (7H, m), 6.8–7.8 (7H, m), 7.9–8.3 (6H, m)

EXAMPLE 2-5)

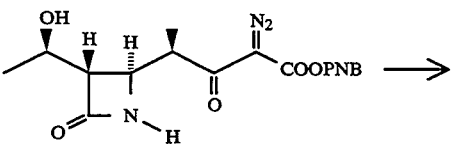

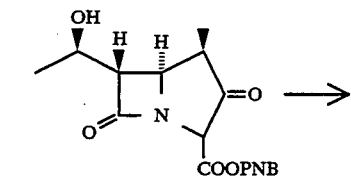

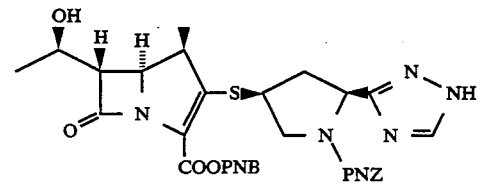

4-Nitrobenzyl (4R, 5S, 6S)-6-[(1R)-1-hydroxyethyl]-4-methyl-3- [(2S, 4S)-1-(4-nitrobenzyloxycarbonyl)-2(1H-1,2,4-triazol-3-yl) pyrrolidin-4-ylthio]-7-oxo-1azabicyclo [3.2.0]hept-2-ene-2-carboxylate (1.02 g) was obtained by reacting 4-nitrobenzyl (4R)-2-diazo-4-[(2R, 3S)-3-{(1R)-1-hydroxyethyl}-4-oxoazetidin-2-yl]-3-oxopentanoate (1.0 g) with catalytic amount of rhodium (II) acetate and then with (2S,4S)-4-mercapto-1-(4-nitrobenzyloxycarbonyl)-2-(1H-1,2,4-triazol-3-yl)pyrrolidine (1.06 g) in substantially the same manner as that of Example 2-1).

IR (Nujol): 1760–1780, 1700, 1603, 1515 cm$^{-1}$

NMR (CDCl$_3$, δ): 1.1–1.4 (6H, m) , 3.1–4.4 (8H, m), 5.0–5.6 (5H, m), 7.0–7.8 (5H, m), 7.9–8.3 (4H, m)

EXAMPLE 2-6)

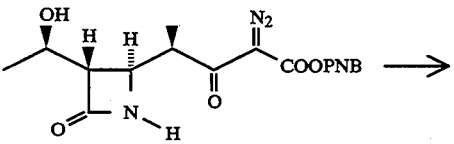

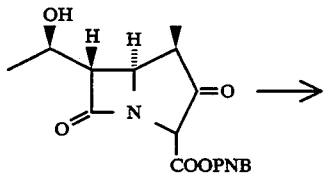

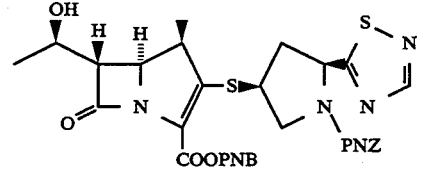

4-Nitrobenzyl (4R,5S ,6S)-6-[(1R)-1-hydroxyethyl]-4-methyl- 3- [(2S, 4S)-1-(4-nitrobenzyloxycarbonyl)-2-(1, 2,4-thiadiazol-5-yl) pyrrolidin-4-ylthio]-7-oxo-1-azabicyclo [3.2.0]hept-2-ene-2-carboxylate (630 mg) was obtained by reacting 4-nitrobenzyl (4R)-2-diazo-4-[(2R, 3S)-3-{(1R)-1-hydroxyethyl}-4-oxoazetidin-2-yl]-

3-oxopentanoate (556 mg) with catalytic amount of rhodium(II) acetate and then with (2S,4s)-4-mercapto-1-(4-nitrobenzyloxycarbonyl) -2-(1,2,4-thiadiazol-5-yl)pyrrolidine (460 mg) in substantially same manner as that of Example 2-1).

IR (Nujol): 1765, 1685–1715, 1608, 1515 cm$^{-1}$

NMR (CDCl$_3$, δ): 1.1–1.5 (6H, m), 4.0–4.4 (3H, m), 5.0–5.6 (6H, m), 7.2–7.7 (4H, m), 8.0–8.3 (4H, d, J=9 Hz), 8.56 (1H, s)

EXAMPLE 3

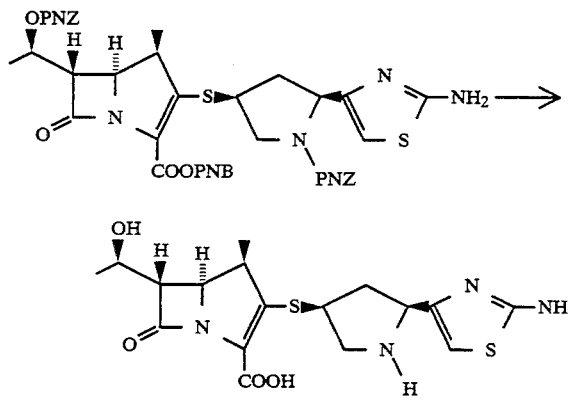

A mixture of 4-nitrobenzyl (5R,6S)-3-[(2S,4S)-2-(2-aminothiazol-4-yl)-1-(4-nitrobenzyloxycarbonyl) pyrrolidin-4-ylthio]-6-[(1R)-1-(4-nitrobenzyloxycarbonyloxy) ethyl]-7-oxo-1-azabicyclo[3.2.0]hept-2-ene-2-carboxylate (1.85 g), 20% palladium hydroxide on carbon (500 mg), 0.05M phosphate buffer (pH 6.5, 30 ml) and tetrahydrofuran (50 ml) was stirred at room temperature for 4 hours under atmospheric pressure of hydrogen. After the catalyst was filtered off, the filtrate was concentrated to remove the organic solvent. The residue was washed with ethyl acetate, adjusted to pH 6.2 with aqueous potassium carbonate and concentrated to remove the organic solvent. The residue was chromatographed on nonionic adsorption resin "Diaion HP-20" (Trademark, made by Mitsubishi Chemical Industries) (60 ml) eluting in turn with water (300 ml) and 5% aqueous acetone (200 ml). The fractions containing the desired compound were collected and lyophilized to give (5R,6S)-3-[(2S,4S)-2-(2-aminothiazol-4-yl) pyrrolidin-4-ylthio]-6-[(1R)-1-hydroxyethyl]-7-oxo-1-azabicyclo [3.2.0]hept-2-ene-2-carboxylic acid (540 mg).

Mass: 397 (M$^+$+1)

IR (KBr): 3100–3600, 1740–1760, 1590 cm$^{-1}$

NMR (D$_2$O, δ): 2.27 (3H, d, J=7 Hz), 2.1–2.3 (2H, m), 2.8–4.3 (12H, m)

EXAMPLE 4-1)

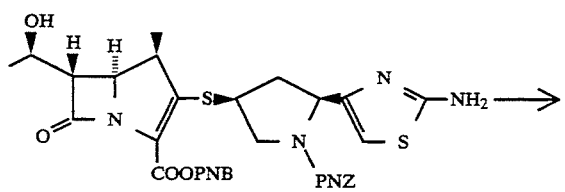

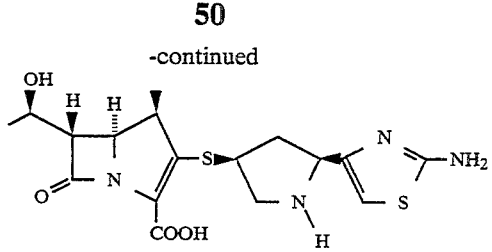

A mixture of 4-nitrobenzyl (4R,5S,6S)-3-[(2S,4S)-2-(2-aminothiazol-4-yl)-1-(4-nitrobenzyloxycarbonyl)-pyrrolidin-4-ylthio]-6-[(1R)-1-hydroxyethyl]-4-methyl-7-oxo-1-azabicyclo [3.2.0]hept-2-ene-2-carboxylate (900 mg), 20% palladium hydroxide on carbon (350 mg), 0.05M phosphate buffer (pH 6.5, 20 ml) and tetrahydrofuran (30 ml) was stirred at room temperature for 3 hours under atmospheric pressure of hydrogen. After the catalyst was filtered off, the filtrate was concentrated to remove the organic solvent. The residue was washed with ethyl acetate, adjusted to pH 6.2 with aqueous potassium carbonate and concentrated in vacuo to remove the organic solvent. The residue was chromatographed on nonionic adsorption resin "Diaion HP-20" (Trademark, made by Mitsubishi Chemical Industries) (60 ml) eluting in turn with water (250 ml) and 5–7% aqueous acetone (200 ml). The fractions containing the desired compound were collected and lyophilized to give (4R,5S,6S)-3-[(2S,4S)-2-(2-aminothiazol-4-yl) -pyrrolidin-4-ylthio]-6-[(1R)-1-hydroxyethyl]-4-methyl-7-oxo-1-azabicyclo [3.2.0]hept-2-ene-2-carboxylic acid (233 mg).

Mass: 411 (M$^+$+1)

IR (KBr): 3100–3600, 1730–1760, 1510–1600 cm$^{-1}$

NMR H$_2$O, δ): 1.22 (3H, d, J=8 Hz), 1.28 (3H, d, J=7 Hz), 1.6–2.3 (2H, m), 2.8–3.0 (1H, m), 3.3–3.6 (3H, m), 3.7–3.9 (1H, m), 4.0–4.3 (2H, m), 6.80 (1H, s)

EXAMPLE 4-2)

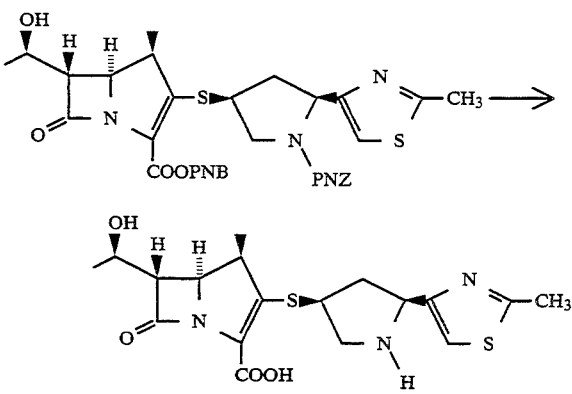

(4R, 5S, 6S)-6-[(1R)-1-Hydroxyethyl]-4-methyl-3-[(2S, 4S)-2-(2-methylthiazol-4-yl)pyrrolidin-4-ylthio]-7-oxo-1-azabicyclo [3.2.0]hept-2-ene-2-carboxylic acid (143 mg) was obtained by hydrogenating 4-nitrobenzyl (4R, 5S, 6S)-6-[(1R)-1-hydroxyethyl]-4-methyl-3-[(2S, 4S)-2-(2-methylthiazol-4-yl)-1-(4-nitrobenzyloxycarbonyl) pyrrolidin-4-ylthio]-7-oxo-1-azabicyclo-[3.2.0]hept-2-ene-2-carboxylate (790 mg) in substantially the same manner as that of Example 4-1).

mp: 185°–196° C.

Mass: 410 (M$^+$+1)

IR (KBr): 3000–3500, 1730–1760, 1570–1590 cm$^{-1}$

NMR (D₂O, δ): 1.22 (3H, d, J=7 Hz), 1.31 (3H, d, J=7 Hz) 2.2–2.5 (1H, m), 2.71 (3H, s), 2.8–3.2 (1H, m), 3.3–4.4 (5H, m), 7.53 (1H, s)

EXAMPLE 4-3

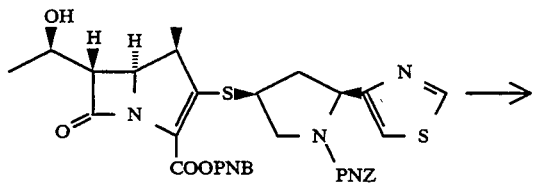

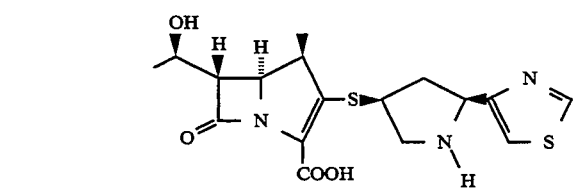

(4R, 5S, 6S)-6-[(1R)-1-Hydroxyethyl]-4-methyl-7-oxo-3-[(2S, 4S)-2-(thiazol-4-yl)pyrrolidin-4-ylthio]-1-azabicyclo[3.2.0]hept-2-ene-2-carboxylic acid (169 mg) was obtained by hydrogenating 4-nitrobenzyl (4R,5S,6S)-6-[(1R)-1-hydroxyethyl]-4-methyl-3-[(2S,4S)-1-(4-nitrobenzyloxycarbonyl)-2-(thiazol-4-yl)pyrrolidin-4-ylthio]-7-oxo-1-azabicyclo[3.2.0]hept-2-ene-2-carboxylate (760 mg) in substantially the same manner as that of Example 4-1).

mp: 175°–179° C.
Mass: 396 (M⁺+1)
IR (KBr): 3000–3400, 1730–1760, 1590 cm⁻¹
NMR (D₂O, δ): 1.22 (3H, d, J=7 Hz), 1.32 (3H, d, J=6 Hz), 2.2–2.6 (1H, m), 2.7–4.4 (8H, m), 7.8 (1H, d, J=2 Hz), 9.09 (1H, d, J=2 Hz)

EXAMPLE 4—4)

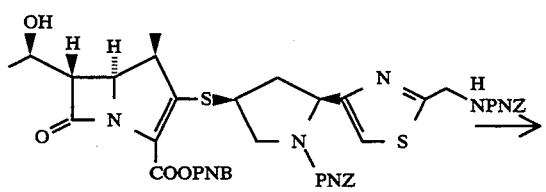

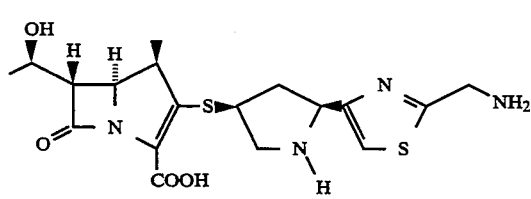

(4R, 5S, 6S)-3-[(2S, 4S)-2-{2-(Aminomethyl)thiazol-4-yl}pyrrolidin-4-ylthio]-6-[(1R)-1-hydroxyethyl]-4-methyl-7-oxo-1-azabicyclo[3.2.0]hept-2-ene-2-carboxylic acid (50 mg) was obtained by hydrogenating 4-nitrobenzyl (4R, 5S, 6S)-6-[(1R)-1-hydroxyethyl]-4-methyl-3-[(2S,4S)-1-(4-nitrobenzyloxycarbonyl)-2-[2-{N-(4-nitrobenzyloxycarbonyl) aminomethyl}thiazol-4-yl]-pyrrolidin-4-ylthio]-7-oxo-1-azabicyclo[3.2.0]-hept-2-ene-2-carboxylate (400 mg) in substantially the same manner as that of Example 4-1).

Mass: 425 (M⁺+1)
IR (KBr): 2900–3500, 1730–1760, 1580 cm⁻¹

NMR (D₂O, δ): 1.21 (3H, d, J=7 Hz), 1.26 (3H, d, J=6 Hz), 2.2–2.5 (1H, m), 2.5–3.1 (2H, m), 7.61 (1H, s)

EXAMPLE 4-5)

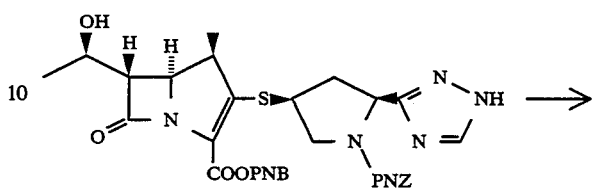

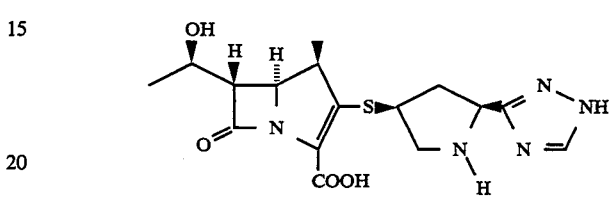

(4R, 5S, 6S)-6-[(1R)-1-Hydroxyethyl]-4-methyl-7-oxo-3-[(2S, 4S)-2-(1H-1,2,4-triazol-3-yl)pyrrolidin-4-ylthio]-1-azabicyclo[3.2.0]hept-2-ene-2-carboxylic acid (344 mg) was obtained by hydrogenating 4-nitrobenzyl (4R, 5S, 6S)-6-[(1R)-1-hydroxyethyl]-4-methyl-3-[(2S, 4S)-1-(4-nitrobenzyloxycarbonyl)-2-(1H-1,2,4-triazol-3-yl)-pyrrolidin-4-ylthio]-7-oxo-1-azabicyclo[3.2.0-]hept-2-ene-2-carboxylate (1.02 g) in substantially the same manner as that of Example 4-1).

Mass: 380 (M⁺+1)
IR (KBr): 3100–3500, 1730–1760, 1580 cm⁻¹
NMR (D₂O, δ): 1.19 (3H, d, J=7 Hz), 1.28 (3H, d, J=6 Hz), 2.1–2.5 (2H, m), 8.50 (1H, s)

EXAMPLE 4-6)

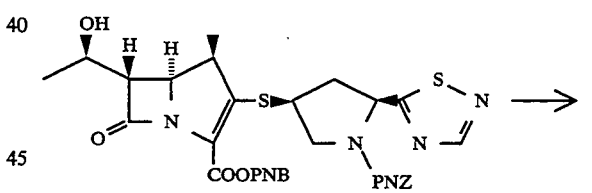

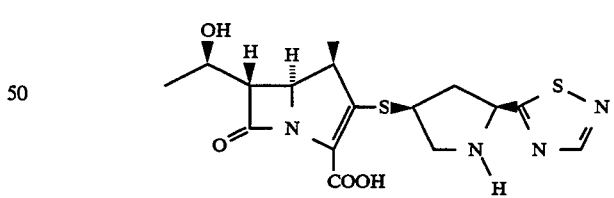

(4R, 5S, 6S)-6-[(1R)-1-Hydroxyethyl]-4-methyl-7-oxo-3-[(2S, 4S)-2-(1,2,4-thiadiazol-5-yl)pyrrolidin-4-ylthio]-1-azabicyclo[3.2.0]hept-2-ene-2-carboxylic acid (160 mg) was obtained by hydrogenating 4-nitrobenzyl (4R, 5S, 6S)-6-[(1R)-1-hydroxyethyl]-4-methyl-3-[(2S, 4S)-1-(4-nitrobenzyloxycarbonyl)-2-(1,2,4-thiadiazol-5-yl) pyrrolidin-4-ylthio]-7-oxo-1-azabicyclo[3.2.0]-hept-2-ene-2-carboxylate (630 mg) in substantially the same manner as that of Example 4-1).

IR (KBr): 3500–3300, 1745–1725, 1640, 1590 cm⁻¹
NMR (D₂O, δ): 1.21 (3H, d, J=7 Hz), 1.27 (3H, d, J=6 Hz), 1.8–2.2 (1H, m), 2.8–3.2 (3H, m), 3.2–3.7 (4H, m), 8.71 (1H, s)

EXAMPLE 5-1)

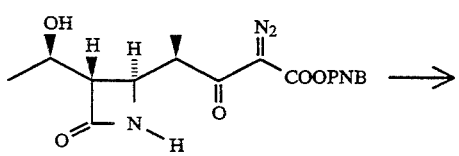

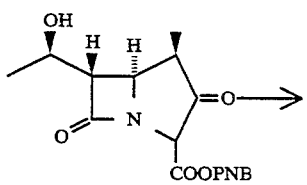

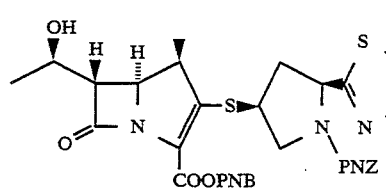

4-Nitrobenzyl (4R, 5S, 6S)-6- [(1R)-1-hydroxyethyl]4-methyl-3- [(2S, 4S)-1-(4-nitrobenzyloxycarbonyl)-2-(2-thiazolin-2-yl) pyrrolidin-4-ylthio]-7-oxo-1-azabicyclo-[3.2.0]hept-2-ene-2-carboxylate (480 mg) was obtained by reacting 4-nitrobenzyl (4R)-2-diazo-4-[(2R,3S)-3-{(1R)-1-hydroxyethyl}-4-oxoazetidin-2-yl]-3-oxopentanoate (950 mg) with catalytic amount of rhodium(II) acetate and then with (2S, 4S)-4-mercapto-1-(4-nitrobenzyloxycarbonyl) -2-(2-thiazolin-2-yl)pyrrolidine (840 mg) in substantially the same manner as that of Example 2-1).

IR (CH$_2$Cl$_2$): 3400, 1770, 1710, 1630, 1610 cm$^{-1}$

NMR (CDCl$_3$, δ): 1.1–1.4 (6H, m), 4.87 (1H, t, J=7 Hz), 5.1–5.6 (4H, m), 7.3–7.8 (4H, m), 8.1–8.4 (4H, m)

EXAMPLE 5-2)

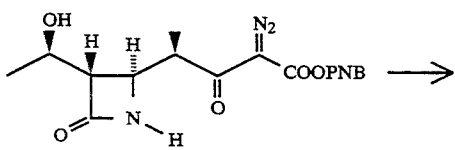

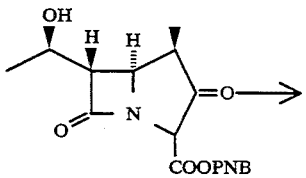

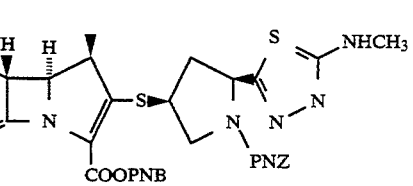

4-Nitrobenzyl (4R, 5S, 6S)-6-[(1R)-1-hydroxyethyl]-4-methyl-3-[(2S ,4S)-2-(5-(methylamino)-1,3,4-thiadiazol-2-yl}-1-(4-nitrobenzyloxycarbonyl)pyrrolidin-4-yl]thio-7-oxo-1-azabicyclo [3.2.0]hept-2-ene-2-carboxylate (0.97 g) was obtained by reacting 4-nitrobenzyl (4R)-2-diazo-4- [(2R, 3S)-3-{(1R)-1-hydroxyethyl}-4-oxoazetidin-2-yl]-3-oxopentenoate (0.80 g) with catalytic amount of rhodium (II) acetate and then with (2S, 4S)-4-mercapto-2- {5-(methylamino)-1,3,4-thiadiazol-2-yl}-1-(4-nitrobenzyloxycarbonyl) pyrrolidine (0.83 g) in substantially the same manner as that of Example 2-1).

mp: 94°–97° C.

IR (Nujol): 3400–3200, 1765, 1705 cm$^{-1}$

NMR (CDCl$_3$, δ): 1.28 (3H, d, J=6.5 Hz), 1.37 (3H, d, J=7 Hz), 3.00 (3H, s)

EXAMPLE 5-3)

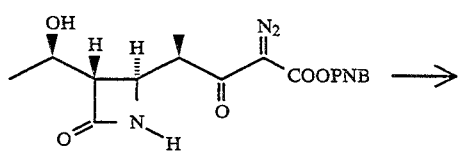

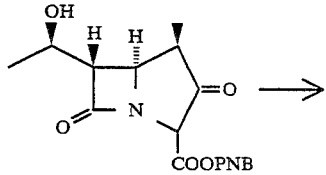

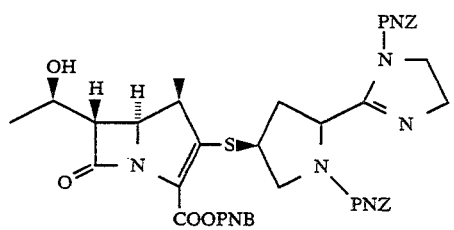

4-Nitrobenzyl (4R, 5S, 6S)-6-[(1R)-1-hydroxyethyl]-4-methyl-3- [(2S, 4S)-1-(4-nitrobenzyloxycarbonyl)-2-{1-(4-nitrobenzyloxycarbonyl)-2-imidazolin-2-yl}-pyrrolidin-4-yl]thio-7-oxo-1-azabicyclo[3.2.0]hept-2-ene-2-carboxylate (345 mg) was obtained by reacting 4-nitrobenzyl (4R) -2-diazo-4-[(2R, 3S)-3-{(1R)-1-hydroxyethyl}-4-oxoazetidin-2-yl]-3-oxopentanoate (460 mg) with catalytic amount of rhodium(II) acetate and then with (2S, 4S)-4-mercapto-1-(4-nitrobenzyloxycarbonyl)-2- [1-(4-nitrobenzyloxycarbonyl)-2-imidazolin-2-yl]-pyrrolidine (650 mg) in substantially the same manner as that of Example 2-1).

IR (CH$_2$Cl$_2$): 1765, 1710, 1605 cm$^{-1}$

NMR (CDCl$_3$, δ): 1.1–1.6 (6H, m), 5.1–5.6 (7H, m), 8.1–8.4 (6H, m)

EXAMPLE 5-4)

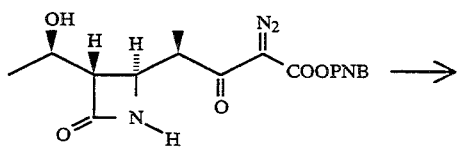

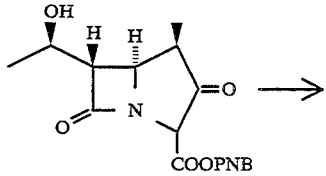

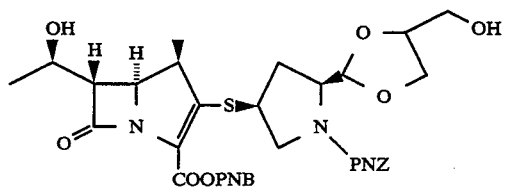

4-Nitrobenzyl (4R, 5S, 6S)-6-[(1R)-1-hydroxyethyl]-3-[(2S, 4S)-2-(4-hydroxymethyl-1,3-dioxolan-2-yl]-1-(4-nitrobenzyloxycarbonyl) pyrrolidin-4-yl]thio-4-methyl-7-oxo-1-azabicyclo [3.2.0]hept-2-ene-2-carboxylate (0.68 g) was obtained by reacting 4-nitrobenzyl (4R)-2-diazo-4-[(2R, 3S)-3-{(1R)-1-hydroxyethyl}-4-oxoazetidin-2-yl]-3-oxopentanoate (0.43 g) with catalytic amount of rhodium(II) acetate and then with (2S,4S)-2-(4-hydroxymethyl-1, 3-dioxolan-2-yl)-4-mercapto-1-(4-nitrobenzyloxycarbonyl) pyrrolidine (0.46 g) in substantially the same manner as that of Example 2-1).

IR (CH$_2$Cl$_2$): 1770, 1705 cm$^{-1}$

NMR (CDCl$_3$, δ): 1.33 (6H, t, J=6 Hz), 1.80–2.67 (3H, m), 3.10–4.40 (13H, m), 5.03–5.63 (2H, m), 5.22 (4H, s), 7.52 (2H, d, J=9 Hz), 7.63 (2H, d, J=9 Hz), 8.21 (4H, d, J=9 Hz)

EXAMPLE 5—5)

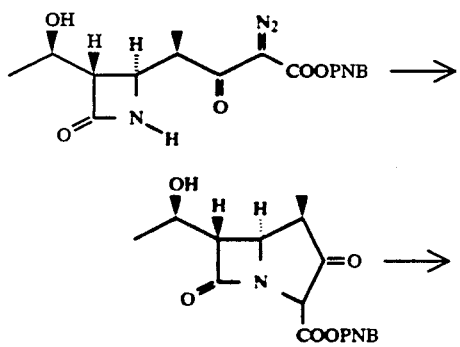

4-Nitrobenzyl (4R,5S, 6S)-3-[(2S ,4S)-2-(1,3-dithiolan-2-yl) -1-(4-nitrobenzyloxycarbonyl)pyrrolidin-4-yl]thio-6- [(1R)-1-hydroxyethyl]-4-methyl-7-oxo-1-azabicyclo-[3.2.0]hept-2-ene-2-carboxylate (1.60 g) was obtained by reacting 4-nitrobenzyl (4R)-2-diazo-4-[(2R,3S)-3-{(1R)-1-hydroxyethyl}-4-oxoazetidin-2-yl]-3-oxopentanoate (0.82 g) with catalytic amount of rhodium(II) acetate and then with (2S,4S)-2-(1,3-dithiolan-2-yl)-4-mercapto-1- (4-nitrobenzyloxycarbonyl)pyrrolidine (0.97 g) in substantially the same manner as that of Example 2-1).

IR (Neat): 1775, 1700, 1665 cm$^{-1}$

NMR (CDCl$_3$, δ): 1.33 (6H, t, J=6.8 Hz), 1.83–4.47 (10H, m), 3.23 (4H, s), 5.10–5.50 (2H, m), 5.23 (2H, s), 5.30 (2H, s), 7.52 (2H, d, J=9 Hz), 7.65 (2H, d, J=9 Hz), 8.22 (2H, d, J=9 Hz)

EXAMPLE 5-6)

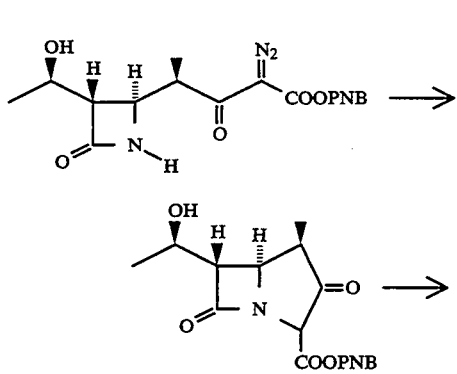

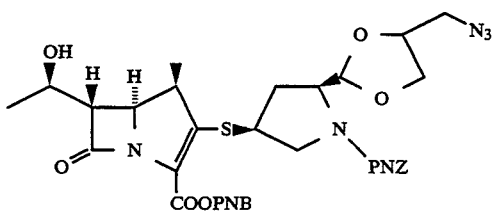

4-Nitrobenzyl (4R,5S,6S)-3-[(2S,4S)-2-(4-azidomethyl-1, 3-dioxolan-2-yl)-1-(4-nitrobenzyloxycarbonyl) pyrrolidin-4-yl]thio-6-[(1R)-1-hydroxyethyl]-4-methyl-7-oxo-1-azabicyclo [3.2.0]hept-2-ene-2-carboxylate (0.92 g) was obtained by reacting 4-nitrobenzyl (4R)-2-diazo-4-[(2R, 3S)-3-{(1R)-1-hydroxyethyl}-4-oxoazetidin-2-yl]-3-oxopentanoate (1.67 g) with catalytic amount of rhodium(II) acetate and then with (2S,4S)-2-(4-azidomethyl-1,3-dioxolan-2-yl) -4-mercapto-1-(4-nitrobenzyloxycarbonyl)pyrrolidine (0.94 g) in substantially the same manner as that of Example 2-1).

IR (CH$_2$Cl$_2$): 2100, 1770, 1705 cm$^{-1}$

NMR (CDCl$_3$, δ): 2.25 (3H, t, J=7.5 Hz), 2.31 (3H, t, J=7.2 Hz), 1.73–2.67 (3H, m), 2.87–4.63 (12H, m), 5.00–5.63 (2H, m), 5.22 (4H, s), 7.51 (2H, d, J=9 Hz), 7.64 (2H, d, J=9 Hz), 8.20 (4H, d, J=9 Hz)

EXAMPLE 5-7)

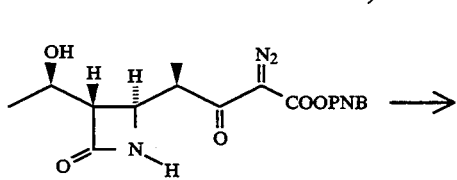

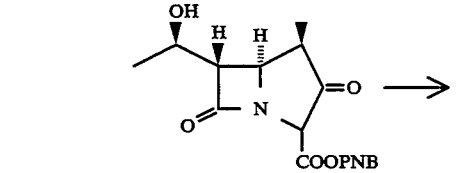

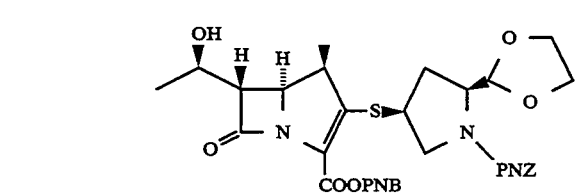

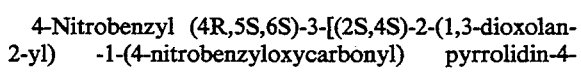

4-Nitrobenzyl (4R,5S,6S)-3-[(2S,4S)-2-(1,3-dioxolan-2-yl) -1-(4-nitrobenzyloxycarbonyl) pyrrolidin-4- yl]thio-6-[(1R)-1-hydroxyethyl]-4-methyl-7-oxo-1-azabicyclo [3.2.0]hept-2-ene-2-carboxylate (1.68 g) was obtained by reacting 4-nitrobenzyl (4R)-2-diazo-4- [(2R, 3S)-3-{(1R) -1-hydroxyethyl}-4-oxoazetidin-2-yl]-3-oxopentanoate (1.10 g) with catalytic amount of rhodium(II) acetate and then with (2S,4S)-2-(1,3-dioxolan-2-yl) -4-mercapto-1-(4-nitrobenzyloxycarbonyl)pyrrolidine (1.20 g) in substantially the same manner as that of Example 2-1).

IR (CH$_2$Cl$_2$): 1775, 1710 cm$^{-1}$

NMR (CDCl$_3$, δ): 1.32 (3H, t, J=7 Hz), 1.33 (3H, t, J=6 Hz), 1.80–2.67 (3H, m), 3.07–4.40 (11H, m), 5.07–5.63 (2H, m), 5.22 (4H, s), 7.50 (2H, d, J=9 Hz), 7.64 (2H, d, J=9 Hz), 8.20 (4H, d, J=9 Hz)

EXAMPLE 5-8)

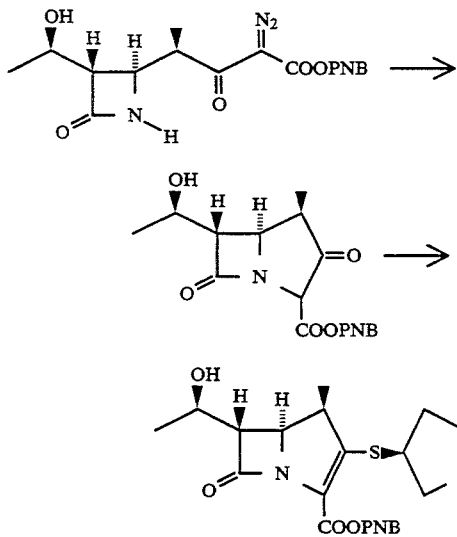

4-Nitrobenzyl (4R,5S,6S)-3-[(2S,4S)-2-(1,3-dithian-2-yl) -1-(4-nitrobenzyloxycarbonyl)pyrrolidin-4-yl]thio-6-[(1R)-1-hydroxyethyl]-4-methyl-7-oxo-1-azabicyclo [3.2.0]hept-2-ene-2-carboxylate (1.17 g) was obtained by reacting 4-nitrobenzyl (4R)-2-diazo-4-[(2R, 3S)-3-{(1R-1-hydroxyethyl}-4-oxoazetidin-2-yl]-3-oxopentanoate (1.10 g) with catalytic amount of rhodium(II) acetate and then with (2S,4S)-2-(1,3-dithian-2-yl) -4-mercapto-1-(4-nitrobenzyloxycarbonyl)pyrrolidine (1.36 g) in substantially the same manner as that of Example 2.

IR (CH$_2$Cl$_2$): 1775, 1710 cm$^{-1}$

NMR (CDCl$_3$, δ): 1.33 (3H, t, J=7 Hz), 1.34 (3H, t, J=6 Hz), 1.63–5.07 (17H, m), 5.10–5.67 (SH, m), 7.20 (2H, d, J=9 Hz), 7.65 (2H, d, J=9 Hz), 8.22 (4H, d, J=9 Hz)

EXAMPLE 5-9)

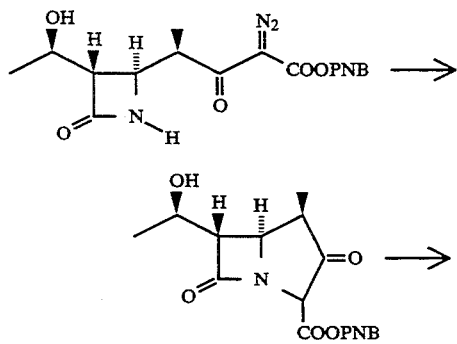

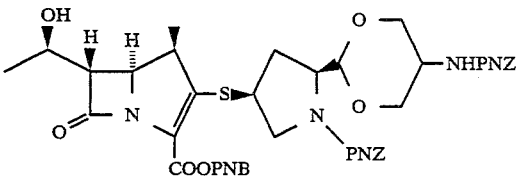

4-Nitrobenzyl (4R, 5S, 6S)-6-[(1R)-1-hydroxyethyl]-4-methyl-3-[(2S, 4S)-1-(4-nitrobenzyloxycarbomyl)-2-{5-(4-nitrobenzyloxycarbonylamino)-1,3-dioxan-2-yl}-pyrrolidin-4-yl]thio-7-oxo-1-azabicyclo[3.2.0]hept-2-ene-2-carboxylate (0.99 g) was obtained by reacting 4-nitrobenzyl (4R)-2-diazo-4-[(2R,3S)-3-{(1R)-1-hydroxyethyl}-4-oxoazetidin-2-yl]-3-oxopentanoate (0.61 g) with a catalytic amount of rhodium(II) acetate and then with (2S, 4S)-4-mercapto-1-(4-nitrobenzyloxycarbonyl) -2-[5-(4-nitrobenzyloxycarbonylamino)-1,3-dioxan-2-yl]pyrrolidine (0.97 g) in substantially the same manner as that of Example 2-1).

IR (CH$_2$Cl$_2$): 1770, 1720, 1705, 1520 cm$^{-1}$

NMR((CDCl$_3$, δ): 1.31 (3H, t, J=9.6 Hz), 1.32 (3H, t, J=8.6 Hz), 2.00–2.66 (3H, m), 3.17–4.42 (12H, m), 4.80–5.80 (3H, m), 5.22 (4H, s), 5.28 (2H, s), 7.48 (2H, d, J=6 Hz), 7.55 (2H, d, J=6 Hz), 7.68 (2H, d, J=6 Hz), 8.20 (6H, d, J=6 Hz)

EXAMPLE 5-10)

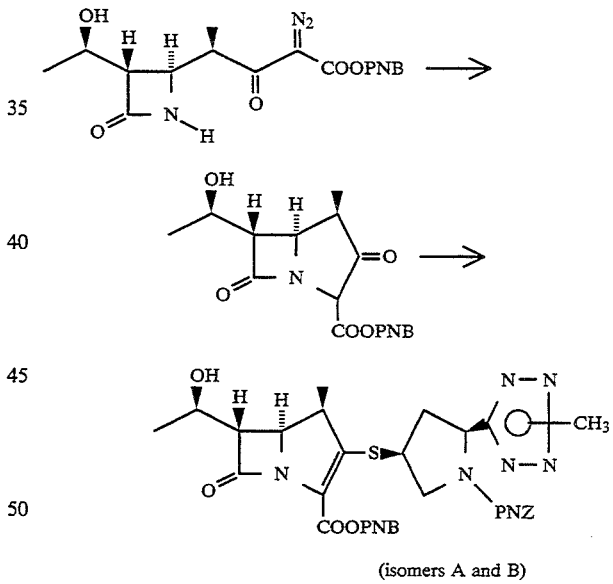

(isomers A and B)

To a solution of 4-nitrobenzyl (4R)-2-diazo-4-[(2R, 3S)-3-{(1R)-1-hydroxyethyl}-4-oxoazetidin-2-yl]-3-oxopentanoate (0.60 g) in 1,2-dichloroethane (15 ml) was added rhodium(II) acetate (2 mg) under reflux. The mixture was refluxed for 30 minutes under nitrogen atmosphere and concentrated under reduced pressure to give 4-nitrobenzyl (4R, 5S, 6S)-6-[(1R)-1-hydroxyethyl]-4-methyl-3, 7-dioxo-1-azabicyclo[3.2.0]heptane-2-carboxylate. The compound obtained above was dissolved in acetonitrile (15 ml) and N,N-diisopropyl-N-ethylamine (0.32 ml). Diphenyl phosphorochloridate (0.33 ml) was added thereto at −10°∫−5° C. in a nitrogen stream, followed by stirring at the same temperature for 30 minutes. To the solution were added N,N-diisopropyl-N-ethylamine (0.32 ml) and a solution of a mixture of (2S ,4S)-4-mercapto-2-(1-methyl-1H-tetrazol-5-yl) -1-(4-nitrobenzyloxycarbonyl)pyrrolidine and (2S, 4S)-4-mercapto-2-(2-methyl-2H-tetrazol-5-yl)-1-(4-nitrobenzyloxycarbonyl)pyrrolidine (0.55 g) in acetonitrile (2 ml) successively at −20° C. The mixture was stirred at the same temperature for 30 minutes and at 0°–10° C. for 3 hours. The mixture was poured into ethyl acetate (150 ml) and water (100 ml). The organic layer was separated, dried over magnesium sulfate and concentrated under reduced pressure to give a syrup. The syrup was subjected to a column chromatography on silica gel (20 g) and eluted with a mixture of acetone and dichloromethane (10: 90, V/V) to give 4-nitrobenzyl (4R,5S ,6S)-6-[(1R)-1-hydroxyethyl]-4-methyl-3-[(2S, 4S)-2{1(or 2)-methyl-1H(or 2H)-tetrazol-5-yl}-1-(4-nitrobenzyloxycarbonyl) pyrrolidin-4-yl]thio-7-oxo-1-azabicyclo [3.2.0]hept-2-ene-2-carboxylate (isomer A) (0.32 g).

TLC: Rf 0.4 (silica gel plate, developing solvent: acetone-dichloromethane=3:7, V/V)
IR (CHCl$_3$): 1770, 1705 cm$^{-1}$
NMR (CDCl$_3$, δ): 4.26 (3H, s)

And further, elution was carried out with a mixture of acetone and dichloromethane (20:80, V/V) to give 4-nitrobenzyl (4R, 5S ,6S)-6-[(1R)-1-hydroxyethyl]-4-methyl-3-[(2S,4S)-2-{2(or 1)-methyl-2H(or 1H)-tetrazol-5-yl}-1-(4-nitrobenzyloxycarbonyl)pyrrolidin-4-yl]thio-7-oxo-1-azabicyclo[3.2.0]hept-2-ene-2-carboxylate (isomer B) (0.35 g).

TLC: Rf 0.2 (silica gel plate, developing solvent: acetone-dichloromethane=3:7, V/V)
IR (CHCl$_3$): 1765, 1705 cm$^{-1}$
NMR (CDCl$_3$, δ): 4.1 (3H, br s)

EXAMPLE 5-11)

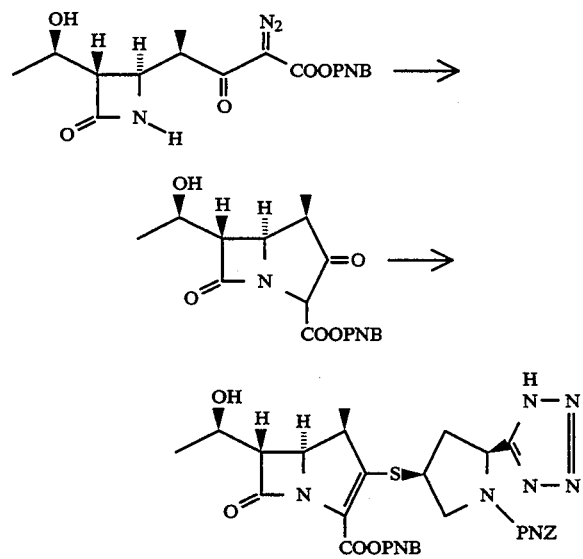

4-Nitrobenzyl (4R, 5S, 6 S)-6-[(1R)-1-hydroxyethyl]-4-methyl-3-[(2S, 4S)-2-(1H-tetrazol-5-yl)-1-(4-nitrobenzyloxycarbonyl) pyrrolidin-4-yl]thio-7-oxo-1-azabicyclo [3.2.0]hept-2-ene-2-carboxylate (0.30 g) was obtained by reacting 4-nitrobenzyl (4R)-2-diazo-4-[(2R, 3S)-3-{(1R)-1-hydroxyethyl}-4-oxoazetidin-2-yl]-3-oxopentanoate (0.60 g) with catalytic amount of rhodium (II) acetate and then with (2S, 4S)-4-mercapto-2-(1H-tetrazol-5-yl) -1-(4-nitrobenzyloxycarbonyl)pyrrolidine (0.54 g) in substantially the same m.anner as that of Example 2-1).

IR (Nujol): 1775–1690 cm$^{-1}$

EXAMPLE 6-1)

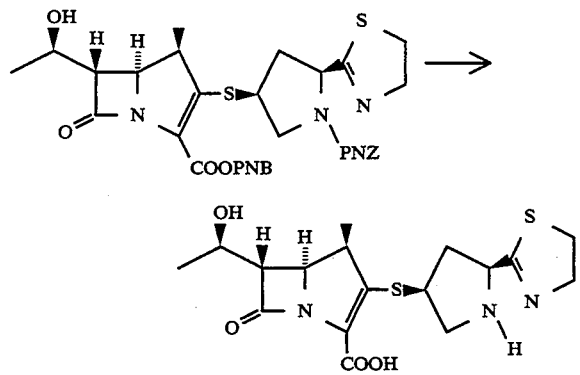

(4R, 5S, 6S)-6-[(1R)-1-Hydroxyethyl]-4-methyl-7-oxo-3-[(2S, 4S )-2-(2-thiazolin-2-yl)pyrrolidin-4-yl]-thio-1-azabicyclo [3.2.0]hept-2-ene-2-carboxylic acid (70 mg) was obtained by hydrogenating 4-nitrobenzyl (4R, 5S ,6S)-6-[(1R)-1-hydroxyethyl]-4-methyl-3-[(2S, 4S)- 1-(4-nitrobenzyloxycarbonyl)-2-(2-thiazolin-2-yl)-pyrrolidin-4-yl]thio-7-oxo-1-azabicyclo[3.2.0]hept-2-ene-2-carboxylate (480 mg) in substantially the same manner as that of Example 4-1).

mp: 125°–130 ° C.
IR (KBr): 3200–3400, 1740–1760, 1580–1595 cm$^{-1}$
NMR (D$_2$O, δ): 1.27 (6H, t, J=7 Hz),
SIMS: 398 (M$^+$+1)

EXAMPLE 6-2)

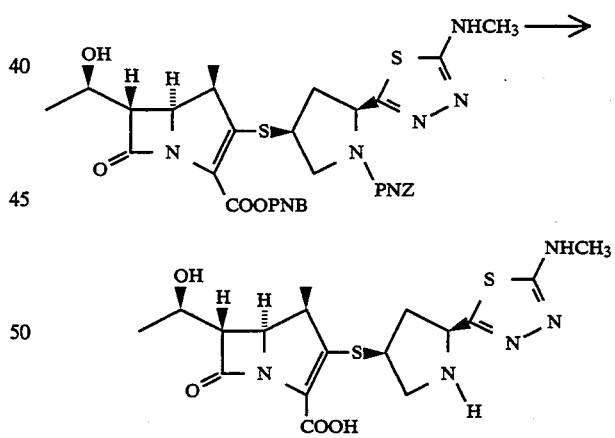

(4R, 5S, 6S)-6-[(1R)-1-Hydroxyethyl]-4-methyl-3-[(2S, 4S)-2-{5-(methylamino)-1,3,4-thiadiazol-2-yl}-pyrrolidin-4-yl]thio-7-oxo-1-azabicyclo[3.2.0]hept-2-ene-2-carboxylic acid (0.39 g) was obtained by hydrogenating 4-nitrobenzyl (4R, 5S, 6S)-6-[(1R)-1-hydroxyethyl]-4-methyl-3-[(2S, 4S)-2-{5-(methylamino)-1,3,4-thiadiazol-2-yl}-1-(4-nitrobenzyloxycarbonyl)pyrrolidin-4-yl]thio-7-oxo-1-azabicyclo[3.2.0]hept-2-ene-2-carboxylate (0.95 g) in substantially the same manner as that of Example 4-1).

mp: 190° C. (dec.)
IR (KBr): 1760–1730 cm$^{-1}$
NMR (D$_2$O, δ): 1.22 (3H, d, J=7.5 Hz), 1.29 (3H, d, J=8 Hz), 2.96 (3H, s)

SIMS: 464 (M++K), 426 (M++1), 369 (M+−56)

EXAMPLE 6-3)

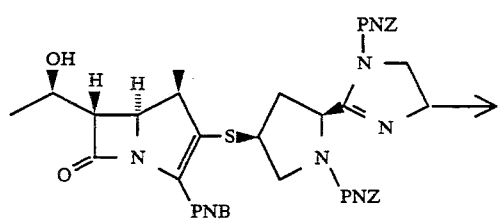

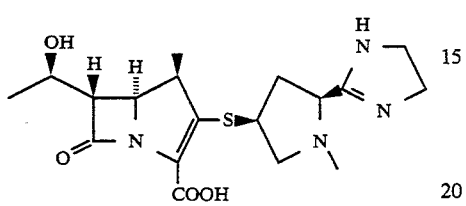

(4R,5S,6S)-3-[(2S, 4S)-2-(2-Imidazolin-2-yl)- pyrrolidin-4-ylthio]-6-[(1R)-1-hydroxyethyl]-4-methyl-7-oxo-1-azabicyclo [3.2.0]hept-2-ene-2-carboxylic acid (80 mg) was obtained by hydrogenating 4-nitrobenzyl (4R, 5S, 6S)-6-[(1R)-1-hydroxyethyl]-4-methyl-3- [(2S,4 S)-1-(4-nitrobenzyloxycarbonyl)-2-{1-(4-nitrobenzyloxycarbonyl)-2-imidazolin-2-yl}pyrrolidin-4-ylthio]-7-oxo-1-azabicyclo[3.2.0]hept-2-ene-2-carboxylate (340 mg) in substantially the same manner as that of Example 4-1).

IR (KBr): 3100–3400, 1730–1760 cm$^{-1}$

NMR (D$_2$O, δ): 1.1–1.4 (6H, t, J=7 Hz), 2.5–3.0 (2H, m), 3.92 (4H, s)

SIMS: 381 (M++1)

EXAMPLE 6-4)

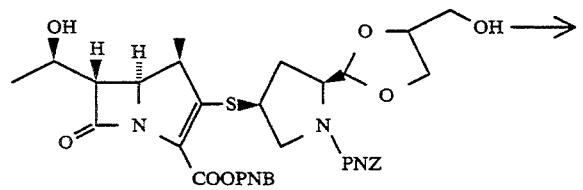

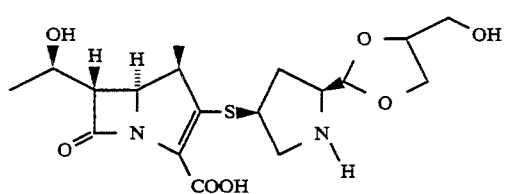

(4R,5S,6S)-6-[(1R)-1-Hydroxyethyl]-3-[(2S,4S)-2-(4-hydroxymethyl-1,3-dioxolan-2-yl)pyrrolidin-4-yl]- thio-4-methyl-7-oxo-1-azabicyclo[3.2.0]hept-2-ene-2-carboxylic acid (0.17 g) was obtained by hydrogenating 4-nitrobenzyl (4R, 5S, 6S)-6-[(1R)-1-hydroxyethyl]-3-[(2S, 4S)-2-(4-hydroxymethyl-1,3-dioxolan-2-yl)-1-(4-nitrobenzyloxycarbonyl) pyrrolidin-4-yl]thio-4-methyl-7-oxo-1-azabicyclo [3.2.0]hept-2-ene-2-carboxylate (0.67 g) in substantially the same manner as that of Example 4-1).

IR (Nujol): 1800–1695 cm$^{-1}$

NMR (D$_2$O, δ): 1.26 (6H, t, J=6.5 Hz)

EXAMPLE 6-5)

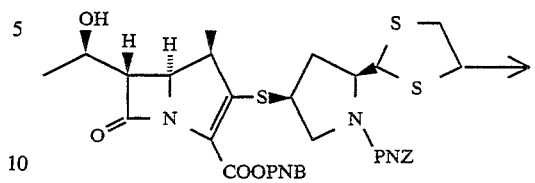

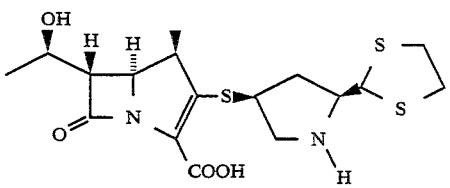

(4R,5S,6S)-3-[(2S,4S)-2-(1,3-Dithiolan-2-yl)-pyrrolidin-4-yl]thio-6-[(1R)-1-hydroxyethyl]-4-methyl-7-oxo-1-azabicyclo [3.2.0]hept-2-ene-2-carboxylic acid (0.47 g) was obtained by hydrogenating 4-nitrobenzyl (4R,5S,6S)-3-[(2S,4S)-2-(1,3-dithiolan-2-yl)-1-(4-nitrobenzyloxycarbonyl) pyrrolidin-4-yl]thio-6-[(1R)-1-hydroxyethyl]-4-methyl-7-oxo-1-azabicyclo-[3.2.0]hept-2-ene-2-carboxylate (1.60 g) in substantially the same manner as that of Example 4-1).

IR (KBr): 1800–1690 cm$^{-1}$

NMR (D$_2$O, δ): 1.22 (6H, t, J=7.2 Hz)

EXAMPLE 6—6)

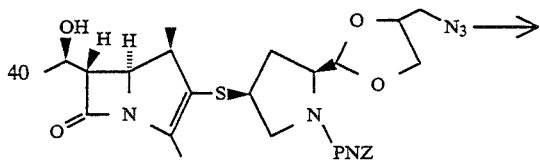

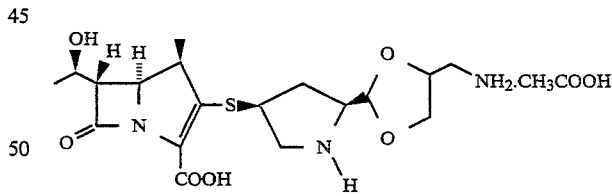

(4R, 5S, 6S)-3-[(2S, 4S)-2-(4-Aminomethyl-1,3-dioxolan-2-yl) pyrrolidin-4-yl]thio-6-[(1R)-1-hydroxyethyl]-4-methyl-7-oxo-1-azabicyclo [3.2.0]hept-2-ene-2-carboxylic acid acetate (0.25 g) was obtained by hydrogenating 4-nitrobenzyl (4R, 5S ,6S)-3-[(2S,4S)-2-(4-azidomethyl-1,3-dioxolan-2-yl) -1-(4-nitrobenzyloxycarbonyl)pyrrolidin-4-yl]thio-6-[(1R)-1-hydroxyethyl]-4-methyl-7-oxo-1-azabicyclo [3.2.0]hept-2-ene-2-carboxylate (0.91 g) in 0.2M acetate buffer (pH 5.8) in substantially the same manner as that of Example 4-1).

IR (Nujol): 1790–1695 cm$^{-1}$

NMR (D$_2$O, δ): 1.25 (6H, t, J=7.2 Hz)

SIMS: 414 (M+−60)

EXAMPLE 6-7)

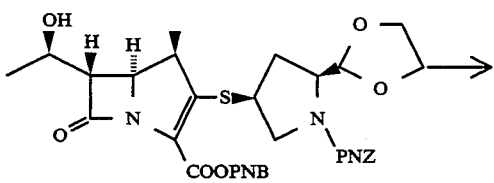

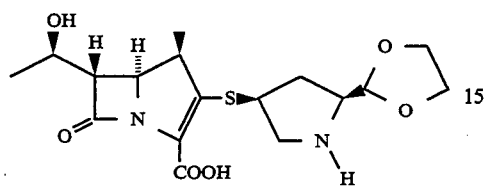

(4R, 5S, 6S)-3-[(2S, 4S)-2-(1,3-Dioxolan-2-yl)-pyrrolidin-4-yl]thio-6-[(1R)-1-hydroxyethyl]-4-methyl-7-oxo-1-azabicyclo [3.2.0]hept-2-ene-2-carboxylic acid (0.42 g) was obtained by hydrogenating 4-nitrobenzyl (4R, 5S, 6S)-3-[(2S, 4S)-2-(1,3-dioxolan-2-yl)-1-(4-nitrobenzyloxycarbonyl)pyrrolidin-4-yl]thio-6-[(1R)-1-hydroxyethyl]-4-methyl-7-oxo-1-azabicyclo[3.2.0]hept-2-ene-2-carboxylate (1.67 g) in substantially the same manner as that of Example 4-1).

IR (Nujol): 1810–1670 cm$^{-1}$

NMR (D$_2$O, δ): 1.25 (6H, t, J=6.5 Hz), 5.15 (1H, d, J=3 Hz)

SIMS: 423 (M$^+$+K), 385 (M$^+$+1)

EXAMPLE 6-8)

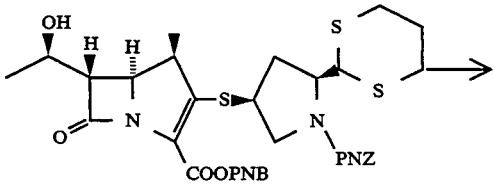

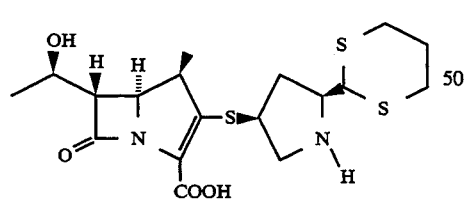

(4R,5S,6S)-3-[(2S,4S)-2-(1,3-Dithian-2-yl)-pyrrolidin-4-yl]thio-6-[(1R)-1-hydroxyethyl]-4-methyl-7-oxo-1-azabicyclo [3.2.0]hept-2-ene-2-carboxylic acid (0.16 g) was obtained by hydrogenating 4-nitrobenzyl (4R,5S,6S)-3-[(2S,4S)-2-(1,3-dithian-2-yl)-1-(4nitrobenzyloxycarbonyl) pyrrolidin-4-yl]thio-6-[(1R)-1-hydroxyethyl]-4-methyl-7-oxo-1-azabicyclo[3.2.0]hept-2-ene-2-carboxylate (1.15 g) in substantially the same manner as that of Example 4-1).

IR (Nujol): 1790–1710 cm$^{-1}$

NMR (D$_2$O, δ): 1.27 (6H, t, J=6.5 Hz)

EXAMPLE 6-9)

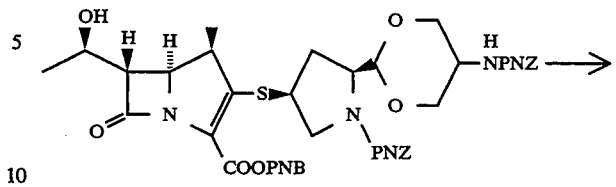

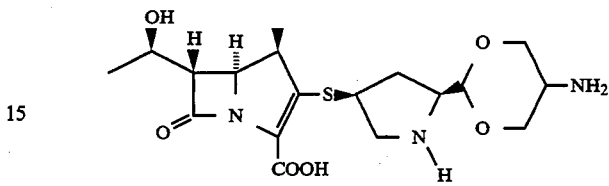

(4R, 5S, 6S)-3-(2S, 4S)-2-(5-Amino-1,3-dioxan-2-yl)-pyrrolidin-4-yl]thio-6-[(1R)-1-hydroxyethyl]-4-methyl-7-oxo-1-azabicyclo [3.2.0]hept-2-ene-2-carboxylic acid (0.23 g) was obtained by hydrogenating 4-nitrobenzyl (4R, 5S, 6S)-6-[(1R)-1-hydroxyethyl]-4-methyl-3-[(2S, 4S)- 1-(4-nitrobenzyloxycarbonyl)-2-{5-(4-nitrobenzyloxycarbonylamino)-1, 3-dioxan-2-yl}-pyrrolidin-4-yl]thio-7-oxo-1-azabicyclo[3.2.0]hept-2-ene-2-carboxylate (0.98 g) in substantially the same manner as that of Example 4-1).

IR (KBr): 1780–1730 cm$^{-1}$

NMR (D$_2$O, δ): 1.23 (3H, t, J=6.4 Hz), 1.25 (3H, t, J=9.2 Hz)

SIMS: 414 (M$^+$), 277 (M$^+$−137)

EXAMPLE 6-10)

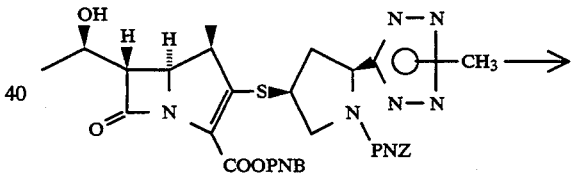

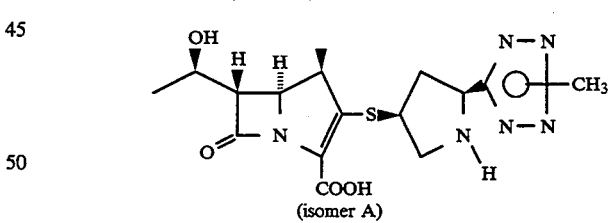

(4R, 5S, 6S)-6-[(1R)-1-Hydroxyethyl]-4-methyl-3-[(2S, 4S)-2-{1(or 2)-methyl-1H(or 2H)-tetrazol-5-yl}-pyrrolidin-4-yl]thio-7-oxo-1-azabicyclo[3.2.0]hept-2-ene-2-carboxylic acid (isomer A) (0.06 g) was obtained by hydrogenating 4-nitrobenzyl (4R, 5S, 6S)-6-[(1R) -hydroxyethyl]-4-methyl-3-[(2S, 4S)-2-{1-(or 2)-methy-1H (or 2H) tetrazol-5-yl}-1-(4-nitrobenzyloxycarbonyl)-pyrrolidin-4-yl]thio-7-oxo-1-azabicyclo[3.2.0]hept-2-ene-2-carboxylate (isomer A) (0.31 g) in substantially the same manner as that of Example 4-1).

mp: 165° C. (dec.)

TLC: Rf 0.3 (silica gel plate, developing solvent: 5% aqueous sodium chloride)

IR (KBr): 1760–1730 cm$^{-1}$

NMR (D₂O, δ): 1.22 (3H, d, J=8 Hz), 1.28 (3H, d, J=8 Hz)
SIMS: 393 (M⁺−1)

EXAMPLE 6-11)

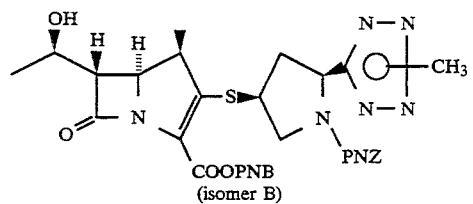
(isomer B)

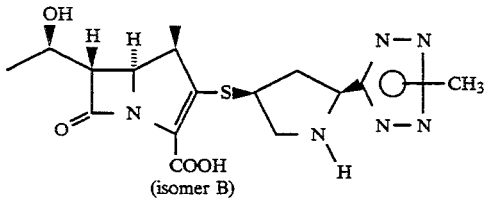
(isomer B)

(4R, 5S, 6S)-6-[(1R)-1-Hydroxyethyl]-4-methyl-3-[(2S, 4S)-2-{2(or 1)-methyl-2H(or 1H)-tetrazol-5-yl}-pyrrolidin-4-yl]thio-7-oxo-1-azabicyclo[3.2.0]hept-2-ene-2-carboxylic acid (isomer B) was obtained by hydrogenating 4-nitrobenzyl (4R,5S, 6S)-6-[(1R)-1-hydroxyethyl]-4-methyl-3-[(2S, 4S)-2-{2(or 1)-methyl-2H(or 1H)- tetrazol-5-yl}-1-(4-nitrobenzyloxycarbonyl)pyrrolidin-4-yl]thio-7-oxo-1-azabicyclo[3.2.0-]hept-2-ene-2-carboxylate (isomer B) (0.34 g) in substantially the same manner as that of Example 4-1).

mp: 165° C. (dec.)
TLC: Rf 0.2 (silica gel plate, developing solvent: 5% aqueous sodium chloride)
IR (KBr): 1755–1730 cm⁻¹
NMR (D₂O, δ): 1.21 (3H, d, J=8 Hz), 1.29 (3H, d, J=8 Hz)
SIMS: 393 (M⁺−1)

EXAMPLE 6-12)

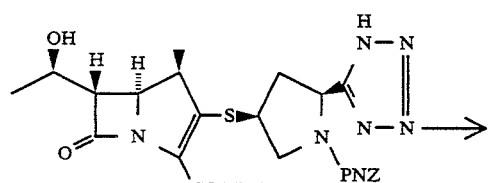

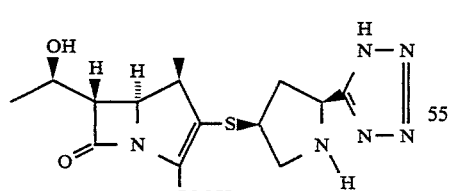

(4R, 5S, 6S)-6-[(1R)-1-Hydroxyethyl]-4-methyl-7-oxo-3- [(2S, 4S)-2-(1H-tetrazol-5-yl)pyrrolidin-4-yl]thio-1-azabicyclo [3.2.0]hept-2-ene-2-carboxylic acid (0.035 g) was obtained by hydrogenating 4-nitrobenzyl (4R, 5S, 6S)- 6-[(1R)-1-hydroxyethyl]-4-methyl-3-[(2S, 4S)-2-(1H- tetrazol-5-yl)-1-(4-nitrobenzyloxycarbonyl)-pyrrolidin-4-yl]thio-7-oxo-1-azabicyclo [3.2.0]hept-2-ene-2-carboxylate (0.30 g) in substantially the same manner as that of Example 4-1).

mp: 220° C. (dec.)
IR (KBr): 1755–1730 cm⁻¹
NMR (D₂O, δ): 1.26 (3H, d, J=8 Hz), 1.33 (2H, d, J=8 Hz)
FD-MS: 419 (M⁺+K), 381 (M⁺+1)

EXAMPLE 7-1

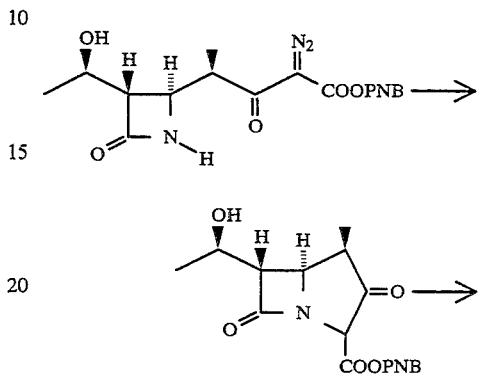

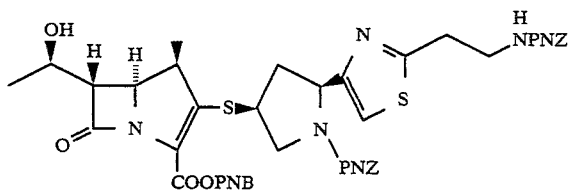

4-Nitrobenzyl(4R, 5S, 6S)-6-[(1R)-1-hydroxyethyl]-4-methyl-3- [(2S, 4S)-1-(4-nitrobenzyloxycarbonyl)-2 [2-{2-(4-nitrobenzyloxycarbonylamino)ethyl}thiazol-4yl]pyrrolidin-4-yl]thio-7-oxo-1-azabicyclo [3.2.0]hept-2-ene-2-carboxylate (550 mg) was obtained by reacting 4-nitrobenzyl, (4R)-2-diazo-4-[(2R, 3S)-3-{(1R)-1-hydroxyethyl}-4-oxoazetidin-2-yl]-3-oxopentanoate (400 mg) with catalytic amount of rhodium(II) acetate and then with (2S, 4S)-4-mercapto-1-(4-nitrobenzyloxycarbonyl)-2-[2-{2- (4-nitrobenzyloxycarbonylamino)ethyl}thiazol-4-yl]pyrrolidine (630 mg) in substantially the same manner as that of Example 2-1).

IR (Nujol): 1760, 1680–1730, 1610 cm⁻¹
NMR (CDCl₃, δ): 1.1–1.5 (6H, m), 4.8–5.7 (8H, m), 7.3–7.8 (6H, m), 7.9–8.3 (6H, m)

EXAMPLE 7-2)

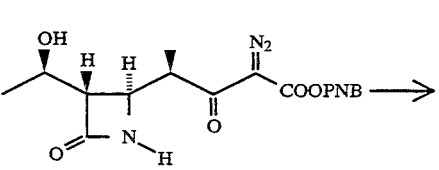

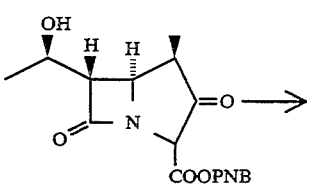

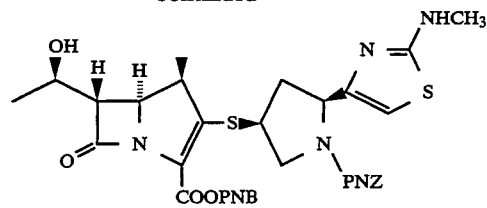

4-Nitrobenzyl (4R, 5S, 6S)-6-[(1R)-1-hydroxyethyl]-4-methyl-3- [(2S, 4S)-2-{2-(methylamino)thiazol-4-yl}-1-(4-nitrobenzyloxycarbonyl) pyrrolidin-4-yl]thio-7-oxo-1-azabicyclo [3.2.0]hept-2-ene-2-carboxylate (880 mg) was obtained by reacting 4-nitrobenzyl (4R)-2-diazo-4-[(2R, 3S)-3- {(1R)-1-hydroxyethyl}-4-oxoazetidin-2-yl]-3-oxopentanoate (960 mg) with catalytic amount of rhodium(II) acetate and then with (2S,4S)-4-mercapto-2-[2-(methylamino) thiazol-4-yl]-1-(4-nitrobenzyloxycarbonyl)pyrrolidine (910 mg) in substantially the same manner as that of Example 2-1).

IR (Nujol): 1765, 1690–1710, 1610 cm$^{-1}$

NMR (CDCl$_3$, δ): 1.1–1.5 (6H, m) , 2.94 (3H, d, J=6 Hz), 6.20 (1H, br s) , 7.0–8.3 (8H, m)

EXAMPLE 7-3)

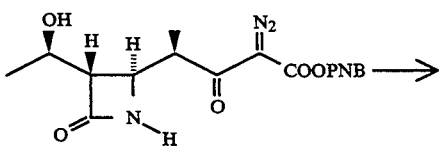

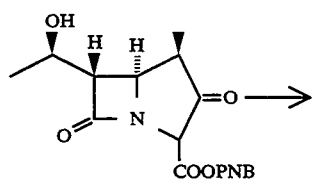

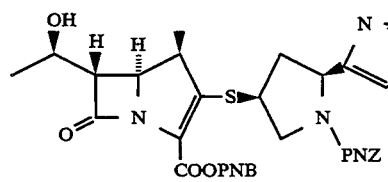

4-Nitrobenzyl (4R,5S,6S)-3-[(2S,4S)-2-{2-carbamoyloxymethyl) thiazol-4-yl}-1-(4-nitrobenzyloxycarbonyl) pyrrolidin-4-yl]thio-6-[(1R)-1-hydroxyethyl]-4-methyl-7-oxo-1-azabicyclo [3.2.0]hept-2-ene-2carboxylate (1.81 g) was obtained by reacting 4-nitrobenzyl (4R)-2-diazo-4-[(2R, 3S)-3-{(1R)-1-hydroxyethyl}-4-oxoazetidin-2-yl]-3-oxopentanoate (1.2 g) with catalytic amount of rhodium (II) acetate and then with (2S, 4S)-2-[2-(carbamoyloxymethyl)thiazol-4-yl]-4-mercapto-1- (4-nitrobenzyloxycarbonyl)pyrrolidine (1.81 g) in substantially the same manner as that of Example 2-1).

IR (CH$_2$Cl$_2$): 3550, 3430, 1770, 1740, 1710, cm$^{-1}$ 1610 cm$^{-1}$

NMR (CDCl$_3$, δ): 1.2–1.5 (6H, m), 4.8–5.6 (7H, m), 6.9–8.4 (9H, m)

EXAMPLE 7-4)

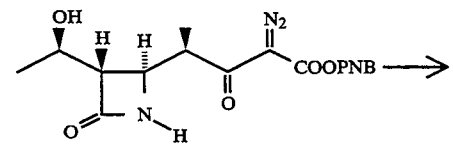

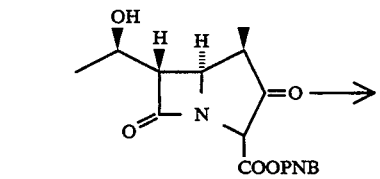

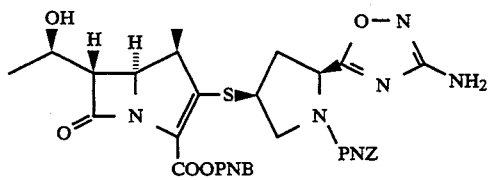

4-Nitrobenzyl (4R, 5S, 6S)-3-[(2S, 4S)-2-(3-amino-1,2,4-oxadiazol-5-yl) -1-(4-nitrobenzyloxycarbonyl)-pyrrolidin-4-yl]thio-6-[(1R)-1-hydroxyethyl]-4-methyl-7-oxo-1-azabicyclo [3.2.0]hept-2-ene-2-carboxylate (360 mg) was obtained by reacting 4-nitrobenzyl (4R)- 2-diazo-4-[(2R, 3S)-3-{(1R)-1-hydroxyethyl}-4-oxoazetidin-2-yl]-3-oxopentanoate (480 mg) with catalytic amount of rhodium(II) acetate and then with (2S, 4S)-2-(3-amino-1,2,4-oxadiazol-5-yl)-4-mercapto-1-(4-nitrobenzyloxycarbonyl) pyrrolidine (400 mg) in substantially the same manner as that of Example 2-1).

IR (CH$_2$Cl$_2$): 1740–1770, 1710, 1610–1630 cm$^{-1}$

NMR (CDCl$_3$, δ): 1.1–1.5 (6H, m), 4.9–5.6 (6H, m), 7.0–7.7 (6H, m), 8.0–8.3 (4H, m)

EXAMPLE 7-5)

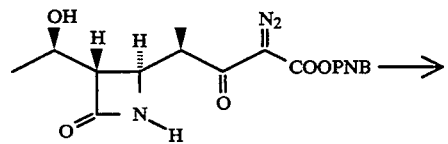

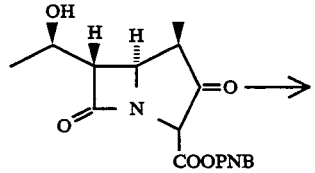

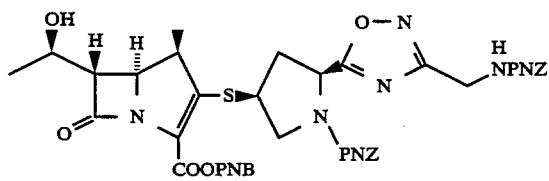

4-Nitrobenzyl (4R, 5S, 6S)-6-[(1R)-1-hydroxyethyl]-4-methyl-3- [(2S, 4S)-1-(4-nitrobenzyloxycarbonyl)-2[3-{N-(4-nitrobenzyloxycarbonyl) aminomethyl}-1,2,4-oxadiazol-5-yl]pyrrolidin-4-yl]thio-7-oxo-1-azabicyclo [3.2.0]hept-2-ene-2-carboxylate (1.64 g) was obtained by reacting 4-nitrobenzyl (4R)-2-diazo-4-[(2R, 3S)-3-

{(1R)-1-hydroxyethyl}-4-oxoazetidin-2-yl]-3-oxopentanoate (1.2 g) with catalytic amount of rhodium(II) acetate and then with (2S, 4S)-4-mercapto-1-(4-nitrobenzyloxycarbonyl) -2-[2-[2-{N-(4-nitrobenzyloxycarbonyl)aminomethyl}- 1,2,4-oxadiazol-5-yl]pyrrolidine (1.4 g) in substantially the same manner as that of Example 2-1).

IR (CH$_2$Cl$_2$): 3600, 3450, 1770, 1710, 1610 cm$^{-1}$

NMR (CDCl$_3$, δ): 0.9–1.6 (6H, m), 4.3–4.6 (2H, m), 7.1–7.7 (6H, m), 8.0–8.3 (6H, m)

EXAMPLE 7-6)

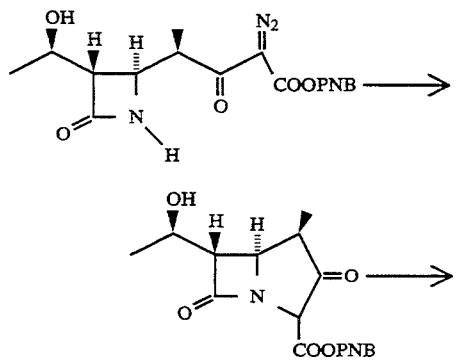

4-Nitrobenzyl (4R, 5S, 6S)-6-[(1R)-1-hydroxyethyl]-4-methyl-3-[(2S, 4S)-1-(4-nitrobenzyloxycarbonyl)-2-[3-{N- (4-nitrobenzyloxycarbonyl)aminomethyl}-1H-1,2,4-triazol-5-yl]pyrrolidin-4-yl]thio-7-oxo-1-azabicyclo-[3.2.0]hept-2-ene-2-carboxylate (430 mg) was obtained by reacting 4-nitrobenzyl (4R)-2-diazo-4-[(2R,3S)-3-{(1R)-1-hydroxyethyl}-4-oxoazetidin-2-yl]-3-oxopentanoate (521 mg) with catalytic amount of rhodium(II) acetate and then with (2S ,4S)-4-mercapto-1-(4-nitrobenzyloxycarbonyl) -2-[3-{N-(4-nitrobenzyloxycarbonyl)aminomethyl}-1H-1, 2,4-triazol-5-yl]pyrrolidine (780 mg) in substantially the same manner as that of Example 2-1).

IR (CH$_2$Cl$_2$): 1780, 1720, 1615 cm$^{-1}$

NMR (CDCl$_3$, δ) : 1.1–1.5 (6H, m) , 4.44 (2H, d, J=6 Hz) , 4.9–5.6 (7H, m) , 7.1–7.7 (6H, m), 8.0–8.3 (6H, m)

EXAMPLE 7—7)

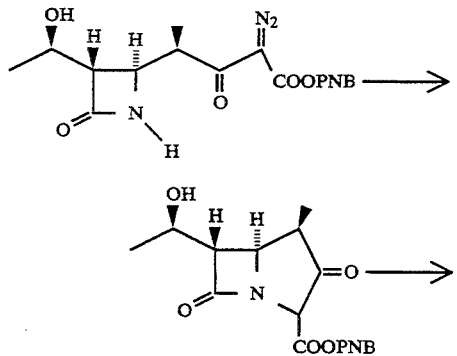

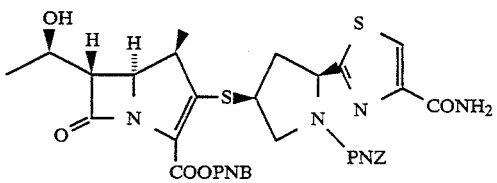

4-Nitrobenzyl (4R,5S, 6S)-3-[(2S ,4S)-2-(4-carbamoylthiazol-2-yl)-1- (4-nitrobenzyloxycarbonyl)pyrrolidin-4-yl]thio-6-[(1R)-1-hydroxyethyl]-4-methyl-7-oxo-1-azabicyclo [3.2.0]hept-2-ene-2-carboxylate (1.05 g) was obtained by reacting 4-nitrobenzyl (4R)-2-diazo-4-[(2R, 3S)-3-{(1R)-1-hydroxyethyl}-4-oxoazetidin-2-yl]-3-oxopentanoate (870 mg) with catalytic amount of rhodium(II) acetate and then with (2S, 4S)-2-(4-carbamoylthiazol-2-yl) -4-mercapto-1-(4-nitrobenzyloxycarbonyl)pyrrolidine (860 mg) in substantially the same manner as that of Example 2-1).

IR (CH$_2$Cl$_2$) 3600, 3520, 3400, 1780, 1710, 1690 cm$^{-1}$

NMR (CDCl$_3$, δ): 1.1–1.4 (6H, m), 5.0–5.7 (5H, m), 5.93 (1H, br s) , 6.9–7.7 (5H, m) , 8.0–8.3 (5H, m)

EXAMPLE 8-1)

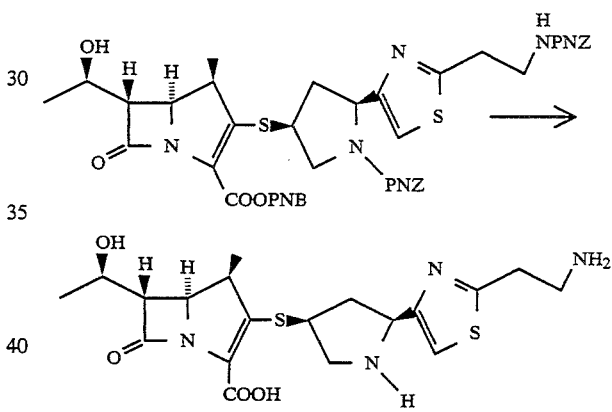

(4R, 5S, 6S)-3-[(2S, 4S)-2-{2-(2-Aminoethyl) thiazol-4-yl}pyrrolidin-4-yl]thio-6-[(1R)-1-hydroxyethyl]-4-methyl- 7-oxo-1-azabicyclo[3.2.0]hept-2-ene-2-carboxylic acid (205 mg) was obtained by hydrogenating 4-nitrobenzyl (4R,5S,6S)-6-[(1R)-1-hydroxyethyl]-4-methyl-3-[(2S,4S)-1-(4-nitrobenzyloxycarbonyl)-2-[2-{2-(4-nitrobenzyloxycarbonylamino) ethyl}thiazol-4-yl]pyrrolidin-4-yl]thio-7-oxo-1-azabicyclo [3.2.0]hept-2-ene-2-carboxylate (1 g) in substantially the same manner as that of Example 4-1).

IR (KBr): 1730–1760 cm$^{-1}$

NMR (D$_2$O, δ): 1.19 (3H, d, J=7 Hz), 1.28 (3H, d, J=6 Hz)

SIMS: 439 (M$^+$+1)

EXAMPLE 8-2)

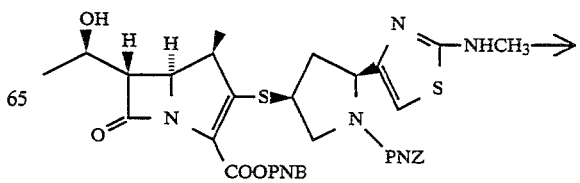

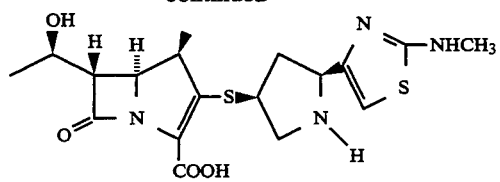
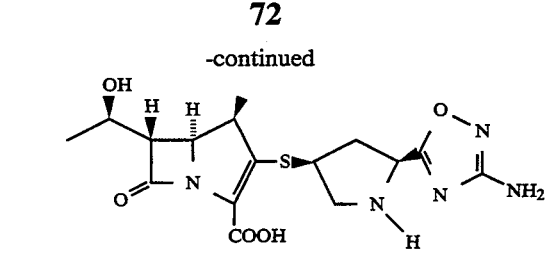

(4R, 5S, 6S)-6-[(1R)-1-Hydroxyethyl]-4-methyl-3-[(2S, 4S)-2-{2-(methylamino)thiazol-4-yl}pyrrolidin-4-yl]-thio-7-oxo-1-azabicyclo [3.2.0]hept-2-ene-2-carboxylic acid (314 mg) was obtained by hydrogenating 4-nitrobenzyl (4R, 5S, 6S)-6-[(1R)-1-hydroxyethyl]-4-methyl-3-[(2S,4S)-2-{2-(methylamino)thiazol-4-yl}-1-(4-nitrobenzyloxycarbonyl) pyrrolidin-4-yl]thio-7-oxo-1-azabicyclo-[3.2.0]hept-2-ene-2-carboxylate (830 mg) in substantially the same manner as that of Example 4-1).

IR (KBr): 2900–3300, 1730–1760 cm⁻¹

NMR (D₂O, δ): 1.20 (3H, d, J=7 Hz), 1.28 (3H, d, J=6 Hz), 6.78 (1H, s)

SIMS: 425 (M⁺+1)

EXAMPLE 8-3)

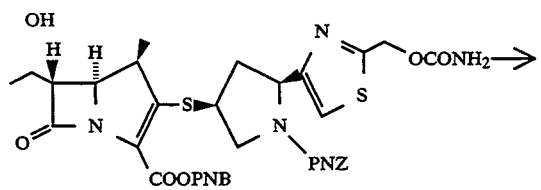

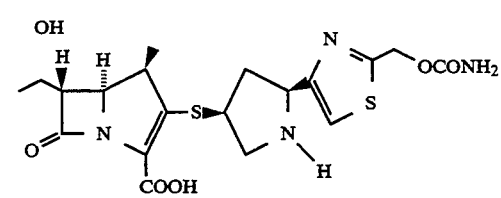

(4R,5S,6S)-3-[(2S,4S)-2-{2-(Carbamoyloxymethyl)thiazol-4-yl}pyrrolidin-4-yl]thio-6-[(1R)-1-hydroxyethyl]-4-methyl-7-oxo-1-azabicyclo[3.2.0]hept-2-ene-2-carboxylic acid (530 mg) was obtained by hydrogenating 4-nitrobenzyl (4R, 5S, 6S)-3-[(2S,4S)-2-{2-(carbamoyloxymethyl)thiazol-4-yl}-1-(4-nitrobenzyloxycarbonyl) pyrrolidin-4-yl]thio-6-[(1R)-1-hydroxyethyl]-4-methyl-7-oxo-1-azabicyclo[3.2.0]hept-2-ene-2-carboxylate (1.8 g) in substantially the same manner as that of Example 4-1).

IR (KBr): 3100–3400, 1710–1760 cm⁻¹

NMR (D₂O, δ): 1.22 (3H, d, J=6 Hz), 1.30 (3H, d, J=6 Hz), 2.0–2.4 (1H, m), 7.71 (1H, s)

SIMS: 469 (M⁺+1)

EXAMPLE 8-4)

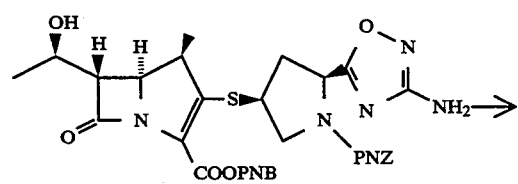

(4R, 5S, 6S)-3-[(2S, 4S)-2-(3-Amino-1,2,4-oxadiazol-5-yl) pyrrolidin-4-yl]thio-6-[(1R)-1-hydroxyethyl]-4-methyl-7-oxo-1-azabicyclo[3.2.0]hept-2-ene-2-carboxylic acid (35 mg) was obtained by reacting 4-nitrobenzyl (4R,5S,6S)-3-[(2S,4S)-2-(3-amino-1, 2,4-oxadiazol-5-yl)-1-(4-nitrobenzyloxycarbonyl)-pyrrolidin-4-yl]thio-6-[(1R)-1-hydroxyethyl]-4-methyl-7-oxo-1-azabicyclo [3.2.0]hept-2-ene-2-carboxylate (360 mg) in substantially the same manner as that of Example 4-1).

IR (KBr): 3100–3400, 1730–1760 cm⁻¹

NMR (D₂O, 1.18 (3H, d, J=7 Hz), 1.28 (3H, d, J=7 Hz)

EXAMPLE 8-5)

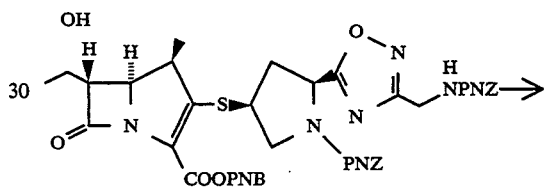

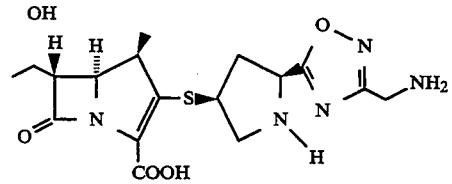

(4R, 5S, 6S)-3-[(2S, 4S)-2-(3-Aminomethyl-1,2,4-oxadiazol-5-yl) pyrrolidin-4-yl]thio-6-[(1R)-1-hydroxyethyl]-4-methyl-7-oxo-1-azabicyclo [3.2.0]hept-2-ene-carboxylic acid (170 mg) was obtained by reacting 4-nitrobenzyl (4R, 5S, 6S)-6-[(1R)-1-hydroxyethyl]-4-methyl-3- [(2S, 4S)-1-(4-nitrobenzyloxycarbonyl)-2-[3-{N-(4-nitrobenzyloxycarbonyl)aminomethyl}-1,2,4-oxadiazol-5-yl]pyrrolidin-4-yl]thio-7-oxo-1azabicyclo [3.2.0]hept-2-ene-2-carboxylate (1.6 g) in substantially the same manner as that of Example 4-1).

IR (KBr): 3200–3400, 1730–1760 cm⁻¹

NMR (D₂O, δ): 1.21 (3H, d, J=7 Hz), 1.29 (3H, d, J=7 Hz)

EXAMPLE 8-6)

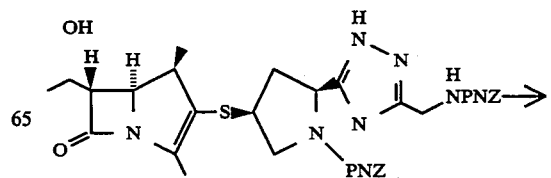

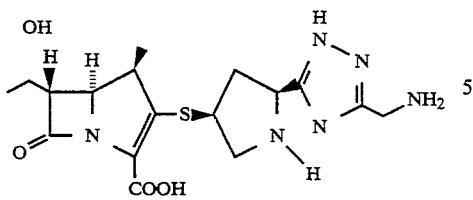

(4R,5S,6S)-3-[(2S,4S)-2-(3-Aminomethyl-1H-1,2,4-triazol-5-yl) pyrrolidin-4-yl]thio-6-[(1R) -1hydroxyethyl]-4-methyl-7-oxo-1-azabicyclo [3.2.0]- hept-2-ene-2-carboxylic acid (110 mg) was obtained by hydrogenating 4-nitrobenzyl (4R, 5S ,6S)-6-[(1R)-1-hydroxyethyl ]-4-methyl-3-[(2S, 4S)-1-(4-nitrobenzyloxycarbonyl) -2-[3-{N-(4-nitrobenzyloxycarbonyl) aminomethyl }-1H-1,2,4-triazol-5-yl]pyrrolidin-4-yl]thio-7-oxo-1-azabicyclo [3.2.0]hept-2-ene-2-carboxylate (430 mg) in substantially the same manner as that of Example 4-1).

IR (KBr): 1730–1750, 1560–1590 cm$^{-1}$

NMR (D$_2$O, δ): 1.19 (3H, d, J=8 Hz), 1.28 (3H, d, J=7 Hz)

SIMS : 409 (M$^+$+1)

EXAMPLE 8-7)

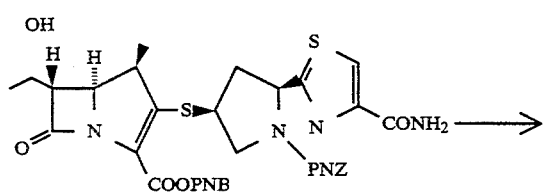

(4R, 5S, 6S)-3-[(2S, 4S)-2-(4-Carbamoylthiazol-2-yl) pyrrolidin-4-yl]thio-6-[(1R)-1-hydroxyethyl]- 4-methyl-7-oxo-1-azabicyclo[3.2.0]hept-2-ene-2-carboxylic acid (370 mg) was obtained by hydrogenating 4-nitrobenzyl (4R,5S ,6S)-3-[(2S,4S)-2-(4-carbamoylthiazol-2-yl) -1-(4-nitrobenzyloxycarbonyl)pyrrolidin-4-yl]thio-6-[(1R)-1-hydroxyethyl]-4-methyl-7-oxo-1-azabicyclo [3.2.0]hept-2-ene-2-carboxylate (1.04 g) in substantially the same manner as that of Example 4-1).

IR (KBr): 3100–3400, 1730–1760 cm$^{-1}$

NMR (D$_2$O, δ) 1.19 (3H, d, J=7 Hz), 1.35 (3H, d, J=6 Hz), 8.31 (1H, s)

SIMS: 437 (M$^+$−1)

EXAMPLE 9-1)

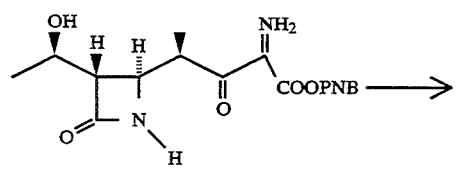

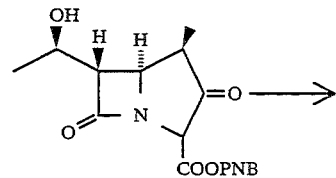

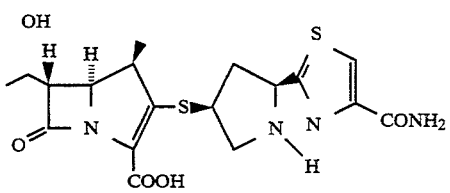

4-Nitrobenzyl (4R, 5S, 6S)-6-[(1R)-1-hydroxyethyl]-4-methyl-3-[(2S, 4S)-1-(4-nitrobenzyloxycarbonyl)-2-(1,2,4-oxadiazol-5-yl) pyrrolidin-4-yl]thio-7-oxo-1-azabicyclo [3.2.0]hept-2-ene-2-carboxylate (1.24 g) was obtained by reacting 4-nitrobenzyl (4R)-2-diazo-4-[(2R, 3S)-3-{(1R)-1-hydroxyethyl}-4-oxoazetidin-2-yl]- 3-oxopentanoate with catalytic amount of rhodium(II) acetate and then with (2S, 4S)-4-mercapto-1-(4-nitrobenzyloxycarbonyl) -2-(1,2,4-oxadiazol-5-yl)pyrrolidine in substantially the same manner as that of Example 2-1).

IR (CH$_2$Cl$_2$): 3400, 1765, 1710, 1610 cm$^{-1}$

NMR (CDCl$_3$, δ): 1.1–1.6 (6H, m), 5.1–5.8 (5H, m), 7.2–7.7 (4H, m) , 8.0–8.3 (4H, m) 8.32 (1H, s)

EXAMPLE 9-2)

4-Nitrobenzyl (4R, 5S, 6S)-6-[(1R)-1-hydroxyethyl]-4-methyl-7-oxo-3-[(2S, 4S)-1-(4-nitrobenzyloxycarbonyl) -2-{2-(ureidomethyl)thiazol-4-yl}pyrrolidin-4-yl]thio-1-azabicyclo [3.2.0]hept-2-ene-2-carboxylate (1.3 g) was obtained by reacting 4-nitrobenzyl (4R) -2-diazo-4-[(2R, 3S)-3-{(1R)-1-hydroxyethyl}-4-oxoazetidin-2-yl]-3-oxopentanoate with catalytic amount of rhodium(II) acetate and then with (2S,4S)-4-mercapto-1-(4-nitrobenzyloxycarbonyl) -2-[2-(ureidomethyl)thiazol-4-yl]pyrrolidine in substantially the same manner as that of Example 2-1).

IR (CH$_2$Cl$_2$): 1760, 1605 cm$^{-1}$

NMR (CDCl₃, δ): 1.1–1.5 (6H, m), 6.9–7.8 (5H, m), 8.0–8.4 (4H, m)

EXAMPLE 9- 3)

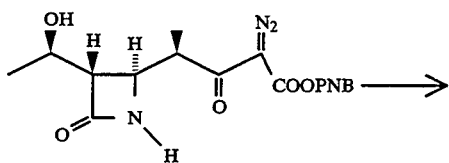

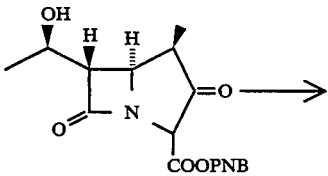

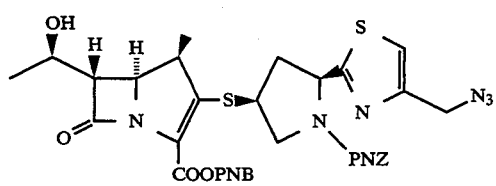

4-Nitrobenzyl (4R,5S,6S)-3-[(2S,4S)-2-(4- azidomethylthiazol-2-yl)-1-(4-nitrobenzyloxycarbonyl)pyrrolidin-4-yl]thio-6-[(1R)-1-hydroxyethyl]-4-methyl-7-oxo-1-azabicyclo [3.2.0]hept-2-ene-2-carboxylate (415 mg) was obtained by reacting 4-nitrobenzyl (4R)-2-diazo-4-[(2R, 3S)-3-{(1R)-1-hydroxyethyl}-4- oxoazetidin-2-yl]-3-oxopentanoate with catalytic amount of rhodium(II) acetate and then with (2S,4S)-2-(4-azidomethylthiazol-2-yl) -4-mercapto-1-(4-nitrobenzyloxycarbonyl) pyrrolidine in substantially the same manner as that of Example 2-1).

IR (CH₂Cl₂): 2200, 1765, 1710, 1605 cm⁻¹
NMR (CDCl₃, δ): 1.1–1.5 (6H, m), 4.39 (2H, s), 5.1–5.6 (5H, m), 8.1–8.4 (4H, m)

EXAMPLE 9-4)

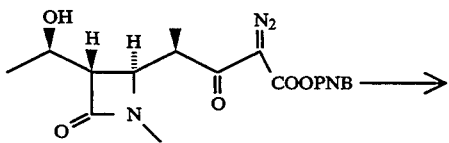

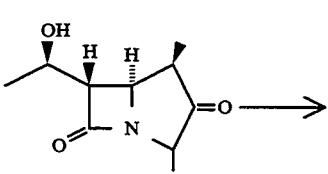

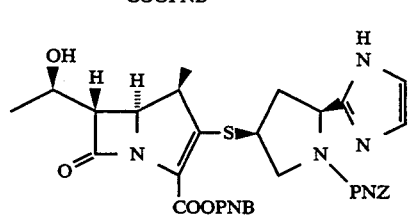

4-Nitrobenzyl (4R, 5S, 6S)-6-[(1R) -1-hydroxyethyl]-3- [(2S, 4S)-2-(imidazol-2-yl)-1-(4-nitrobenzyloxycarbonyl)pyrrolidin-4-yl]thio-4-methyl-7-oxo-1-azabicyclo-[3.2.0]hept-2-ene-2-carboxylate (400 mg) was obtained by reacting 4-nitrobenzyl (4R)-2-diazo-4-[(2R, 3S)- 3-{(1R)-1-hydroxyethyl}-4-oxoazetidin-2-yl]-3-oxopentanoate (870 mg) with catalytic amount of rhodium(II) acetate and then with (2S,4S)-2-(2-imidazol-2-yl)-4-mercapto-1- (4-nitrobenzyloxycarbonyl) pyrrolidine in substantially the same manner as that of Example 2-1).

IR (CH₂Cl₂) 1760, 1700, 1605 cm⁻¹
NMR (CDCl₃, δ): 1.1–1.4 (6H, m), 6.9–7.7 (6H, m), 8.0–8.4 (4H, m)

EXAMPLE 10-1)

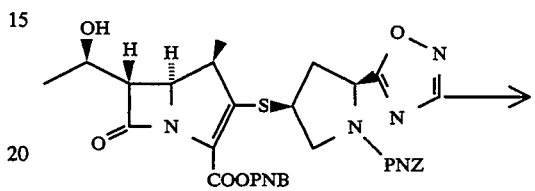

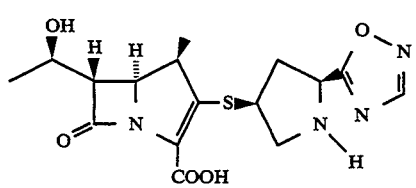

(4R, 5S, 6S)-6-[(1R)-1-Hydroxyethyl]-4-methyl-3-[(2S,4S)-2-(1,2,4-oxadiazol-5-yl)pyrrolidin-4-yl]thio-7-oxo-1-azabicyclo[3.2.0]hept-2-ene-2-carboxylic acid (180 mg) was obtained by hydrogenating 4-nitrobenzyl (4R, 5S, 6S)-6-[(1R)-1-hydroxyethyl]-4-methyl-3-[(2S, 4S)-1-(4-nitrobenzyloxycarbonyl)-2-(1,2,4-oxadiazol-5-yl)- pyrrolidin-4-yl]thio-7-oxo-1-azabicyclo[3.2.0]hept-2-ene-2-carboxylate in substantially the same manner as that of Example 4-1).

IR (KBr): 1730–1750 cm⁻¹
NMR (D₂O, δ): 1.20 (3H, t, J=7 Hz), 1.29 (3H, t, J=7 Hz), 1.8–2.2 (1H, m), 2.7–3.1 (1H, m), 8.19 (1H, s)

EXAMPLE 10-2)

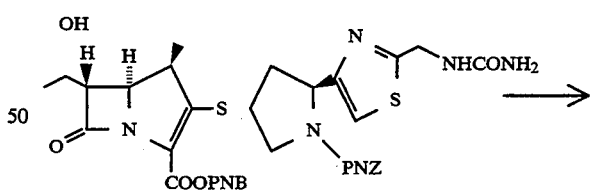

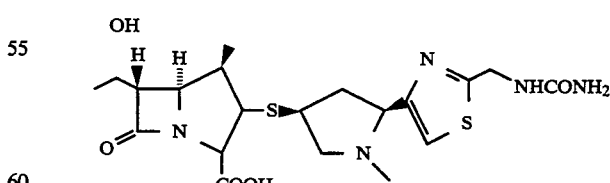

(4R, 5S, 6S)-6-[(1R)-1-Hydroxyethyl]-4-methyl-7-oxo- 3-[(2S, 4S)-2-{2-(ureidomethyl)thiazol-4-yl}pyrrolidin-4-yl]thio-1-azabicyclo [3.2.0]hept-2-ene-2-carboxylic acid (154 mg) was obtained by hydrogenating 4-nitrobenzyl (4R,5 S, 6S)-6-[(1R)-1-hydroxyethyl]-4-methyl-7-oxo-3-(2S, 4S)-1-(4-nitrobenzyloxycarbonyl)-2-{2-(ureidomethyl) thiazol-4-yl}pyrrolidin-4-yl]thio-1- azabicyclo[3.2.0]hept-2-ene-2-carboxylate in substantially the same manner as that of Example 4-1).

IR (KBr): 3200–3400, 1730–1750 cm$^{-1}$
NMR (D$_2$O, δ): 1.18 (3H, d, J=6 Hz), 1.28 (3H, d, J=6 Hz), 7.60 (1H, s)
SIMS: 468 (M$^+$+1)

EXAMPLE 10-3)

(4R,5S, 6S)-3-[(2S, 4S)-2-(4-Aminomethylthiazol-2-yl) pyrrolidin-4-yl]thio-6-[(1R)-1-hydroxyethyl]-4-methyl-7-oxo-1-azabicyclo [3.2.0]hept-2-ene-2-carboxylic acid (120 mg) was obtained by hydrogenating 4-nitrobenzyl (4R,5S,6S)-3-[(2S, 4S)-2-(4-azidomethyl-thiazol-2-yl)-1-(4-nitrobenzyloxycarbonyl) pyrrolidin-4-yl]thio-6-[(1R)- 1-hydroxyethyl]-4-methyl-7-oxo-1-azabicyclo [3.2.0]-hept-2-ene-2-carboxylate in substantially the same manner as that of Example 4-1).

IR (KBr): 1730–1750 cm$^{-1}$
NMR (D$_2$O, δ): 1.23 (3H, d, J=7 Hz), 1.32 (3H, d, J=6 Hz), 7.61 (1H, s)
SIMS: 425 (M$^+$+1)

EXAMPLE 10-4)

(4R, 5S, 6S)-6-[(1R)-1-Hydroxyethyl]-3-[(2S, 4S )-2-(imidazol-2-yl) pyrrolidin-4-yl]thio-4-methyl-7-oxo-1-azabicyclo [3.2.0]hept-2-ene-2-carboxylic acid (68 mg) was obtained by hydrogenating 4-nitrobenzyl (4R,5S,6S)- 6- [(1R)-1-hydroxyethyl]-3-[(2S, 4S)-2-(imidazol-2-yl)-1-(4-nitrobenzyloxycarbonyl) pyrrolidin-4-yl]thio-4-methyl-7-oxo-1-azabicyclo [3.2.0]hept-2-ene-2-carboxylate in substantially the same manner as that of Example 4-1).

IR (KBr): 1730–1760 cm$^{-1}$
NMR (D$_2$O, δ) 1.31 (3H, d, J=7 Hz), 1.41 (3H, d, J=6 Hz), 7.90 (2H, s)

SIMS: 379 (M$^+$+1)

What we claim is:
1. A compound of the formula:

in which R$^1$ is carboxy or protected carboxy,
R$^2$ is hydroxy (lower) alkyl or protected hydroxy (lower) alkyl,
R$^3$ is hydrogen or lower alkyl,
R$^4$ is saturated or unsaturated, 5- or 6-membered heteromonocyclic group containing from 1 to 4 nitrogen atoms, a sulfur atom and from 1 to 2 nitrogen atoms, an oxygen atom and from 1 to 2 nitrogen atoms, from 1 to 2 oxygen atoms or from 1 to 2 sulfur atoms, wherein said heteromonocyclic group may have heteromonocyclic group may have one or more substituent(s) selected from the group consisting of amino, protected amino, lower alkylamino, ureido(lower)alkyl, carbamoyl, lower alkyl, amino(lower)alkyl, protected amino(lower-)alkyl, hydroxy(lower)alkyl, protected hydroxy(-lower)alkyl, azido(lower)alkyl, halo(lower)alkyl, and imino-protective group, and
R$^5$ is hydrogen or imino-protective group, and pharmaceutically acceptable salts thereof.
2. The compound of claim 1, wherein
R$^2$ is hydroxy(C$_1$–C$_4$)alkyl,
R$^3$ is hydrogen or (C$_1$–C$_4$)alkyl,
R$^4$ is said unsaturated 5- or 6-membered heteromonocyclic group, which may have one to three substituent(s) selected from the group consisting of amino, acylamino, C$_1$–C$_4$ alkylamino, ureido(C$_1$–C$_4$)alkyl, carbamoyl, C$_1$–C$_4$ alkyl, amino(C$_1$–C$_4$)alkyl, acylamino(C$_1$–C$_4$)alkyl, hydroxy(C$_1$–C$_4$)alkyl, acyloxy(C$_1$–C$_4$)alkyl, azido(C$_1$–C$_4$)alkyl and halo(C$_1$–C$_4$)alkyl.
3. A compound of claim 2, wherein
R$^3$ is (C$_1$–C$_4$)alkyl.
4. The compound of claim 3, wherein
R$^4$ is imidazolinyl,N-phenyl(or nitrophenyl)(C$_1$–C$_4$)-alkoxycarbonylimidazolinyl, (C$_2$–C$_4$)-alkenyloxycarbonylimidazolinyl, triazolyl, tetrazolyl, thiazolyl, thiadiazolyl, thiazolinyl, oxadiazolyl, imidazolyl, dioxolanyl, dioxanyl, dithiolanyl, or dithianyl, which may have one or two substituent(s) selected from the group consisting of amino, phenyl(or nitrophenyl)(C$_1$–C$_4$) alkoxycarbonylamino, (C$_2$–C$_4$)alkenyloxycarbonylamino, (C$_1$–C$_4$)alkylamino, ureido(C$_1$–C$_4$)alkyl, (C$_1$–C$_4$)alkyl, amino(C$_1$–C$_4$)alkyl, phenyl(or nitrophenyl)(C$_1$–C$_4$)alkylamino(C$_1$–C$_4$) alkyl, (C$_2$–C$_4$)alkenyloxycarbonylamino (C$_1$–C$_4$)alkyl, hydroxy (C$_1$–C$_4$)alkyl, carbamoyloxy (C$_1$–C$_4$) alkyl and azido (C$_1$–C$_4$) alkyl.
5. A compound of claim 4, wherein
R$^2$ is 1-hydroxyethyl,
R$^3$ is methyl, and
R$^4$ is:
imidazolinyl;

N-phenyl (or nitrophenyl) (C$_1$–C$_4$)alkoxycarbonylimidazolinyl;
triazolyl;
amino (C$_1$–C$_4$) alkyltriazolyl;
phenyl (or nitrophenyl) (C$_1$–C$_4$)alkoxycarbonylamino (C$_1$–C$_4$)alkyltriazolyl;
tetrazolyl;
C$_1$–C$_4$ alkyltetrazolyl;
thiazolyl;
aminothiazolyl;
C$_1$–C$_4$ alkylthiazolyl;
carbamoylthiazolyl;
C$_1$–C$_4$ alkylaminothiazolyl;
amino (C$_1$–C$_4$) alkylthiazolyl;
phenyl(or nitrophenyl) (C$_1$–C$_4$)alkoxycarbonylamino (C$_1$–C$_4$)alkylthiazolyl;
carbamoyloxy (C$_1$–C$_4$)alkylthiazolyl;
thiadiazolyl;
C$_1$–C$_4$ alkylaminothiadiazolyl;
thiazolinyl;
aminooxadiazolyl;
amino (C$_1$–C$_4$)alkyloxadiazolyl;
oxadiazolyl;
ureido (C$_1$–C$_4$)alkylthiazolyl;
azido (C$_1$–C$_4$)alkylthiazolyl;
amino (C$_1$–C$_4$)alkylthiazolyl;
imidazolyl;
phenyl (or nitrophenyl) (C$_1$–C$_4$)alkoxycarbonylamino (C$_1$–C$_4$)alkyloxadiazolyl;
dioxolanyl;
amino(C$_1$–C$_4$)alkyldioxolanyl;
azido(C$_1$–C$_4$)alkyldioxolanyl;
hydroxy (C$_1$–C$_4$)alkyldioxolanyl;
aminodioxanyl;
phenyl(or nitrophenyl)(C$_1$–C$_4$) alkoxycarbonylaminodioxanyl;
dithiolanyl; or
dithianyl.

6. A compound of claim 5, wherein R$^4$ is:
2-imidazolin-2-yl;
1-(4-nitrobenzyloxycarbonyl)-2-imidazolin-2-yl;
1H-1,2,4-triazol-3-yl;
3-aminomethyl-1H-1,2,4-triazol-5-yl;
3-(4-nitrobenzyloxycarbonylaminomethyl)-1H-1,2,4-triazol-5-yl;
1H-tetrazol-5-yl;
1-methyl-1H-tetrazol-5-yl, 2-methyl-2H-tetrazol-5-yl;
thiazol-4-yl;
2-aminothiazol-4-yl, 2-methylthiazol-4-yl;
4-carbamoylthiazol-2-yl;
2-methylaminothiazol-4-yl;
2-aminomethylthiazol-4-yl, 2-(2-aminoethyl)-thiazol-4-yl;
2-(4-nitrobenzyloxycarbonylaminomethyl)thiazol-4-yl, 2-[2-(4-nitrobenzyloxycarbonylamino)ethyl]-thiazo-4-yl;
2-carbamoyloxymethylthiazol-4-yl;
1,2,4-thiadiazol-5-yl;
5-methylamino-1,3,4-thiadiazol-2-yl;
2-thiazolin-2-yl;
3-amino-1,2,4-oxadiazol-5-yl;
3-aminomethyl-1,2,4-oxadiazol-5-yl;
1,2,4-oxadiazol-5-yl;
2-ureidomethylthiazol-4-yl;
4-azidomethylthiazol-2-yl;
4-aminomethylthiazol-2-yl;
imidazol-2-yl;
3- (4-nitrobenzyloxycarbonylaminomethyl)-1,2,4-oxadiazol-5-yl;
1,3-dioxolan-2-yl;
4 -aminomethyl-1,3-dioxolan-2-yl;
4 -azidomethyl-1,3-dioxolan-2-yl;
4 -hydroxymethyl-1,3-dioxolan-2-yl;
5-amino-1,3-dioxan-2-yl;
5-(4-nitrobenzyloxycarbonylamino)-1,3-dioxan-2-yl;
1,3-dithiolan-2-yl; or
1,3-dithian-2-yl.

7. A compound of claim 6, which is
(4R, 5S, 6S)-3-[(2S, 4S)-2-{2-(aminomethyl)thiazol-4-yl}]- pyrrolidin-4-ylthio]-6-[(1R)-1-hydroxyethyl]-4-methyl-7-oxo-1-azabicyclo [3.2.0]hept-2-ene-2-carboxylic acid,
(4R, 5S, 6S)-3-[(2S, 4S)-2-(2-imidazolin-2-yl)- pyrrolidin-4-ylthio]-6-[(1R)-1-hydroxyethyl]-4- methyl-7-oxo-1-azabicyclo[3.2.0]hept-2-ene-2-carboxylic acid, or
(4R, 5S, 6S)-3-[(2S, 4S)-2-(5-amino-1,3-dioxan-2-yl)-pyrrolidin-4-ylthio]-6-[(1R)-1-hydroxyethyl]-4-methyl-7-oxo-1-azabicyclo [3.2.0]hept-2-ene-2-carboxylic acid.

8. A compound of claim 2, wherein R$^3$ is hydrogen.

9. The compound of claim 8, wherein R$^4$ is an unsaturated 5- to 6-membered heteromonocyclic group containing 1 sulfur atom and from 1 to 2 nitrogen atom(s), which may have an amino group.

10. A compound of claim 9, wherein R$^4$ is and after unsaturated 5, or 6; membered heteromonocyclic group containing 1 to 2 sulfur atom(s) and nitrogen atom (s), which has an amino group.

11. The compound of claim 10, wherein R$^2$ is 1-hydroxyethyl, and R$^4$ is aminothiazolyl.

12. A compound of claim 11, wherein R$^4$ is 2-aminothiazol-4-yl.

13. The compound of claim 1, wherein R$^4$ is said saturated 5- or 6-membered heteromonocyclic group containing from 1 to 4 nitrogen atoms which may have one or two substituent(s) selected from the group consisting of amino, phenyl(or nitrophenyl)(C$_1$–C$_4$)alkoxycarbonylamino, (C$_2$–C$_4$)alkenyloxycarbonylamino, (C$_1$–C$_4$)alkylamino, ureido(C$_1$–C$_4$)alkyl, (C$_1$–C$_4$)alkyl, amino(C$_1$–C$_4$)alkyl, phenyl(or nitrophenyl)(C$_1$–C$_4$)alkylamino(C$_1$–C$_4$)alkyl, (C$_2$–C$_4$)alkenyloxycarbonylamino(C$_1$–C$_4$)alkyl, hydroxy(C$_1$–C$_4$)alkyl, carbamoyloxy(C$_1$–C$_4$)alkyl and azido(C$_1$–C$_4$)alkyl.

14. The compound of claim 13, wherein R$^4$ is a saturated 5- or 6-membered heteromonocyclic group containing one nitrogen atom which may have one or two substituent(s) selected from the group consisting of amino, phenyl(or nitrophenyl)(C$_1$–C$_4$) alkoxycarbonylamino, (C$_2$–C$_4$) alkenyloxycarbonylamino, (C$_1$–C$_4$)alkylamino, ureido(C$_1$–C$_4$)alkyl, (C$_1$–C$_4$) alkyl, amino(C$_1$–C$_4$)alkyl, phenyl (or nitrophenyl) (C$_1$–C$_4$)alkylamino (C$_1$–C$_4$)alkyl, (C$_2$–C$_4$)alkenyloxycarbonylamino (C$_1$–C$_4$)alkyl, hydroxy(C$_1$–C$_4$)alkyl, carbamoyloxy (C$_1$–C$_4$)alkyl and azido (C$_1$–C$_4$)alkyl.

15. A compound of the formula:

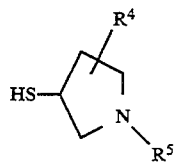

in which $R^4$ and $R^5$ are each as defined in claim 1, or salts thereof.

16. A pharmaceutical composition comprising, as an active ingredient, an effective amount of the compound of claim 1, in admixture with a pharmaceutically acceptable carrier or excipient.

17. A method for the treatment of infectious diseases which comprises administering a compound of claim 1 to human being or animal in need thereof.

* * * * *